(12) United States Patent
Hirai et al.

(10) Patent No.: US 9,157,118 B2
(45) Date of Patent: Oct. 13, 2015

(54) PROBES FOR DETECTING IMMUNE-RELATED GENE POLYMORPHISMS AND APPLICATIONS OF THE SAME

(75) Inventors: Mitsuharu Hirai, Kyoto (JP); Satoshi Majima, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 989 days.

(21) Appl. No.: 12/594,519

(22) PCT Filed: Oct. 3, 2008

(86) PCT No.: PCT/JP2008/068090
§ 371 (c)(1),
(2), (4) Date: Oct. 2, 2009

(87) PCT Pub. No.: WO2009/048027
PCT Pub. Date: Apr. 16, 2009

(65) Prior Publication Data
US 2010/0047806 A1    Feb. 25, 2010

(30) Foreign Application Priority Data

Oct. 9, 2007    (JP) ................................. 2007-263713

(51) Int. Cl.
*C12Q 1/68*    (2006.01)
(52) U.S. Cl.
CPC ............ *C12Q 1/6883* (2013.01); *C12Q 1/6827* (2013.01); *C12Q 2600/156* (2013.01)
(58) Field of Classification Search
None
See application file for complete search history.

(56) References Cited

U.S. PATENT DOCUMENTS

2006/0051353 A1    3/2006   Colombel et al.

FOREIGN PATENT DOCUMENTS

| WO | WO2005/118854 | 12/2005 |
|---|---|---|
| WO | WO2005/123947 | 12/2005 |
| WO | WO2006/075254 | 7/2006 |
| WO | WO2006/125668 | 11/2006 |
| WO | WO2007/073179 | 6/2007 |

OTHER PUBLICATIONS

Dall'Ozzo, S. et al. Journal of Immunological Methods 277:185-192 (2003).*
Ma, H. et al. The Journal of American Science 2(3):1-15 (2006).*
Cartron, et al., "Therapeutic activity of humanized anti-CD20 monoclonal antibody and polymorphism in IgG Fc receptor FcγRIIIa gene", Blood, vol. 99, No. 3, pp. 754-758, 2002.
Hatjiharissi, et al., "Increased natural killer cell expression of CD16, augmented binding and ADCC activity to rituximab among individuals expressing the FcγRIIIa-158 V/V and V/F polymorphism", Blood, vol. 110, No. 7, pp. 2561-2564, 2007.
SNP Report(rs396991(dbSNP127)). [online]. Aug-2007. Archive! Ensembl Human SNPView, Ensembl release 46, Accession rs396991, [Retrieved on Oct. 16, 2008]. Retrieved from internet: <URL: https://www.xennexinc.com/cgi-bin/nph-xp.cgi/000100A/ http/Aug2007.archive.ensembl.org/Homo_sapiens/ snpview?source=dbSNP;snp=396991> (2 pages).
Kurebayashi, et al., "Automated genotyping of human CYP2C19 SNPs by a novel SNP typing system and development of a database of it", The Abstract of the 28th Annual Meeting of the Molecular Biology Society of Japan, p. 472, 3P-1068, 2005, with its partial translation.
Kuroda, et al., "Tailor-made treatment strategy for hemotologic malignancy by novel rapid method for detection of point mutation", The Journal of Japan Society of Cancer Therapy, vol. 42, No. 2, W16-6, 2007, with its partial translation.
Kimura, et al., "Building of a system for analyzing gene polymorphism by an automatic gene analysis device", The Abstract of the 52nd Annual Meeting of the Japan Society of Human Genetics, p. 174, P-116, 2007, with its partial translation.
"Human DNA sequence from clone RP11-5K23 on chromosome 1 Contains the FCGR2A gene for Fc fragment of IgG low affinity IIa receptor for (CD32), the HSPA6 gene for heat shock 70kDa protein 6 (HSP7OB'), a ribosomal protein S23 (RPS23) pseudogene, the FCGR3A gene . . . " GenBank Accession No. AL590385,23 (Jan. 18, 2007).
Helliot, Bertrand, Examiner, Supplementary European Search Report, dated Jul. 12, 2010, 20 pages.
Office Action dated May 25, 2011 in corresponding European Patent Application No. 08837768.4.
Office Action issued in corresponding European Patent Application No. 08837768.4 dated Mar. 4, 2013.
Summons to attend Oral Proceedings issued in corresponding European Patent Application No. 08837768.4 dated Mar. 3, 2015.

* cited by examiner

*Primary Examiner* — Diana B Johannsen
(74) *Attorney, Agent, or Firm* — Morgan, Lewis & Bockius LLP

(57) ABSTRACT

Polymorphism detection probes that can distinguish polymorphisms that have only one different base are provided. At least one oligonucleotide selected from the group consisting of the oligonucleotides of SEQ ID NOS. 4, 23, 30, 47, 57 and 64 is used as a probe in a Tm analysis. A Tm analysis using such probes allows easy detection of specific polymorphisms of the FCGR3A gene, the FCGR2A gene, the IL-10 gene, the TNF α gene and the TNF β gene that have an effect on the pharmaceutical effects of antibody drugs or the like. Moreover, such probes allow detection of two or more types of polymorphisms in a single reaction system by introducing two or more types of the probes concomitantly.

9 Claims, 3 Drawing Sheets

```
                         SEQUENCE LISTING

<160> NUMBER OF SEQ ID NOS: 349

<210> SEQ ID NO 1
<211> LENGTH: 401
<212> TYPE: DNA
<213> ORGANISM: Homo sapiens

<400> SEQUENCE: 1
tgttgctcca ggcccctcgg tgggtgttca aggaggaaga ccctattcac ctgaggtgtc      60
acagctggaa gaacactgct ctgcataagg tcacatattt acagaatggc aaaggcagga    120
agtattttca tcataattct gacttctaca ttccaaaagc cacactcaaa gacagcggct    180
cctacttctg caggggcttt kttgggagta aaaatgtgtc ttcagagact gtgaacatca    240
ccatcactca aggtgagaca tgtgccaccc tggaatgccc agggacgcct gtgtgtggaa    300
cctgcaatca cactgggaag ttgagttggg aggagattcc tgattcttac acgcacttct    360
tcatatgtgg ttccctcctg gtgatcacca ggaggtcccc a                        401

<210> SEQ ID NO 2
<211> LENGTH: 501
<212> TYPE: DNA
<213> ORGANISM: Homo sapiens

<400> SEQUENCE: 2
acctccatgt aggcccatgt gacctcagcc cttgtccatc ccctcttctc ccctccctac      60
atcttggcag actccccata ccttggacag tgatggtcac aggcttggat gagaacagcg    120
tgtagcctat gtttcctgtg cagtggtaat caccactgtg actgtggttt gcttgtggga    180
tggagaaggt gggatccaaa ygggagaatt tctgggattt tccattctgg aagaatgtga    240
ccttgaccag aggcttgtcc ttccagctgt ggcacctcag catgatggtt tctccctcct    300
ggaactccag gtgaggggtc tggagcacca gccattctga aagacacaaa tatgataaga    360
aaaagttgta aggatagatt ccaagggttt ttcagtctca gaggtacgtt actcacagaa    420
cttgacatga tgtctggcag acagaaatga agatgcttca tgacagatgt gagcattctc    480
ttataggcaa tatatggtat t                                              501

<210> SEQ ID NO 3
<211> LENGTH: 601
<212> TYPE: DNA
<213> ORGANISM: Homo sapiens

<400> SEQUENCE: 3
gagatggtgt acagtagggt gaggaaacca aattctcagt tggcactggt gtacccttgt      60
acaggtgatg taacatctct gtgcctcagt ttgctcacta taaatagag acggtagggg     120 tcatggtgag cactacctga ctagcatata agaagctttc agcaagtgca gactactctt    180
acccacttcc cccaagcaca gttggggtgg gggacagctg aagaggtgga aacatgtgcc    240
```

```
tgagaatcct aatgaaatcg gggtaaagga gcctggaaca catcctgtga ccccgcctgt    300
mctgtaggaa gccagtctct ggaaagtaaa atggaagggc tgcttgggaa ctttgaggat    360
atttagccca cccctcatt tttacttggg gaaactaagg cccagagacc taaggtgact     420
gcctaagtta gcaaggagaa gtcttgggta ttcatcccag gttgggggga cccaattatt    480
tctcaatccc attgtattct ggaatgggca atttgtccac gtcactgtga cctaggaaca    540
cgcgaatgag aacccacagc tgagggcctc tgcgcacaga acagctgttc tccccaggaa    600
a                                                                  601
```

<210> SEQ ID NO 4
<211> LENGTH: 801
<212> TYPE: DNA
<213> ORGANISM: Homo sapiens

<400> SEQUENCE: 4

```
ccttccccag gtagagcaac actcctcgcc gcaacccaac tggctcccct taccttctac     60
acacacacac acacacacac acacacacac acacacacac acaaatccaa gacaacacta   120
ctaaggcttc tttgggaagg ggaagtaggg ataggtaaga ggaaagtaag ggacctccta   180
tccagcctcc atggaatcct gacttctttt ccttgttatt tcaacttctt ccaccccatc   240
ttttaaactt tagactccag ccacagaagc ttacaactaa agaaactct aaggccaatt    300 taatccaagg tttcattcta tgtgctggag atggtgtaca gtagggtgag gaaaccaaat   360
tctcagttgg cactggtgta cccttgtaca ggtgatgtaa yatctctgtg cctcagtttg   420
ctcactataa aatagagacg gtaggggtca tggtgagcac tacctgacta gcatataaga   480
agctttcagc aagtgcagac tactcttacc cacttccccc aagcacagtt ggggtggggg   540
acagctgaag aggtggaaac atgtgcctga gaatcctaat gaaatcgggg taaaggagcc   600
tggaacacat cctgtgaccc cgcctgtact gtaggaagcc agtctctgga agtaaaatg    660 gaagggctgc ttgggaactt tgaggatatt tagcccaccc cctcatttt acttggggaa    720 actaaggccc agagacctaa ggtgactgcc taagttagca aggagaagtc ttgggtattc   780
atcccaggtt gggggaccc a                                              801
```

<210> SEQ ID NO 5
<211> LENGTH: 913
<212> TYPE: DNA
<213> ORGANISM: Homo sapiens
<220> FEATURE:
<221> NAME/KEY: misc_feature
<222> LOCATION: (800)..(899)
<223> OTHER INFORMATION: n stands for any base
<220> FEATURE:
<221> NAME/KEY: misc_feature
<222> LOCATION: (226)..(227)
<223> OTHER INFORMATION: n stands for any base

<400> SEQUENCE: 5

```
tcaatgctcc ctggcaggca ggaggacagg tgctattgcc ctgttgggac agatgaaaaa    60
cagacacagg gaggatgagt gatttgccct gactatagag tggcagggcc aaggcagagc   120
ccaggcctcc tgcacctagg tcagtgttcc tcccagttac agtctaaact ggaatggcag   180
gcaaagcccc tgtggaaggg gaaggtgaag ctcaaatcaa agctcnncca gagactttcc   240
agatatctga gaagtcctg atgtcactgc cccggtcctt ccccaggtag agcaacactc    300
ctcgccgcaa cccaactggc tctccttact ttctacacac acacacacac acacacacac   360
acacacacac acacacacaa atccaagaca acactactaa ggcttctttg ggargggggaa  420
```

| | | |
|---|---|---|
| gtagggatag gtaagaggaa agtaagggac ctcctatcca gcctccatgg aatcctgact | 480 | |
| tcttttcctt gttatttcaa cttcttccac cccatctttt aaactttaga ctccagccac | 540 | |
| agaagcttac aactaaaaga aactctaagg ccaatttaat ccaaggtttc attctatgtg | 600 | |
| ctggagatgg tgtacagtag ggtgaggaaa ccaaattctc agttggcact ggtgtaccct | 660 | |
| tgtacaggtg atgtaatatc tctgtgcctc agtttgctca ctataaaata gagacggtag | 720 | |
| gggtcatggt gagcactacc tgactagcat ataagaagtt tcagcaagtg ggggatcctc | 780 | |
| tagagtcgcg acctcagcan nnnnnnnnnn nnnnnnnnnn nnnnnnnnnn nnnnnnnnnn | 840 | |
| nnnnnnnnnn nnnnnnnnnn nnnnnnnnnn nnnnnnnnnn nnnnnnnnnn nnnnnnnnng | 900 | |
| gattttggat tca | 913 | |

<210> SEQ ID NO 6
<211> LENGTH: 465
<212> TYPE: DNA
<213> ORGANISM: Homo sapiens

<400> SEQUENCE: 6

| | | |
|---|---|---|
| gagtgagaca gaaaataaaa tacaaccccc tcttttaawa gccatgctta ctcaggtttt | 60 | |
| ccttcatttg cagctaaata cagaaatgag agaatatttt ggagcaggga tggaagaaga | 120 | |
| gaggtattcc ccttcccaca awcttctgat ttcccagtac atcccccact ggaaaaatwc | 180 | |
| atttaaaatc agtataataa gcattgattr gatgcctact atgcatctgg gcttgagggc | 240 | |
| aaactggact caggcctttt ggcctcaaga agctcacagt gtgagagtgg catttgtgtc | 300 | |
| ctcttgaaat tcacaggact aaattgtgcc caggctgaca ttctatccat ccataggtgc | 360 | |
| ctgccttctc acttccctct cttcatgggc tcttgccttg taccaaaatc caaacccaaa | 420 | |
| tctcctcaca tgtgagtgtt ggcattcatg tctcagacat gacct | 465 | |

<210> SEQ ID NO 7
<211> LENGTH: 801
<212> TYPE: DNA
<213> ORGANISM: Homo sapiens

<400> SEQUENCE: 7

| | | |
|---|---|---|
| ttccttggaa gccaagactg aaaccagcat tatgagtctc cgggtcagaa tgaaagaaga | 60 | |
| aggcctgccc cagtggggtc tgtgaattcc cgggggtgat ttcactcccc ggggctgtcc | 120 | |
| caggcttgtc cctgctaccc ccacccagcc tttcctgagg cctcaagcct gccaccaagc | 180 | |
| ccccagctcc ttctccccgc agggacccaa acacaggcct caggactcaa cacagctttt | 240 | |
| ccctccaacc ccgttttctc tccctcaagg actcagcttt ctgaagcccc tcccagttct | 300 | |
| agttctatct ttttcctgca tcctgtctgg aagttagaag gaaacagacc acagacctgg | 360 | |
| tccccaaaag aaatggaggc aataggtttt gaggggcatg rggacggggt tcagcctcca | 420 | |
| gggtcctaca cacaaatcag tcagtggccc agaagacccc cctcggaatc ggagcaggga | 480 | |
| ggatggggag tgtgaggggt atccttgatg cttgtgtgtc cccaactttc caaatccccg | 540 | |
| cccccgcgat ggagaagaaa ccgagacaga aggtgcaggg cccactaccg cttcctccag | 600 | |
| atgagctcat gggtttctcc accaaggaag ttttccgctg gttgaatgat tctttccccg | 660 | |
| ccctcctctc gccccaggga catataaagg cagttgttgg cacacccagc cagcagacgc | 720 | |
| tccctcagca aggacagcag aggaccagct aagagggaga gaagcaacta cagaccccccc | 780 | |
| ctgaaaacaa ccctcagacg c | 801 | |

-continued

<210> SEQ ID NO 8
<211> LENGTH: 21
<212> TYPE: DNA
<213> ORGANISM: Artificial
<220> FEATURE:
<223> OTHER INFORMATION: probe

<400> SEQUENCE: 8
ttttactccc aaaaagcccc c                                              21

<210> SEQ ID NO 9
<211> LENGTH: 20
<212> TYPE: DNA
<213> ORGANISM: Artificial
<220> FEATURE:
<223> OTHER INFORMATION: probe

<400> SEQUENCE: 9
tttactccca aaagccccc                                                 20

<210> SEQ ID NO 10
<211> LENGTH: 19
<212> TYPE: DNA
<213> ORGANISM: Artificial
<220> FEATURE:
<223> OTHER INFORMATION: probe

<400> SEQUENCE: 10
ttactcccaa aaagccccc                                                 19

<210> SEQ ID NO 11
<211> LENGTH: 18
<212> TYPE: DNA
<213> ORGANISM: Artificial
<220> FEATURE:
<223> OTHER INFORMATION: probe

<400> SEQUENCE: 11
tactcccaaa aagccccc                                                  18

<210> SEQ ID NO 12
<211> LENGTH: 17
<212> TYPE: DNA
<213> ORGANISM: Artificial
<220> FEATURE:
<223> OTHER INFORMATION: probe

<400> SEQUENCE: 12
actcccaaaa agccccc                                                   17

<210> SEQ ID NO 13
<211> LENGTH: 16
<212> TYPE: DNA
<213> ORGANISM: Artificial
<220> FEATURE:
<223> OTHER INFORMATION: probe

<400> SEQUENCE: 13
ctcccaaaaa gccccc                                                    16

<210> SEQ ID NO 14
<211> LENGTH: 15
<212> TYPE: DNA
<213> ORGANISM: Artificial
<220> FEATURE:
<223> OTHER INFORMATION: probe

```
<400> SEQUENCE: 14
tcccaaaaag ccccc                                                    15

<210> SEQ ID NO 15
<211> LENGTH: 14
<212> TYPE: DNA
<213> ORGANISM: Artificial
<220> FEATURE:
<223> OTHER INFORMATION: probe

<400> SEQUENCE: 15
cccaaaaagc cccc                                                     14

<210> SEQ ID NO 16
<211> LENGTH: 13
<212> TYPE: DNA
<213> ORGANISM: Artificial
<220> FEATURE:
<223> OTHER INFORMATION: probe

<400> SEQUENCE: 16
ccaaaaagcc ccc                                                      13

<210> SEQ ID NO 17
<211> LENGTH: 24
<212> TYPE: DNA
<213> ORGANISM: Artificial
<220> FEATURE:
<223> OTHER INFORMATION: probe

<400> SEQUENCE: 17
cagaaattct cccatttgga tccc                                          24

<210> SEQ ID NO 18
<211> LENGTH: 23
<212> TYPE: DNA
<213> ORGANISM: Artificial
<220> FEATURE:
<223> OTHER INFORMATION: probe

<400> SEQUENCE: 18
agaaattctc ccatttggat ccc                                           23

<210> SEQ ID NO 19
<211> LENGTH: 22
<212> TYPE: DNA
<213> ORGANISM: Artificial
<220> FEATURE:
<223> OTHER INFORMATION: probe

<400> SEQUENCE: 19
gaaattctcc catttggatc cc                                            22

<210> SEQ ID NO 20
<211> LENGTH: 21
<212> TYPE: DNA
<213> ORGANISM: Artificial
<220> FEATURE:
<223> OTHER INFORMATION: probe

<400> SEQUENCE: 20
aaattctccc atttggatcc c                                             21

<210> SEQ ID NO 21
```

```
<211> LENGTH: 20
<212> TYPE: DNA
<213> ORGANISM: Artificial
<220> FEATURE:
<223> OTHER INFORMATION: probe

<400> SEQUENCE: 21
aattctccca tttggatccc                                                    20

<210> SEQ ID NO 22
<211> LENGTH: 19
<212> TYPE: DNA
<213> ORGANISM: Artificial
<220> FEATURE:
<223> OTHER INFORMATION: probe

<400> SEQUENCE: 22
attctcccat ttggatccc                                                     19

<210> SEQ ID NO 23
<211> LENGTH: 18
<212> TYPE: DNA
<213> ORGANISM: Artificial
<220> FEATURE:
<223> OTHER INFORMATION: probe

<400> SEQUENCE: 23
ttctcccatt tggatccc                                                      18

<210> SEQ ID NO 24
<211> LENGTH: 17
<212> TYPE: DNA
<213> ORGANISM: Artificial
<220> FEATURE:
<223> OTHER INFORMATION: probe

<400> SEQUENCE: 24
tctcccattt ggatccc                                                       17

<210> SEQ ID NO 25
<211> LENGTH: 16
<212> TYPE: DNA
<213> ORGANISM: Artificial
<220> FEATURE:
<223> OTHER INFORMATION: probe

<400> SEQUENCE: 25
ctcccatttg gatccc                                                        16

<210> SEQ ID NO 26
<211> LENGTH: 15
<212> TYPE: DNA
<213> ORGANISM: Artificial
<220> FEATURE:
<223> OTHER INFORMATION: probe

<400> SEQUENCE: 26
tcccatttgg atccc                                                         15

<210> SEQ ID NO 27
<211> LENGTH: 21
<212> TYPE: DNA
<213> ORGANISM: Artificial
<220> FEATURE:
<223> OTHER INFORMATION: probe

<400> SEQUENCE: 27
```

```
cttcctacag tacaggcggg g                                              21

<210> SEQ ID NO 28
<211> LENGTH: 20
<212> TYPE: DNA
<213> ORGANISM: Artificial
<220> FEATURE:
<223> OTHER INFORMATION: probe

<400> SEQUENCE: 28
cttcctacag tacaggcggg                                                20

<210> SEQ ID NO 29
<211> LENGTH: 19
<212> TYPE: DNA
<213> ORGANISM: Artificial
<220> FEATURE:
<223> OTHER INFORMATION: probe

<400> SEQUENCE: 29
cttcctacag tacaggcgg                                                 19

<210> SEQ ID NO 30
<211> LENGTH: 18
<212> TYPE: DNA
<213> ORGANISM: Artificial
<220> FEATURE:
<223> OTHER INFORMATION: probe

<400> SEQUENCE: 30
cttcctacag tacaggcg                                                  18

<210> SEQ ID NO 31
<211> LENGTH: 17
<212> TYPE: DNA
<213> ORGANISM: Artificial
<220> FEATURE:
<223> OTHER INFORMATION: probe

<400> SEQUENCE: 31
cttcctacag tacaggc                                                   17

<210> SEQ ID NO 32
<211> LENGTH: 16
<212> TYPE: DNA
<213> ORGANISM: Artificial
<220> FEATURE:
<223> OTHER INFORMATION: probe

<400> SEQUENCE: 32
cttcctacag tacagg                                                    16

<210> SEQ ID NO 33
<211> LENGTH: 22
<212> TYPE: DNA
<213> ORGANISM: Artificial
<220> FEATURE:
<223> OTHER INFORMATION: probe

<400> SEQUENCE: 33
ggcacagaga tgttacatca cc                                             22

<210> SEQ ID NO 34
<211> LENGTH: 21
<212> TYPE: DNA
```

```
<213> ORGANISM: Artificial
<220> FEATURE:
<223> OTHER INFORMATION: probe

<400> SEQUENCE: 34
gcacagagat gttacatcac c                                          21

<210> SEQ ID NO 35
<211> LENGTH: 20
<212> TYPE: DNA
<213> ORGANISM: Artificial
<220> FEATURE:
<223> OTHER INFORMATION: probe

<400> SEQUENCE: 35
cacagagatg ttacatcacc                                            20

<210> SEQ ID NO 36
<211> LENGTH: 19
<212> TYPE: DNA
<213> ORGANISM: Artificial
<220> FEATURE:
<223> OTHER INFORMATION: probe

<400> SEQUENCE: 36
acagagatgt tacatcacc                                             19

<210> SEQ ID NO 37
<211> LENGTH: 18
<212> TYPE: DNA
<213> ORGANISM: Artificial
<220> FEATURE:
<223> OTHER INFORMATION: probe

<400> SEQUENCE: 37
cagagatgtt acatcacc                                              18

<210> SEQ ID NO 38
<211> LENGTH: 17
<212> TYPE: DNA
<213> ORGANISM: Artificial
<220> FEATURE:
<223> OTHER INFORMATION: probe

<400> SEQUENCE: 38
agagatgtta catcacc                                               17

<210> SEQ ID NO 39
<211> LENGTH: 16
<212> TYPE: DNA
<213> ORGANISM: Artificial
<220> FEATURE:
<223> OTHER INFORMATION: probe

<400> SEQUENCE: 39
gagatgttac atcacc                                                16

<210> SEQ ID NO 40
<211> LENGTH: 24
<212> TYPE: DNA
<213> ORGANISM: Artificial
<220> FEATURE:
<223> OTHER INFORMATION: probe

<400> SEQUENCE: 40
ccctacttcc ccctcccaaa gaag                                       24
```

```
<210> SEQ ID NO 41
<211> LENGTH: 23
<212> TYPE: DNA
<213> ORGANISM: Artificial
<220> FEATURE:
<223> OTHER INFORMATION: probe

<400> SEQUENCE: 41
ccctacttcc ccctcccaaa gaa                                            23

<210> SEQ ID NO 42
<211> LENGTH: 22
<212> TYPE: DNA
<213> ORGANISM: Artificial
<220> FEATURE:
<223> OTHER INFORMATION: probe

<400> SEQUENCE: 42
ccctacttcc ccctcccaaa ga                                             22

<210> SEQ ID NO 43
<211> LENGTH: 21
<212> TYPE: DNA
<213> ORGANISM: Artificial
<220> FEATURE:
<223> OTHER INFORMATION: probe

<400> SEQUENCE: 43
ccctacttcc ccctcccaaa g                                              21

<210> SEQ ID NO 44
<211> LENGTH: 20
<212> TYPE: DNA
<213> ORGANISM: Artificial
<220> FEATURE:
<223> OTHER INFORMATION: probe

<400> SEQUENCE: 44
ccctacttcc ccctcccaaa                                                20

<210> SEQ ID NO 45
<211> LENGTH: 19
<212> TYPE: DNA
<213> ORGANISM: Artificial
<220> FEATURE:
<223> OTHER INFORMATION: probe

<400> SEQUENCE: 45
ccctacttcc ccctcccaa                                                 19

<210> SEQ ID NO 46
<211> LENGTH: 18
<212> TYPE: DNA
<213> ORGANISM: Artificial
<220> FEATURE:
<223> OTHER INFORMATION: probe

<400> SEQUENCE: 46
ccctacttcc ccctccca                                                  18

<210> SEQ ID NO 47
<211> LENGTH: 17
<212> TYPE: DNA
<213> ORGANISM: Artificial
<220> FEATURE:
```

```
<223> OTHER INFORMATION: probe

<400> SEQUENCE: 47
ccctacttcc ccctccc                                                    17

<210> SEQ ID NO 48
<211> LENGTH: 16
<212> TYPE: DNA
<213> ORGANISM: Artificial
<220> FEATURE:
<223> OTHER INFORMATION: probe

<400> SEQUENCE: 48
ccctacttcc ccctcc                                                     16

<210> SEQ ID NO 49
<211> LENGTH: 15
<212> TYPE: DNA
<213> ORGANISM: Artificial
<220> FEATURE:
<223> OTHER INFORMATION: probe

<400> SEQUENCE: 49
ccctacttcc ccctc                                                      15

<210> SEQ ID NO 50
<211> LENGTH: 27
<212> TYPE: DNA
<213> ORGANISM: Artificial
<220> FEATURE:
<223> OTHER INFORMATION: probe

<400> SEQUENCE: 50
cccactggaa aaattcattt aaaatca                                         27

<210> SEQ ID NO 51
<211> LENGTH: 26
<212> TYPE: DNA
<213> ORGANISM: Artificial
<220> FEATURE:
<223> OTHER INFORMATION: probe

<400> SEQUENCE: 51
cccactggaa aaattcattt aaaatc                                          26

<210> SEQ ID NO 52
<211> LENGTH: 25
<212> TYPE: DNA
<213> ORGANISM: Artificial
<220> FEATURE:
<223> OTHER INFORMATION: probe

<400> SEQUENCE: 52
cccactggaa aaattcattt aaaat                                           25

<210> SEQ ID NO 53
<211> LENGTH: 24
<212> TYPE: DNA
<213> ORGANISM: Artificial
<220> FEATURE:
<223> OTHER INFORMATION: probe

<400> SEQUENCE: 53
cccactggaa aaattcattt aaaa                                            24
```

```
<210> SEQ ID NO 54
<211> LENGTH: 23
<212> TYPE: DNA
<213> ORGANISM: Artificial
<220> FEATURE:
<223> OTHER INFORMATION: probe

<400> SEQUENCE: 54
cccactggaa aaattcattt aaa                                              23

<210> SEQ ID NO 55
<211> LENGTH: 22
<212> TYPE: DNA
<213> ORGANISM: Artificial
<220> FEATURE:
<223> OTHER INFORMATION: probe

<400> SEQUENCE: 55
cccactggaa aaattcattt aa                                               22

<210> SEQ ID NO 56
<211> LENGTH: 21
<212> TYPE: DNA
<213> ORGANISM: Artificial
<220> FEATURE:
<223> OTHER INFORMATION: probe

<400> SEQUENCE: 56
cccactggaa aaattcattt a                                                21

<210> SEQ ID NO 57
<211> LENGTH: 20
<212> TYPE: DNA
<213> ORGANISM: Artificial
<220> FEATURE:
<223> OTHER INFORMATION: probe

<400> SEQUENCE: 57
cccactggaa aaattcattt                                                  20

<210> SEQ ID NO 58
<211> LENGTH: 19
<212> TYPE: DNA
<213> ORGANISM: Artificial
<220> FEATURE:
<223> OTHER INFORMATION: probe

<400> SEQUENCE: 58
cccactggaa aaattcatt                                                   19

<210> SEQ ID NO 59
<211> LENGTH: 18
<212> TYPE: DNA
<213> ORGANISM: Artificial
<220> FEATURE:
<223> OTHER INFORMATION: probe

<400> SEQUENCE: 59
cccactggaa aaattcat                                                    18

<210> SEQ ID NO 60
<211> LENGTH: 17
<212> TYPE: DNA
<213> ORGANISM: Artificial
<220> FEATURE:
<223> OTHER INFORMATION: probe
```

```
<400> SEQUENCE: 60
cccactggaa aaattca                                                    17

<210> SEQ ID NO 61
<211> LENGTH: 16
<212> TYPE: DNA
<213> ORGANISM: Artificial
<220> FEATURE:
<223> OTHER INFORMATION: probe

<400> SEQUENCE: 61
cccactggaa aaattc                                                     16

<210> SEQ ID NO 62
<211> LENGTH: 16
<212> TYPE: DNA
<213> ORGANISM: Artificial
<220> FEATURE:
<223> OTHER INFORMATION: probe

<400> SEQUENCE: 62
ccccgtcccc atgccc                                                     16

<210> SEQ ID NO 63
<211> LENGTH: 15
<212> TYPE: DNA
<213> ORGANISM: Artificial
<220> FEATURE:
<223> OTHER INFORMATION: probe

<400> SEQUENCE: 63
cccgtcccca tgccc                                                      15

<210> SEQ ID NO 64
<211> LENGTH: 14
<212> TYPE: DNA
<213> ORGANISM: Artificial
<220> FEATURE:
<223> OTHER INFORMATION: probe

<400> SEQUENCE: 64
ccgtccccat gccc                                                       14

<210> SEQ ID NO 65
<211> LENGTH: 13
<212> TYPE: DNA
<213> ORGANISM: Artificial
<220> FEATURE:
<223> OTHER INFORMATION: probe

<400> SEQUENCE: 65
cgtccccatg ccc                                                        13

<210> SEQ ID NO 66
<211> LENGTH: 12
<212> TYPE: DNA
<213> ORGANISM: Artificial
<220> FEATURE:
<223> OTHER INFORMATION: probe

<400> SEQUENCE: 66
gtccccatgc cc                                                         12

<210> SEQ ID NO 67
<211> LENGTH: 46
```

```
<212> TYPE: DNA
<213> ORGANISM: Artificial
<220> FEATURE:
<223> OTHER INFORMATION: primer

<400> SEQUENCE: 67
tcatcataat tctgacttct acattccaaa agccacactc aaagac                   46

<210> SEQ ID NO 68
<211> LENGTH: 45
<212> TYPE: DNA
<213> ORGANISM: Artificial
<220> FEATURE:
<223> OTHER INFORMATION: primer

<400> SEQUENCE: 68
catcataatt ctgacttcta cattccaaaa gccacactca aagac                    45

<210> SEQ ID NO 69
<211> LENGTH: 44
<212> TYPE: DNA
<213> ORGANISM: Artificial
<220> FEATURE:
<223> OTHER INFORMATION: primer

<400> SEQUENCE: 69
atcataattc tgacttctac attccaaaag ccacactcaa agac                     44

<210> SEQ ID NO 70
<211> LENGTH: 43
<212> TYPE: DNA
<213> ORGANISM: Artificial
<220> FEATURE:
<223> OTHER INFORMATION: primer

<400> SEQUENCE: 70
tcataattct gacttctaca ttccaaaagc cacactcaaa gac                      43

<210> SEQ ID NO 71
<211> LENGTH: 42
<212> TYPE: DNA
<213> ORGANISM: Artificial
<220> FEATURE:
<223> OTHER INFORMATION: primer

<400> SEQUENCE: 71
cataattctg acttctacat tccaaaagcc acactcaaag ac                       42

<210> SEQ ID NO 72
<211> LENGTH: 41
<212> TYPE: DNA
<213> ORGANISM: Artificial
<220> FEATURE:
<223> OTHER INFORMATION: primer

<400> SEQUENCE: 72
ataattctga cttctacatt ccaaaagcca cactcaaaga c                        41

<210> SEQ ID NO 73
<211> LENGTH: 40
<212> TYPE: DNA
<213> ORGANISM: Artificial
<220> FEATURE:
<223> OTHER INFORMATION: primer

<400> SEQUENCE: 73
```
taattctgac ttctacattc caaaagccac actcaaagac          40

<210> SEQ ID NO 74
<211> LENGTH: 39
<212> TYPE: DNA
<213> ORGANISM: Artificial
<220> FEATURE:
<223> OTHER INFORMATION: primer

<400> SEQUENCE: 74
aattctgact tctacattcc aaaagccaca ctcaaagac          39

<210> SEQ ID NO 75
<211> LENGTH: 38
<212> TYPE: DNA
<213> ORGANISM: Artificial
<220> FEATURE:
<223> OTHER INFORMATION: primer

<400> SEQUENCE: 75
attctgactt ctacattcca aaagccacac tcaaagac          38

<210> SEQ ID NO 76
<211> LENGTH: 37
<212> TYPE: DNA
<213> ORGANISM: Artificial
<220> FEATURE:
<223> OTHER INFORMATION: primer

<400> SEQUENCE: 76
ttctgacttc tacattccaa agccacact caaagac          37

<210> SEQ ID NO 77
<211> LENGTH: 36
<212> TYPE: DNA
<213> ORGANISM: Artificial
<220> FEATURE:
<223> OTHER INFORMATION: primer

<400> SEQUENCE: 77
tctgacttct acattccaaa agccacactc aaagac          36

<210> SEQ ID NO 78
<211> LENGTH: 35
<212> TYPE: DNA
<213> ORGANISM: Artificial
<220> FEATURE:
<223> OTHER INFORMATION: primer

<400> SEQUENCE: 78
ctgacttcta cattccaaaa gccacactca aagac          35

<210> SEQ ID NO 79
<211> LENGTH: 34
<212> TYPE: DNA
<213> ORGANISM: Artificial
<220> FEATURE:
<223> OTHER INFORMATION: primer

<400> SEQUENCE: 79
tgacttctac attccaaaag ccacactcaa agac          34

<210> SEQ ID NO 80
<211> LENGTH: 33
<212> TYPE: DNA
<213> ORGANISM: Artificial

<220> FEATURE:
<223> OTHER INFORMATION: primer

<400> SEQUENCE: 80
gacttctaca ttccaaaagc cacactcaaa gac                33

<210> SEQ ID NO 81
<211> LENGTH: 32
<212> TYPE: DNA
<213> ORGANISM: Artificial
<220> FEATURE:
<223> OTHER INFORMATION: primer

<400> SEQUENCE: 81
acttctacat tccaaaagcc acactcaaag ac                 32

<210> SEQ ID NO 82
<211> LENGTH: 31
<212> TYPE: DNA
<213> ORGANISM: Artificial
<220> FEATURE:
<223> OTHER INFORMATION: primer

<400> SEQUENCE: 82
cttctacatt ccaaaagcca cactcaaaga c                  31

<210> SEQ ID NO 83
<211> LENGTH: 30
<212> TYPE: DNA
<213> ORGANISM: Artificial
<220> FEATURE:
<223> OTHER INFORMATION: primer

<400> SEQUENCE: 83
ttctacattc caaaagccac actcaaagac                    30

<210> SEQ ID NO 84
<211> LENGTH: 29
<212> TYPE: DNA
<213> ORGANISM: Artificial
<220> FEATURE:
<223> OTHER INFORMATION: primer

<400> SEQUENCE: 84
tctacattcc aaaagccaca ctcaaagac                     29

<210> SEQ ID NO 85
<211> LENGTH: 28
<212> TYPE: DNA
<213> ORGANISM: Artificial
<220> FEATURE:
<223> OTHER INFORMATION: primer

<400> SEQUENCE: 85
ctacattcca aaagccacac tcaaagac                      28

<210> SEQ ID NO 86
<211> LENGTH: 27
<212> TYPE: DNA
<213> ORGANISM: Artificial
<220> FEATURE:
<223> OTHER INFORMATION: primer

<400> SEQUENCE: 86
tacattccaa aagccacact caaagac                       27

<210> SEQ ID NO 87
<211> LENGTH: 39
<212> TYPE: DNA
<213> ORGANISM: Artificial
<220> FEATURE:
<223> OTHER INFORMATION: primer

<400> SEQUENCE: 87
aatcaggaat ctcctcccaa ctcaacttcc cagtgtgat                    39

<210> SEQ ID NO 88
<211> LENGTH: 38
<212> TYPE: DNA
<213> ORGANISM: Artificial
<220> FEATURE:
<223> OTHER INFORMATION: primer

<400> SEQUENCE: 88
atcaggaatc tcctcccaac tcaacttccc agtgtgat                     38

<210> SEQ ID NO 89
<211> LENGTH: 37
<212> TYPE: DNA
<213> ORGANISM: Artificial
<220> FEATURE:
<223> OTHER INFORMATION: primer

<400> SEQUENCE: 89
tcaggaatct cctcccaact caacttccca gtgtgat                      37

<210> SEQ ID NO 90
<211> LENGTH: 36
<212> TYPE: DNA
<213> ORGANISM: Artificial
<220> FEATURE:
<223> OTHER INFORMATION: primer

<400> SEQUENCE: 90
caggaatctc ctcccaactc aacttcccag tgtgat                       36

<210> SEQ ID NO 91
<211> LENGTH: 35
<212> TYPE: DNA
<213> ORGANISM: Artificial
<220> FEATURE:
<223> OTHER INFORMATION: primer

<400> SEQUENCE: 91
aggaatctcc tcccaactca acttcccagt gtgat                        35

<210> SEQ ID NO 92
<211> LENGTH: 34
<212> TYPE: DNA
<213> ORGANISM: Artificial
<220> FEATURE:
<223> OTHER INFORMATION: primer

<400> SEQUENCE: 92
ggaatctcct cccaactcaa cttcccagtg tgat                         34

<210> SEQ ID NO 93
<211> LENGTH: 33
<212> TYPE: DNA
<213> ORGANISM: Artificial
<220> FEATURE:
<223> OTHER INFORMATION: primer

<400> SEQUENCE: 93
gaatctcctc ccaactcaac ttcccagtgt gat        33

<210> SEQ ID NO 94
<211> LENGTH: 32
<212> TYPE: DNA
<213> ORGANISM: Artificial
<220> FEATURE:
<223> OTHER INFORMATION: primer

<400> SEQUENCE: 94
aatctcctcc caactcaact tcccagtgtg at        32

<210> SEQ ID NO 95
<211> LENGTH: 31
<212> TYPE: DNA
<213> ORGANISM: Artificial
<220> FEATURE:
<223> OTHER INFORMATION: primer

<400> SEQUENCE: 95
atctcctccc aactcaactt cccagtgtga t        31

<210> SEQ ID NO 96
<211> LENGTH: 30
<212> TYPE: DNA
<213> ORGANISM: Artificial
<220> FEATURE:
<223> OTHER INFORMATION: primer

<400> SEQUENCE: 96
tctcctccca actcaacttc ccagtgtgat        30

<210> SEQ ID NO 97
<211> LENGTH: 29
<212> TYPE: DNA
<213> ORGANISM: Artificial
<220> FEATURE:
<223> OTHER INFORMATION: primer

<400> SEQUENCE: 97
ctcctcccaa ctcaacttcc cagtgtgat        29

<210> SEQ ID NO 98
<211> LENGTH: 28
<212> TYPE: DNA
<213> ORGANISM: Artificial
<220> FEATURE:
<223> OTHER INFORMATION: primer

<400> SEQUENCE: 98
tcctcccaac tcaacttccc agtgtgat        28

<210> SEQ ID NO 99
<211> LENGTH: 27
<212> TYPE: DNA
<213> ORGANISM: Artificial
<220> FEATURE:
<223> OTHER INFORMATION: primer

<400> SEQUENCE: 99
cctcccaact caacttccca gtgtgat        27

<210> SEQ ID NO 100

```
<211> LENGTH: 26
<212> TYPE: DNA
<213> ORGANISM: Artificial
<220> FEATURE:
<223> OTHER INFORMATION: primer

<400> SEQUENCE: 100
ctcccaactc aacttcccag tgtgat                                              26

<210> SEQ ID NO 101
<211> LENGTH: 25
<212> TYPE: DNA
<213> ORGANISM: Artificial
<220> FEATURE:
<223> OTHER INFORMATION: primer

<400> SEQUENCE: 101
tcccaactca acttcccagt gtgat                                               25

<210> SEQ ID NO 102
<211> LENGTH: 24
<212> TYPE: DNA
<213> ORGANISM: Artificial
<220> FEATURE:
<223> OTHER INFORMATION: primer

<400> SEQUENCE: 102
cccaactcaa cttcccagtg tgat                                                24

<210> SEQ ID NO 103
<211> LENGTH: 23
<212> TYPE: DNA
<213> ORGANISM: Artificial
<220> FEATURE:
<223> OTHER INFORMATION: primer

<400> SEQUENCE: 103
ccaactcaac ttcccagtgt gat                                                 23

<210> SEQ ID NO 104
<211> LENGTH: 48
<212> TYPE: DNA
<213> ORGANISM: Artificial
<220> FEATURE:
<223> OTHER INFORMATION: primer

<400> SEQUENCE: 104
cctctggtca aggtcacatt cttccagaat ggaaaatccc agaaattc                      48

<210> SEQ ID NO 105
<211> LENGTH: 47
<212> TYPE: DNA
<213> ORGANISM: Artificial
<220> FEATURE:
<223> OTHER INFORMATION: primer

<400> SEQUENCE: 105
ctctggtcaa ggtcacattc ttccagaatg gaaaatccca gaaattc                       47

<210> SEQ ID NO 106
<211> LENGTH: 46
<212> TYPE: DNA
<213> ORGANISM: Artificial
<220> FEATURE:
<223> OTHER INFORMATION: primer

<400> SEQUENCE: 106
```
tctggtcaag gtcacattct tccagaatgg aaaatcccag aaattc                46

<210> SEQ ID NO 107
<211> LENGTH: 45
<212> TYPE: DNA
<213> ORGANISM: Artificial
<220> FEATURE:
<223> OTHER INFORMATION: primer

<400> SEQUENCE: 107
ctggtcaagg tcacattctt ccagaatgga aatcccaga aattc                  45

<210> SEQ ID NO 108
<211> LENGTH: 44
<212> TYPE: DNA
<213> ORGANISM: Artificial
<220> FEATURE:
<223> OTHER INFORMATION: primer

<400> SEQUENCE: 108
tggtcaaggt cacattcttc cagaatggaa atcccagaa attc                   44

<210> SEQ ID NO 109
<211> LENGTH: 43
<212> TYPE: DNA
<213> ORGANISM: Artificial
<220> FEATURE:
<223> OTHER INFORMATION: primer

<400> SEQUENCE: 109
ggtcaaggtc acattcttcc agaatggaaa atcccagaaa ttc                   43

<210> SEQ ID NO 110
<211> LENGTH: 42
<212> TYPE: DNA
<213> ORGANISM: Artificial
<220> FEATURE:
<223> OTHER INFORMATION: primer

<400> SEQUENCE: 110
gtcaaggtca cattcttcca gaatggaaaa tcccagaaat tc                    42

<210> SEQ ID NO 111
<211> LENGTH: 41
<212> TYPE: DNA
<213> ORGANISM: Artificial
<220> FEATURE:
<223> OTHER INFORMATION: primer

<400> SEQUENCE: 111
tcaaggtcac attcttccag aatggaaaat cccagaaatt c                     41

<210> SEQ ID NO 112
<211> LENGTH: 40
<212> TYPE: DNA
<213> ORGANISM: Artificial
<220> FEATURE:
<223> OTHER INFORMATION: primer

<400> SEQUENCE: 112
caaggtcaca ttcttccaga atggaaaatc ccagaaattc                       40

<210> SEQ ID NO 113
<211> LENGTH: 39
<212> TYPE: DNA

<213> ORGANISM: Artificial
<220> FEATURE:
<223> OTHER INFORMATION: primer

<400> SEQUENCE: 113
aaggtcacat tcttccagaa tggaaaatcc cagaaattc        39

<210> SEQ ID NO 114
<211> LENGTH: 38
<212> TYPE: DNA
<213> ORGANISM: Artificial
<220> FEATURE:
<223> OTHER INFORMATION: primer

<400> SEQUENCE: 114
aggtcacatt cttccagaat ggaaaatccc agaaattc         38

<210> SEQ ID NO 115
<211> LENGTH: 37
<212> TYPE: DNA
<213> ORGANISM: Artificial
<220> FEATURE:
<223> OTHER INFORMATION: primer

<400> SEQUENCE: 115
ggtcacattc ttccagaatg gaaaatccca gaaattc          37

<210> SEQ ID NO 116
<211> LENGTH: 36
<212> TYPE: DNA
<213> ORGANISM: Artificial
<220> FEATURE:
<223> OTHER INFORMATION: primer

<400> SEQUENCE: 116
gtcacattct tccagaatgg aaaatcccag aaattc           36

<210> SEQ ID NO 117
<211> LENGTH: 35
<212> TYPE: DNA
<213> ORGANISM: Artificial
<220> FEATURE:
<223> OTHER INFORMATION: primer

<400> SEQUENCE: 117
tcacattctt ccagaatgga aatcccaga aattc             35

<210> SEQ ID NO 118
<211> LENGTH: 34
<212> TYPE: DNA
<213> ORGANISM: Artificial
<220> FEATURE:
<223> OTHER INFORMATION: primer

<400> SEQUENCE: 118
cacattcttc cagaatggaa atcccagaa attc              34

<210> SEQ ID NO 119
<211> LENGTH: 33
<212> TYPE: DNA
<213> ORGANISM: Artificial
<220> FEATURE:
<223> OTHER INFORMATION: primer

<400> SEQUENCE: 119
acattcttcc agaatggaaa atcccagaaa ttc              33

<210> SEQ ID NO 120
<211> LENGTH: 32
<212> TYPE: DNA
<213> ORGANISM: Artificial
<220> FEATURE:
<223> OTHER INFORMATION: primer

<400> SEQUENCE: 120
cattcttcca gaatggaaaa tcccagaaat tc                32

<210> SEQ ID NO 121
<211> LENGTH: 31
<212> TYPE: DNA
<213> ORGANISM: Artificial
<220> FEATURE:
<223> OTHER INFORMATION: primer

<400> SEQUENCE: 121
attcttccag aatggaaaat cccagaaatt c                 31

<210> SEQ ID NO 122
<211> LENGTH: 38
<212> TYPE: DNA
<213> ORGANISM: Artificial
<220> FEATURE:
<223> OTHER INFORMATION: primer

<400> SEQUENCE: 122
accactgtga ctgtggtttg cttgtgggat ggagaagg         38

<210> SEQ ID NO 123
<211> LENGTH: 37
<212> TYPE: DNA
<213> ORGANISM: Artificial
<220> FEATURE:
<223> OTHER INFORMATION: primer

<400> SEQUENCE: 123
ccactgtgac tgtggtttgc ttgtgggatg gagaagg          37

<210> SEQ ID NO 124
<211> LENGTH: 36
<212> TYPE: DNA
<213> ORGANISM: Artificial
<220> FEATURE:
<223> OTHER INFORMATION: primer

<400> SEQUENCE: 124
cactgtgact gtggtttgct tgtgggatgg agaagg           36

<210> SEQ ID NO 125
<211> LENGTH: 35
<212> TYPE: DNA
<213> ORGANISM: Artificial
<220> FEATURE:
<223> OTHER INFORMATION: primer

<400> SEQUENCE: 125
actgtgactg tggtttgctt gtgggatgga gaagg            35

<210> SEQ ID NO 126
<211> LENGTH: 34
<212> TYPE: DNA
<213> ORGANISM: Artificial
<220> FEATURE:

```
<223> OTHER INFORMATION: primer

<400> SEQUENCE: 126
ctgtgactgt ggtttgcttg tgggatggag aagg                                34

<210> SEQ ID NO 127
<211> LENGTH: 33
<212> TYPE: DNA
<213> ORGANISM: Artificial
<220> FEATURE:
<223> OTHER INFORMATION: primer

<400> SEQUENCE: 127
tgtgactgtg gtttgcttgt gggatggaga agg                                 33

<210> SEQ ID NO 128
<211> LENGTH: 32
<212> TYPE: DNA
<213> ORGANISM: Artificial
<220> FEATURE:
<223> OTHER INFORMATION: primer

<400> SEQUENCE: 128
gtgactgtgg tttgcttgtg ggatggagaa gg                                  32

<210> SEQ ID NO 129
<211> LENGTH: 31
<212> TYPE: DNA
<213> ORGANISM: Artificial
<220> FEATURE:
<223> OTHER INFORMATION: primer

<400> SEQUENCE: 129
tgactgtggt ttgcttgtgg gatggagaag g                                   31

<210> SEQ ID NO 130
<211> LENGTH: 30
<212> TYPE: DNA
<213> ORGANISM: Artificial
<220> FEATURE:
<223> OTHER INFORMATION: primer

<400> SEQUENCE: 130
gactgtggtt tgcttgtggg atggagaagg                                     30

<210> SEQ ID NO 131
<211> LENGTH: 29
<212> TYPE: DNA
<213> ORGANISM: Artificial
<220> FEATURE:
<223> OTHER INFORMATION: primer

<400> SEQUENCE: 131
actgtggttt gcttgtggga tggagaagg                                      29

<210> SEQ ID NO 132
<211> LENGTH: 28
<212> TYPE: DNA
<213> ORGANISM: Artificial
<220> FEATURE:
<223> OTHER INFORMATION: primer

<400> SEQUENCE: 132
ctgtggtttg cttgtgggat ggagaagg                                       28
```

```
<210> SEQ ID NO 133
<211> LENGTH: 27
<212> TYPE: DNA
<213> ORGANISM: Artificial
<220> FEATURE:
<223> OTHER INFORMATION: primer

<400> SEQUENCE: 133
tgtggtttgc ttgtgggatg gagaagg                                              27

<210> SEQ ID NO 134
<211> LENGTH: 26
<212> TYPE: DNA
<213> ORGANISM: Artificial
<220> FEATURE:
<223> OTHER INFORMATION: primer

<400> SEQUENCE: 134
gtggtttgct tgtgggatgg agaagg                                               26

<210> SEQ ID NO 135
<211> LENGTH: 25
<212> TYPE: DNA
<213> ORGANISM: Artificial
<220> FEATURE:
<223> OTHER INFORMATION: primer

<400> SEQUENCE: 135
tggtttgctt gtgggatgga gaagg                                                25

<210> SEQ ID NO 136
<211> LENGTH: 24
<212> TYPE: DNA
<213> ORGANISM: Artificial
<220> FEATURE:
<223> OTHER INFORMATION: primer

<400> SEQUENCE: 136
ggtttgcttg tgggatggag aagg                                                 24

<210> SEQ ID NO 137
<211> LENGTH: 23
<212> TYPE: DNA
<213> ORGANISM: Artificial
<220> FEATURE:
<223> OTHER INFORMATION: primer

<400> SEQUENCE: 137
gtttgcttgt gggatggaga agg                                                  23

<210> SEQ ID NO 138
<211> LENGTH: 40
<212> TYPE: DNA
<213> ORGANISM: Artificial
<220> FEATURE:
<223> OTHER INFORMATION: primer

<400> SEQUENCE: 138
atgaaatcgg ggtaaaggag cctggaacac atcctgtgac                                40

<210> SEQ ID NO 139
<211> LENGTH: 39
<212> TYPE: DNA
<213> ORGANISM: Artificial
<220> FEATURE:
<223> OTHER INFORMATION: primer
```

<400> SEQUENCE: 139
tgaaatcggg gtaaaggagc ctggaacaca tcctgtgac        39

<210> SEQ ID NO 140
<211> LENGTH: 38
<212> TYPE: DNA
<213> ORGANISM: Artificial
<220> FEATURE:
<223> OTHER INFORMATION: primer

<400> SEQUENCE: 140
gaaatcgggg taaaggagcc tggaacacat cctgtgac         38

<210> SEQ ID NO 141
<211> LENGTH: 37
<212> TYPE: DNA
<213> ORGANISM: Artificial
<220> FEATURE:
<223> OTHER INFORMATION: primer

<400> SEQUENCE: 141 aaatcgggt aaaggagcct ggaacacatc ctgtgac           37

<210> SEQ ID NO 142
<211> LENGTH: 36
<212> TYPE: DNA
<213> ORGANISM: Artificial
<220> FEATURE:
<223> OTHER INFORMATION: primer

<400> SEQUENCE: 142 aatcgggta aaggagcctg gaacacatcc tgtgac            36

<210> SEQ ID NO 143
<211> LENGTH: 35
<212> TYPE: DNA
<213> ORGANISM: Artificial
<220> FEATURE:
<223> OTHER INFORMATION: primer

<400> SEQUENCE: 143 atcgggtaa aggagcctgg aacacatcct gtgac             35

<210> SEQ ID NO 144
<211> LENGTH: 34
<212> TYPE: DNA
<213> ORGANISM: Artificial
<220> FEATURE:
<223> OTHER INFORMATION: primer

<400> SEQUENCE: 144
tcggggtaaa ggagcctgga acacatcctg tgac             34

<210> SEQ ID NO 145
<211> LENGTH: 33
<212> TYPE: DNA
<213> ORGANISM: Artificial
<220> FEATURE:
<223> OTHER INFORMATION: primer

<400> SEQUENCE: 145
cggggtaaag gagcctggaa cacatcctgt gac              33

<210> SEQ ID NO 146
<211> LENGTH: 32

```
<212> TYPE: DNA
<213> ORGANISM: Artificial
<220> FEATURE:
<223> OTHER INFORMATION: primer

<400> SEQUENCE: 146
ggggtaaagg agcctggaac acatcctgtg ac                              32

<210> SEQ ID NO 147
<211> LENGTH: 31
<212> TYPE: DNA
<213> ORGANISM: Artificial
<220> FEATURE:
<223> OTHER INFORMATION: primer

<400> SEQUENCE: 147
gggtaaagga gcctggaaca catcctgtga c                               31

<210> SEQ ID NO 148
<211> LENGTH: 30
<212> TYPE: DNA
<213> ORGANISM: Artificial
<220> FEATURE:
<223> OTHER INFORMATION: primer

<400> SEQUENCE: 148
ggtaaaggag cctggaacac atcctgtgac                                 30

<210> SEQ ID NO 149
<211> LENGTH: 29
<212> TYPE: DNA
<213> ORGANISM: Artificial
<220> FEATURE:
<223> OTHER INFORMATION: primer

<400> SEQUENCE: 149
gtaaaggagc ctggaacaca tcctgtgac                                  29

<210> SEQ ID NO 150
<211> LENGTH: 28
<212> TYPE: DNA
<213> ORGANISM: Artificial
<220> FEATURE:
<223> OTHER INFORMATION: primer

<400> SEQUENCE: 150
taaaggagcc tggaacacat cctgtgac                                   28

<210> SEQ ID NO 151
<211> LENGTH: 27
<212> TYPE: DNA
<213> ORGANISM: Artificial
<220> FEATURE:
<223> OTHER INFORMATION: primer

<400> SEQUENCE: 151
aaaggagcct ggaacacatc ctgtgac                                    27

<210> SEQ ID NO 152
<211> LENGTH: 26
<212> TYPE: DNA
<213> ORGANISM: Artificial
<220> FEATURE:
<223> OTHER INFORMATION: primer

<400> SEQUENCE: 152
```

```
aaggagcctg gaacacatcc tgtgac                                            26

<210> SEQ ID NO 153
<211> LENGTH: 25
<212> TYPE: DNA
<213> ORGANISM: Artificial
<220> FEATURE:
<223> OTHER INFORMATION: primer

<400> SEQUENCE: 153
aggagcctgg aacacatcct gtgac                                             25

<210> SEQ ID NO 154
<211> LENGTH: 25
<212> TYPE: DNA
<213> ORGANISM: Artificial
<220> FEATURE:
<223> OTHER INFORMATION: primer

<400> SEQUENCE: 154
aggagcctgg aacacatcct gtgac                                             25

<210> SEQ ID NO 155
<211> LENGTH: 24
<212> TYPE: DNA
<213> ORGANISM: Artificial
<220> FEATURE:
<223> OTHER INFORMATION: primer

<400> SEQUENCE: 155
ggagcctgga acacatcctg tgac                                              24

<210> SEQ ID NO 156
<211> LENGTH: 23
<212> TYPE: DNA
<213> ORGANISM: Artificial
<220> FEATURE:
<223> OTHER INFORMATION: primer

<400> SEQUENCE: 156
gagcctggaa cacatcctgt gac                                               23

<210> SEQ ID NO 157
<211> LENGTH: 41
<212> TYPE: DNA
<213> ORGANISM: Artificial
<220> FEATURE:
<223> OTHER INFORMATION: primer

<400> SEQUENCE: 157
gttcccaagc agcccttcca ttttactttc cagagactgg c                           41

<210> SEQ ID NO 158
<211> LENGTH: 40
<212> TYPE: DNA
<213> ORGANISM: Artificial
<220> FEATURE:
<223> OTHER INFORMATION: primer

<400> SEQUENCE: 158
ttcccaagca gcccttccat tttactttcc agagactggc                             40

<210> SEQ ID NO 159
<211> LENGTH: 39
<212> TYPE: DNA
<213> ORGANISM: Artificial
```

```
<220> FEATURE:
<223> OTHER INFORMATION: primer

<400> SEQUENCE: 159
tcccaagcag cccttccatt ttactttcca gagactggc                              39

<210> SEQ ID NO 160
<211> LENGTH: 38
<212> TYPE: DNA
<213> ORGANISM: Artificial
<220> FEATURE:
<223> OTHER INFORMATION: primer

<400> SEQUENCE: 160
cccaagcagc ccttccattt tactttccag agactggc                               38

<210> SEQ ID NO 161
<211> LENGTH: 37
<212> TYPE: DNA
<213> ORGANISM: Artificial
<220> FEATURE:
<223> OTHER INFORMATION: primer

<400> SEQUENCE: 161
ccaagcagcc cttccatttt actttccaga gactggc                                37

<210> SEQ ID NO 162
<211> LENGTH: 36
<212> TYPE: DNA
<213> ORGANISM: Artificial
<220> FEATURE:
<223> OTHER INFORMATION: primer

<400> SEQUENCE: 162
caagcagccc ttccatttta ctttccagag actggc                                 36

<210> SEQ ID NO 163
<211> LENGTH: 35
<212> TYPE: DNA
<213> ORGANISM: Artificial
<220> FEATURE:
<223> OTHER INFORMATION: primer

<400> SEQUENCE: 163
aagcagccct tccattttac tttccagaga ctggc                                  35

<210> SEQ ID NO 164
<211> LENGTH: 34
<212> TYPE: DNA
<213> ORGANISM: Artificial
<220> FEATURE:
<223> OTHER INFORMATION: primer

<400> SEQUENCE: 164
agcagccctt ccattttact ttccagagac tggc                                   34

<210> SEQ ID NO 165
<211> LENGTH: 33
<212> TYPE: DNA
<213> ORGANISM: Artificial
<220> FEATURE:
<223> OTHER INFORMATION: primer

<400> SEQUENCE: 165
gcagcccttc catttttactt tccagagact ggc                                   33
```

<210> SEQ ID NO 166
<211> LENGTH: 32
<212> TYPE: DNA
<213> ORGANISM: Artificial
<220> FEATURE:
<223> OTHER INFORMATION: primer

<400> SEQUENCE: 166
cagcccttcc attttacttt ccagagactg gc                                    32

<210> SEQ ID NO 167
<211> LENGTH: 31
<212> TYPE: DNA
<213> ORGANISM: Artificial
<220> FEATURE:
<223> OTHER INFORMATION: primer

<400> SEQUENCE: 167
agcccttcca ttttactttc cagagactgg c                                     31

<210> SEQ ID NO 168
<211> LENGTH: 30
<212> TYPE: DNA
<213> ORGANISM: Artificial
<220> FEATURE:
<223> OTHER INFORMATION: primer

<400> SEQUENCE: 168
gcccttccat tttactttcc agagactggc                                       30

<210> SEQ ID NO 169
<211> LENGTH: 29
<212> TYPE: DNA
<213> ORGANISM: Artificial
<220> FEATURE:
<223> OTHER INFORMATION: primer

<400> SEQUENCE: 169
cccttccatt ttactttcca gagactggc                                        29

<210> SEQ ID NO 170
<211> LENGTH: 28
<212> TYPE: DNA
<213> ORGANISM: Artificial
<220> FEATURE:
<223> OTHER INFORMATION: primer

<400> SEQUENCE: 170
ccttccattt tactttccag agactggc                                         28

<210> SEQ ID NO 171
<211> LENGTH: 27
<212> TYPE: DNA
<213> ORGANISM: Artificial
<220> FEATURE:
<223> OTHER INFORMATION: primer

<400> SEQUENCE: 171
cttccatttt actttccaga gactggc                                          27

<210> SEQ ID NO 172
<211> LENGTH: 39
<212> TYPE: DNA
<213> ORGANISM: Artificial
<220> FEATURE:
<223> OTHER INFORMATION: primer

<400> SEQUENCE: 172
tcattctatg tgctggagat ggtgtacagt agggtgagg         39

<210> SEQ ID NO 173
<211> LENGTH: 38
<212> TYPE: DNA
<213> ORGANISM: Artificial
<220> FEATURE:
<223> OTHER INFORMATION: primer

<400> SEQUENCE: 173
cattctatgt gctggagatg gtgtacagta gggtgagg          38

<210> SEQ ID NO 174
<211> LENGTH: 37
<212> TYPE: DNA
<213> ORGANISM: Artificial
<220> FEATURE:
<223> OTHER INFORMATION: primer

<400> SEQUENCE: 174
attctatgtg ctggagatgg tgtacagtag ggtgagg           37

<210> SEQ ID NO 175
<211> LENGTH: 36
<212> TYPE: DNA
<213> ORGANISM: Artificial
<220> FEATURE:
<223> OTHER INFORMATION: primer

<400> SEQUENCE: 175
ttctatgtgc tggagatggt gtacagtagg gtgagg            36

<210> SEQ ID NO 176
<211> LENGTH: 35
<212> TYPE: DNA
<213> ORGANISM: Artificial
<220> FEATURE:
<223> OTHER INFORMATION: primer

<400> SEQUENCE: 176
tctatgtgct ggagatggtg tacagtaggg tgagg             35

<210> SEQ ID NO 177
<211> LENGTH: 34
<212> TYPE: DNA
<213> ORGANISM: Artificial
<220> FEATURE:
<223> OTHER INFORMATION: primer

<400> SEQUENCE: 177
ctatgtgctg gagatggtgt acagtagggt gagg              34

<210> SEQ ID NO 178
<211> LENGTH: 33
<212> TYPE: DNA
<213> ORGANISM: Artificial
<220> FEATURE:
<223> OTHER INFORMATION: primer

<400> SEQUENCE: 178
tatgtgctgg agatggtgta cagtagggtg agg               33

<210> SEQ ID NO 179

```
<211> LENGTH: 32
<212> TYPE: DNA
<213> ORGANISM: Artificial
<220> FEATURE:
<223> OTHER INFORMATION: primer

<400> SEQUENCE: 179
atgtgctgga gatggtgtac agtagggtga gg                                32

<210> SEQ ID NO 180
<211> LENGTH: 31
<212> TYPE: DNA
<213> ORGANISM: Artificial
<220> FEATURE:
<223> OTHER INFORMATION: primer

<400> SEQUENCE: 180
tgtgctggag atggtgtaca gtagggtgag g                                 31

<210> SEQ ID NO 181
<211> LENGTH: 30
<212> TYPE: DNA
<213> ORGANISM: Artificial
<220> FEATURE:
<223> OTHER INFORMATION: primer

<400> SEQUENCE: 181
gtgctggaga tggtgtacag tagggtgagg                                   30

<210> SEQ ID NO 182
<211> LENGTH: 29
<212> TYPE: DNA
<213> ORGANISM: Artificial
<220> FEATURE:
<223> OTHER INFORMATION: primer

<400> SEQUENCE: 182
tgctggagat ggtgtacagt agggtgagg                                    29

<210> SEQ ID NO 183
<211> LENGTH: 28
<212> TYPE: DNA
<213> ORGANISM: Artificial
<220> FEATURE:
<223> OTHER INFORMATION: primer

<400> SEQUENCE: 183
gctggagatg gtgtacagta gggtgagg                                     28

<210> SEQ ID NO 184
<211> LENGTH: 27
<212> TYPE: DNA
<213> ORGANISM: Artificial
<220> FEATURE:
<223> OTHER INFORMATION: primer

<400> SEQUENCE: 184
ctggagatgg tgtacagtag ggtgagg                                      27

<210> SEQ ID NO 185
<211> LENGTH: 26
<212> TYPE: DNA
<213> ORGANISM: Artificial
<220> FEATURE:
<223> OTHER INFORMATION: primer

<400> SEQUENCE: 185
```

-continued tggagatggt gtacagtagg gtgagg                                    26

<210> SEQ ID NO 186
<211> LENGTH: 25
<212> TYPE: DNA
<213> ORGANISM: Artificial
<220> FEATURE:
<223> OTHER INFORMATION: primer

<400> SEQUENCE: 186
ggagatggtg tacagtaggg tgagg                                     25

<210> SEQ ID NO 187
<211> LENGTH: 24
<212> TYPE: DNA
<213> ORGANISM: Artificial
<220> FEATURE:
<223> OTHER INFORMATION: primer

<400> SEQUENCE: 187
gagatggtgt acagtagggt gagg                                      24

<210> SEQ ID NO 188
<211> LENGTH: 46
<212> TYPE: DNA
<213> ORGANISM: Artificial
<220> FEATURE:
<223> OTHER INFORMATION: primer

<400> SEQUENCE: 188
aggtagtgct caccatgacc cctaccgtct ctattttata gtgagc              46

<210> SEQ ID NO 189
<211> LENGTH: 45
<212> TYPE: DNA
<213> ORGANISM: Artificial
<220> FEATURE:
<223> OTHER INFORMATION: primer

<400> SEQUENCE: 189
ggtagtgctc accatgaccc ctaccgtctc tattttatag tgagc               45

<210> SEQ ID NO 190
<211> LENGTH: 44
<212> TYPE: DNA
<213> ORGANISM: Artificial
<220> FEATURE:
<223> OTHER INFORMATION: primer

<400> SEQUENCE: 190
gtagtgctca ccatgacccc taccgtctct attttatagt gagc                44

<210> SEQ ID NO 191
<211> LENGTH: 43
<212> TYPE: DNA
<213> ORGANISM: Artificial
<220> FEATURE:
<223> OTHER INFORMATION: primer

<400> SEQUENCE: 191
tagtgctcac catgacccct accgtctcta ttttatagtg agc                 43

<210> SEQ ID NO 192
<211> LENGTH: 42
<212> TYPE: DNA

```
<213> ORGANISM: Artificial
<220> FEATURE:
<223> OTHER INFORMATION: primer

<400> SEQUENCE: 192
agtgctcacc atgacccta ccgtctctat tttatagtga gc                    42

<210> SEQ ID NO 193
<211> LENGTH: 41
<212> TYPE: DNA
<213> ORGANISM: Artificial
<220> FEATURE:
<223> OTHER INFORMATION: primer

<400> SEQUENCE: 193
gtgctcacca tgacccctac cgtctctatt ttatagtgag c                     41

<210> SEQ ID NO 194
<211> LENGTH: 40
<212> TYPE: DNA
<213> ORGANISM: Artificial
<220> FEATURE:
<223> OTHER INFORMATION: primer

<400> SEQUENCE: 194
tgctcaccat gaccccctacc gtctctattt tatagtgagc                       40

<210> SEQ ID NO 195
<211> LENGTH: 39
<212> TYPE: DNA
<213> ORGANISM: Artificial
<220> FEATURE:
<223> OTHER INFORMATION: primer

<400> SEQUENCE: 195
gctcaccatg accctaccg tctctatttt atagtgagc                         39

<210> SEQ ID NO 196
<211> LENGTH: 38
<212> TYPE: DNA
<213> ORGANISM: Artificial
<220> FEATURE:
<223> OTHER INFORMATION: primer

<400> SEQUENCE: 196
ctcaccatga ccctaccgt ctctatttta tagtgagc                          38

<210> SEQ ID NO 197
<211> LENGTH: 37
<212> TYPE: DNA
<213> ORGANISM: Artificial
<220> FEATURE:
<223> OTHER INFORMATION: primer

<400> SEQUENCE: 197
tcaccatgac cctaccgtc tctattttat agtgagc                           37

<210> SEQ ID NO 198
<211> LENGTH: 36
<212> TYPE: DNA
<213> ORGANISM: Artificial
<220> FEATURE:
<223> OTHER INFORMATION: primer

<400> SEQUENCE: 198
caccatgacc ctaccgtct ctattttata gtgagc                            36
```

```
<210> SEQ ID NO 199
<211> LENGTH: 35
<212> TYPE: DNA
<213> ORGANISM: Artificial
<220> FEATURE:
<223> OTHER INFORMATION: primer

<400> SEQUENCE: 199
accatgaccc ctaccgtctc tattttatag tgagc                                35

<210> SEQ ID NO 200
<211> LENGTH: 34
<212> TYPE: DNA
<213> ORGANISM: Artificial
<220> FEATURE:
<223> OTHER INFORMATION: primer

<400> SEQUENCE: 200
ccatgacccc taccgtctct attttatagt gagc                                 34

<210> SEQ ID NO 201
<211> LENGTH: 33
<212> TYPE: DNA
<213> ORGANISM: Artificial
<220> FEATURE:
<223> OTHER INFORMATION: primer

<400> SEQUENCE: 201
catgacccct accgtctcta ttttatagtg agc                                  33

<210> SEQ ID NO 202
<211> LENGTH: 32
<212> TYPE: DNA
<213> ORGANISM: Artificial
<220> FEATURE:
<223> OTHER INFORMATION: primer

<400> SEQUENCE: 202 atgacccta ccgtctctat tttatagtga gc                                    32

<210> SEQ ID NO 203
<211> LENGTH: 31
<212> TYPE: DNA
<213> ORGANISM: Artificial
<220> FEATURE:
<223> OTHER INFORMATION: primer

<400> SEQUENCE: 203 tgaccccta cgtctctatt ttatagtgag c                                     31

<210> SEQ ID NO 204
<211> LENGTH: 30
<212> TYPE: DNA
<213> ORGANISM: Artificial
<220> FEATURE:
<223> OTHER INFORMATION: primer

<400> SEQUENCE: 204 gaccctacc gtctctattt tatagtgagc                                       30

<210> SEQ ID NO 205
<211> LENGTH: 29
<212> TYPE: DNA
<213> ORGANISM: Artificial
<220> FEATURE:
```

```
<223> OTHER INFORMATION: primer

<400> SEQUENCE: 205 accccctaccg tctctatttt atagtgagc                                    29

<210> SEQ ID NO 206
<211> LENGTH: 32
<212> TYPE: DNA
<213> ORGANISM: Artificial
<220> FEATURE:
<223> OTHER INFORMATION: primer

<400> SEQUENCE: 206
ctcctcgccg caacccaact ggctctcctt ac                                 32

<210> SEQ ID NO 207
<211> LENGTH: 31
<212> TYPE: DNA
<213> ORGANISM: Artificial
<220> FEATURE:
<223> OTHER INFORMATION: primer

<400> SEQUENCE: 207
tcctcgccgc aacccaactg gctctcctta c                                  31

<210> SEQ ID NO 208
<211> LENGTH: 30
<212> TYPE: DNA
<213> ORGANISM: Artificial
<220> FEATURE:
<223> OTHER INFORMATION: primer

<400> SEQUENCE: 208
cctcgccgca acccaactgg ctctccttac                                    30

<210> SEQ ID NO 209
<211> LENGTH: 29
<212> TYPE: DNA
<213> ORGANISM: Artificial
<220> FEATURE:
<223> OTHER INFORMATION: primer

<400> SEQUENCE: 209
ctcgccgcaa cccaactggc tctccttac                                     29

<210> SEQ ID NO 210
<211> LENGTH: 28
<212> TYPE: DNA
<213> ORGANISM: Artificial
<220> FEATURE:
<223> OTHER INFORMATION: primer

<400> SEQUENCE: 210
tcgccgcaac ccaactggct ctccttac                                      28

<210> SEQ ID NO 211
<211> LENGTH: 27
<212> TYPE: DNA
<213> ORGANISM: Artificial
<220> FEATURE:
<223> OTHER INFORMATION: primer

<400> SEQUENCE: 211
cgccgcaacc caactggctc tccttac                                       27
```

<210> SEQ ID NO 212
<211> LENGTH: 26
<212> TYPE: DNA
<213> ORGANISM: Artificial
<220> FEATURE:
<223> OTHER INFORMATION: primer

<400> SEQUENCE: 212
gccgcaaccc aactggctct ccttac                                          26

<210> SEQ ID NO 213
<211> LENGTH: 25
<212> TYPE: DNA
<213> ORGANISM: Artificial
<220> FEATURE:
<223> OTHER INFORMATION: primer

<400> SEQUENCE: 213
ccgcaaccca actggctctc cttac                                           25

<210> SEQ ID NO 214
<211> LENGTH: 24
<212> TYPE: DNA
<213> ORGANISM: Artificial
<220> FEATURE:
<223> OTHER INFORMATION: primer

<400> SEQUENCE: 214
cgcaacccaa ctggctctcc ttac                                            24

<210> SEQ ID NO 215
<211> LENGTH: 23
<212> TYPE: DNA
<213> ORGANISM: Artificial
<220> FEATURE:
<223> OTHER INFORMATION: primer

<400> SEQUENCE: 215
gcaacccaac tggctctcct tac                                             23

<210> SEQ ID NO 216
<211> LENGTH: 22
<212> TYPE: DNA
<213> ORGANISM: Artificial
<220> FEATURE:
<223> OTHER INFORMATION: primer

<400> SEQUENCE: 216
caacccaact ggctctcctt ac                                              22

<210> SEQ ID NO 217
<211> LENGTH: 39
<212> TYPE: DNA
<213> ORGANISM: Artificial
<220> FEATURE:
<223> OTHER INFORMATION: primer

<400> SEQUENCE: 217
aaagaagtca ggattccatg gaggctggat aggaggtcc                            39

<210> SEQ ID NO 218
<211> LENGTH: 38
<212> TYPE: DNA
<213> ORGANISM: Artificial
<220> FEATURE:
<223> OTHER INFORMATION: primer -continued

<400> SEQUENCE: 218
aagaagtcag gattccatgg aggctggata ggaggtcc                    38

<210> SEQ ID NO 219
<211> LENGTH: 37
<212> TYPE: DNA
<213> ORGANISM: Artificial
<220> FEATURE:
<223> OTHER INFORMATION: primer

<400> SEQUENCE: 219
agaagtcagg attccatgga ggctggatag gaggtcc                     37

<210> SEQ ID NO 220
<211> LENGTH: 36
<212> TYPE: DNA
<213> ORGANISM: Artificial
<220> FEATURE:
<223> OTHER INFORMATION: primer

<400> SEQUENCE: 220
gaagtcagga ttccatggag gctggatagg aggtcc                      36

<210> SEQ ID NO 221
<211> LENGTH: 35
<212> TYPE: DNA
<213> ORGANISM: Artificial
<220> FEATURE:
<223> OTHER INFORMATION: primer

<400> SEQUENCE: 221
aagtcaggat tccatggagg ctggatagga ggtcc                       35

<210> SEQ ID NO 222
<211> LENGTH: 34
<212> TYPE: DNA
<213> ORGANISM: Artificial
<220> FEATURE:
<223> OTHER INFORMATION: primer

<400> SEQUENCE: 222
agtcaggatt ccatggaggc tggataggag gtcc                        34

<210> SEQ ID NO 223
<211> LENGTH: 33
<212> TYPE: DNA
<213> ORGANISM: Artificial
<220> FEATURE:
<223> OTHER INFORMATION: primer

<400> SEQUENCE: 223
gtcaggattc catggaggct ggataggagg tcc                         33

<210> SEQ ID NO 224
<211> LENGTH: 32
<212> TYPE: DNA
<213> ORGANISM: Artificial
<220> FEATURE:
<223> OTHER INFORMATION: primer

<400> SEQUENCE: 224
tcaggattcc atggaggctg gataggaggt cc                          32

<210> SEQ ID NO 225
<211> LENGTH: 31

```
<212> TYPE: DNA
<213> ORGANISM: Artificial
<220> FEATURE:
<223> OTHER INFORMATION: primer

<400> SEQUENCE: 225
caggattcca tggaggctgg ataggaggtc c                                    31

<210> SEQ ID NO 226
<211> LENGTH: 30
<212> TYPE: DNA
<213> ORGANISM: Artificial
<220> FEATURE:
<223> OTHER INFORMATION: primer

<400> SEQUENCE: 226
aggattccat ggaggctgga taggaggtcc                                      30

<210> SEQ ID NO 227
<211> LENGTH: 29
<212> TYPE: DNA
<213> ORGANISM: Artificial
<220> FEATURE:
<223> OTHER INFORMATION: primer

<400> SEQUENCE: 227
ggattccatg gaggctggat aggaggtcc                                       29

<210> SEQ ID NO 228
<211> LENGTH: 28
<212> TYPE: DNA
<213> ORGANISM: Artificial
<220> FEATURE:
<223> OTHER INFORMATION: primer

<400> SEQUENCE: 228
gattccatgg aggctggata ggaggtcc                                        28

<210> SEQ ID NO 229
<211> LENGTH: 27
<212> TYPE: DNA
<213> ORGANISM: Artificial
<220> FEATURE:
<223> OTHER INFORMATION: primer

<400> SEQUENCE: 229
attccatgga ggctggatag gaggtcc                                         27

<210> SEQ ID NO 230
<211> LENGTH: 26
<212> TYPE: DNA
<213> ORGANISM: Artificial
<220> FEATURE:
<223> OTHER INFORMATION: primer

<400> SEQUENCE: 230
ttccatggag gctggatagg aggtcc                                          26

<210> SEQ ID NO 231
<211> LENGTH: 25
<212> TYPE: DNA
<213> ORGANISM: Artificial
<220> FEATURE:
<223> OTHER INFORMATION: primer

<400> SEQUENCE: 231
```

```
tccatggagg ctggatagga ggtcc                                            25

<210> SEQ ID NO 232
<211> LENGTH: 24
<212> TYPE: DNA
<213> ORGANISM: Artificial
<220> FEATURE:
<223> OTHER INFORMATION: primer

<400> SEQUENCE: 232
ccatggaggc tggataggag gtcc                                             24

<210> SEQ ID NO 233
<211> LENGTH: 23
<212> TYPE: DNA
<213> ORGANISM: Artificial
<220> FEATURE:
<223> OTHER INFORMATION: primer

<400> SEQUENCE: 233
catggaggct ggataggagg tcc                                              23

<210> SEQ ID NO 234
<211> LENGTH: 42
<212> TYPE: DNA
<213> ORGANISM: Artificial
<220> FEATURE:
<223> OTHER INFORMATION: primer

<400> SEQUENCE: 234
agaggagcag ggatggaaga agagaggtat tcccttccc ac                         42

<210> SEQ ID NO 235
<211> LENGTH: 41
<212> TYPE: DNA
<213> ORGANISM: Artificial
<220> FEATURE:
<223> OTHER INFORMATION: primer

<400> SEQUENCE: 235
gaggagcagg gatggaagaa gagaggtatt cccttccca c                          41

<210> SEQ ID NO 236
<211> LENGTH: 40
<212> TYPE: DNA
<213> ORGANISM: Artificial
<220> FEATURE:
<223> OTHER INFORMATION: primer

<400> SEQUENCE: 236
aggagcaggg atggaagaag agaggtattc cccttcccac                            40

<210> SEQ ID NO 237
<211> LENGTH: 39
<212> TYPE: DNA
<213> ORGANISM: Artificial
<220> FEATURE:
<223> OTHER INFORMATION: primer

<400> SEQUENCE: 237
ggagcaggga tggaagaaga gaggtattcc ccttcccac                             39

<210> SEQ ID NO 238
<211> LENGTH: 38
<212> TYPE: DNA
<213> ORGANISM: Artificial
```

```
<220> FEATURE:
<223> OTHER INFORMATION: primer

<400> SEQUENCE: 238
gagcagggat ggaagaagag aggtattccc cttcccac                              38

<210> SEQ ID NO 239
<211> LENGTH: 37
<212> TYPE: DNA
<213> ORGANISM: Artificial
<220> FEATURE:
<223> OTHER INFORMATION: primer

<400> SEQUENCE: 239
agcagggatg gaagaagaga ggtattcccc ttcccac                               37

<210> SEQ ID NO 240
<211> LENGTH: 36
<212> TYPE: DNA
<213> ORGANISM: Artificial
<220> FEATURE:
<223> OTHER INFORMATION: primer

<400> SEQUENCE: 240
gcagggatgg aagaagagag gtattcccct tcccac                                36

<210> SEQ ID NO 241
<211> LENGTH: 35
<212> TYPE: DNA
<213> ORGANISM: Artificial
<220> FEATURE:
<223> OTHER INFORMATION: primer

<400> SEQUENCE: 241
cagggatgga agaagagagg tattcccctt cccac                                 35

<210> SEQ ID NO 242
<211> LENGTH: 34
<212> TYPE: DNA
<213> ORGANISM: Artificial
<220> FEATURE:
<223> OTHER INFORMATION: primer

<400> SEQUENCE: 242
agggatggaa gaagagaggt attccccttc ccac                                  34

<210> SEQ ID NO 243
<211> LENGTH: 33
<212> TYPE: DNA
<213> ORGANISM: Artificial
<220> FEATURE:
<223> OTHER INFORMATION: primer

<400> SEQUENCE: 243
gggatggaag aagagaggta ttccccttcc cac                                   33

<210> SEQ ID NO 244
<211> LENGTH: 32
<212> TYPE: DNA
<213> ORGANISM: Artificial
<220> FEATURE:
<223> OTHER INFORMATION: primer

<400> SEQUENCE: 244
ggatggaaga agagaggtat tcccttccc ac                                     32
```

<210> SEQ ID NO 245
<211> LENGTH: 31
<212> TYPE: DNA
<213> ORGANISM: Artificial
<220> FEATURE:
<223> OTHER INFORMATION: primer

<400> SEQUENCE: 245
gatggaagaa gagaggtatt ccccttccca c                          31

<210> SEQ ID NO 246
<211> LENGTH: 30
<212> TYPE: DNA
<213> ORGANISM: Artificial
<220> FEATURE:
<223> OTHER INFORMATION: primer

<400> SEQUENCE: 246
atggaagaag agaggtattc ccttcccac                             30

<210> SEQ ID NO 247
<211> LENGTH: 29
<212> TYPE: DNA
<213> ORGANISM: Artificial
<220> FEATURE:
<223> OTHER INFORMATION: primer

<400> SEQUENCE: 247
tggaagaaga gaggtattcc ccttcccac                             29

<210> SEQ ID NO 248
<211> LENGTH: 28
<212> TYPE: DNA
<213> ORGANISM: Artificial
<220> FEATURE:
<223> OTHER INFORMATION: primer

<400> SEQUENCE: 248
ggaagaagag aggtattccc cttcccac                              28

<210> SEQ ID NO 249
<211> LENGTH: 27
<212> TYPE: DNA
<213> ORGANISM: Artificial
<220> FEATURE:
<223> OTHER INFORMATION: primer

<400> SEQUENCE: 249
gaagaagaga ggtattcccc ttcccac                               27

<210> SEQ ID NO 250
<211> LENGTH: 26
<212> TYPE: DNA
<213> ORGANISM: Artificial
<220> FEATURE:
<223> OTHER INFORMATION: primer

<400> SEQUENCE: 250
aagaagagag gtattcccct tcccac                                26

<210> SEQ ID NO 251
<211> LENGTH: 25
<212> TYPE: DNA
<213> ORGANISM: Artificial
<220> FEATURE:
<223> OTHER INFORMATION: primer

```
-continued

<400> SEQUENCE: 251
agaagagagg tattcccctt cccac                                              25

<210> SEQ ID NO 252
<211> LENGTH: 33
<212> TYPE: DNA
<213> ORGANISM: Artificial
<220> FEATURE:
<223> OTHER INFORMATION: primer

<400> SEQUENCE: 252
gcctgagtcc agtttgccct caagcccaga tgc                                     33

<210> SEQ ID NO 253
<211> LENGTH: 32
<212> TYPE: DNA
<213> ORGANISM: Artificial
<220> FEATURE:
<223> OTHER INFORMATION: primer

<400> SEQUENCE: 253
cctgagtcca gtttgccctc aagcccagat gc                                      32

<210> SEQ ID NO 254
<211> LENGTH: 31
<212> TYPE: DNA
<213> ORGANISM: Artificial
<220> FEATURE:
<223> OTHER INFORMATION: primer

<400> SEQUENCE: 254
ctgagtccag tttgccctca agcccagatg c                                       31

<210> SEQ ID NO 255
<211> LENGTH: 30
<212> TYPE: DNA
<213> ORGANISM: Artificial
<220> FEATURE:
<223> OTHER INFORMATION: primer

<400> SEQUENCE: 255
tgagtccagt ttgccctcaa gcccagatgc                                         30

<210> SEQ ID NO 256
<211> LENGTH: 29
<212> TYPE: DNA
<213> ORGANISM: Artificial
<220> FEATURE:
<223> OTHER INFORMATION: primer

<400> SEQUENCE: 256
gagtccagtt tgccctcaag cccagatgc                                          29

<210> SEQ ID NO 257
<211> LENGTH: 28
<212> TYPE: DNA
<213> ORGANISM: Artificial
<220> FEATURE:
<223> OTHER INFORMATION: primer

<400> SEQUENCE: 257
agtccagttt gccctcaagc ccagatgc                                           28

<210> SEQ ID NO 258
```

```
<211> LENGTH: 27
<212> TYPE: DNA
<213> ORGANISM: Artificial
<220> FEATURE:
<223> OTHER INFORMATION: primer

<400> SEQUENCE: 258
gtccagtttg ccctcaagcc cagatgc                                          27

<210> SEQ ID NO 259
<211> LENGTH: 26
<212> TYPE: DNA
<213> ORGANISM: Artificial
<220> FEATURE:
<223> OTHER INFORMATION: primer

<400> SEQUENCE: 259
tccagtttgc cctcaagccc agatgc                                           26

<210> SEQ ID NO 260
<211> LENGTH: 25
<212> TYPE: DNA
<213> ORGANISM: Artificial
<220> FEATURE:
<223> OTHER INFORMATION: primer

<400> SEQUENCE: 260
ccagtttgcc ctcaagccca gatgc                                            25

<210> SEQ ID NO 261
<211> LENGTH: 24
<212> TYPE: DNA
<213> ORGANISM: Artificial
<220> FEATURE:
<223> OTHER INFORMATION: primer

<400> SEQUENCE: 261
cagtttgccc tcaagcccag atgc                                             24

<210> SEQ ID NO 262
<211> LENGTH: 23
<212> TYPE: DNA
<213> ORGANISM: Artificial
<220> FEATURE:
<223> OTHER INFORMATION: primer

<400> SEQUENCE: 262
agtttgccct caagcccaga tgc                                              23

<210> SEQ ID NO 263
<211> LENGTH: 22
<212> TYPE: DNA
<213> ORGANISM: Artificial
<220> FEATURE:
<223> OTHER INFORMATION: primer

<400> SEQUENCE: 263
gtttgccctc aagcccagat gc                                               22

<210> SEQ ID NO 264
<211> LENGTH: 21
<212> TYPE: DNA
<213> ORGANISM: Artificial
<220> FEATURE:
<223> OTHER INFORMATION: primer

<400> SEQUENCE: 264
```

```
tttgccctca agcccagatg c                                              21

<210> SEQ ID NO 265
<211> LENGTH: 20
<212> TYPE: DNA
<213> ORGANISM: Artificial
<220> FEATURE:
<223> OTHER INFORMATION: primer

<400> SEQUENCE: 265
ttgccctcaa gcccagatgc                                                20

<210> SEQ ID NO 266
<211> LENGTH: 19
<212> TYPE: DNA
<213> ORGANISM: Artificial
<220> FEATURE:
<223> OTHER INFORMATION: primer

<400> SEQUENCE: 266
tgccctcaag cccagatgc                                                 19

<210> SEQ ID NO 267
<211> LENGTH: 41
<212> TYPE: DNA
<213> ORGANISM: Artificial
<220> FEATURE:
<223> OTHER INFORMATION: primer

<400> SEQUENCE: 267
agaccacaga cctggtcccc aaaagaaatg gaggcaatag g                        41

<210> SEQ ID NO 268
<211> LENGTH: 40
<212> TYPE: DNA
<213> ORGANISM: Artificial
<220> FEATURE:
<223> OTHER INFORMATION: primer

<400> SEQUENCE: 268
gaccacagac ctggtcccca aagaaatgga ggcaatagg                           40

<210> SEQ ID NO 269
<211> LENGTH: 39
<212> TYPE: DNA
<213> ORGANISM: Artificial
<220> FEATURE:
<223> OTHER INFORMATION: primer

<400> SEQUENCE: 269
accacagacc tggtccccaa agaaatgga ggcaatagg                            39

<210> SEQ ID NO 270
<211> LENGTH: 38
<212> TYPE: DNA
<213> ORGANISM: Artificial
<220> FEATURE:
<223> OTHER INFORMATION: primer

<400> SEQUENCE: 270
ccacagacct ggtccccaaa agaaatggag gcaatagg                            38

<210> SEQ ID NO 271
<211> LENGTH: 37
<212> TYPE: DNA
```

```
<213> ORGANISM: Artificial
<220> FEATURE:
<223> OTHER INFORMATION: primer

<400> SEQUENCE: 271
cacagacctg gtccccaaaa gaaatggagg caatagg                              37

<210> SEQ ID NO 272
<211> LENGTH: 36
<212> TYPE: DNA
<213> ORGANISM: Artificial
<220> FEATURE:
<223> OTHER INFORMATION: primer

<400> SEQUENCE: 272
acagacctgg tccccaaaag aaatggaggc aatagg                               36

<210> SEQ ID NO 273
<211> LENGTH: 35
<212> TYPE: DNA
<213> ORGANISM: Artificial
<220> FEATURE:
<223> OTHER INFORMATION: primer

<400> SEQUENCE: 273
cagacctggt cccaaaaga atggaggca atagg                                  35

<210> SEQ ID NO 274
<211> LENGTH: 34
<212> TYPE: DNA
<213> ORGANISM: Artificial
<220> FEATURE:
<223> OTHER INFORMATION: primer

<400> SEQUENCE: 274
agacctggtc cccaaaagaa atggaggcaa tagg                                 34

<210> SEQ ID NO 275
<211> LENGTH: 33
<212> TYPE: DNA
<213> ORGANISM: Artificial
<220> FEATURE:
<223> OTHER INFORMATION: primer

<400> SEQUENCE: 275
gacctggtcc ccaaaagaaa tggaggcaat agg                                  33

<210> SEQ ID NO 276
<211> LENGTH: 32
<212> TYPE: DNA
<213> ORGANISM: Artificial
<220> FEATURE:
<223> OTHER INFORMATION: primer

<400> SEQUENCE: 276
acctggtccc caaaagaaat ggaggcaata gg                                   32

<210> SEQ ID NO 277
<211> LENGTH: 31
<212> TYPE: DNA
<213> ORGANISM: Artificial
<220> FEATURE:
<223> OTHER INFORMATION: primer

<400> SEQUENCE: 277
cctggtcccc aaaagaaatg gaggcaatag g                                    31
```

```
<210> SEQ ID NO 278
<211> LENGTH: 30
<212> TYPE: DNA
<213> ORGANISM: Artificial
<220> FEATURE:
<223> OTHER INFORMATION: primer

<400> SEQUENCE: 278
ctggtcccca aagaaatgg aggcaatagg                                      30

<210> SEQ ID NO 279
<211> LENGTH: 29
<212> TYPE: DNA
<213> ORGANISM: Artificial
<220> FEATURE:
<223> OTHER INFORMATION: primer

<400> SEQUENCE: 279 tggtcccccaa aagaaatgga ggcaatagg                                      29

<210> SEQ ID NO 280
<211> LENGTH: 28
<212> TYPE: DNA
<213> ORGANISM: Artificial
<220> FEATURE:
<223> OTHER INFORMATION: primer

<400> SEQUENCE: 280
ggtccccaaa agaaatggag gcaatagg                                        28

<210> SEQ ID NO 281
<211> LENGTH: 27
<212> TYPE: DNA
<213> ORGANISM: Artificial
<220> FEATURE:
<223> OTHER INFORMATION: primer

<400> SEQUENCE: 281
gtccccaaaa gaaatggagg caatagg                                         27

<210> SEQ ID NO 282
<211> LENGTH: 26
<212> TYPE: DNA
<213> ORGANISM: Artificial
<220> FEATURE:
<223> OTHER INFORMATION: primer

<400> SEQUENCE: 282
tccccaaaag aaatggaggc aatagg                                          26

<210> SEQ ID NO 283
<211> LENGTH: 40
<212> TYPE: DNA
<213> ORGANISM: Artificial
<220> FEATURE:
<223> OTHER INFORMATION: primer

<400> SEQUENCE: 283
gtcttctggg ccactgactg atttgtgtgt aggaccctgg                           40

<210> SEQ ID NO 284
<211> LENGTH: 39
<212> TYPE: DNA
<213> ORGANISM: Artificial
<220> FEATURE:
```

```
<223> OTHER INFORMATION: primer

<400> SEQUENCE: 284
tcttctgggc cactgactga tttgtgtgta ggaccctgg                    39

<210> SEQ ID NO 285
<211> LENGTH: 38
<212> TYPE: DNA
<213> ORGANISM: Artificial
<220> FEATURE:
<223> OTHER INFORMATION: primer

<400> SEQUENCE: 285
cttctgggcc actgactgat ttgtgtgtag gaccctgg                     38

<210> SEQ ID NO 286
<211> LENGTH: 37
<212> TYPE: DNA
<213> ORGANISM: Artificial
<220> FEATURE:
<223> OTHER INFORMATION: primer

<400> SEQUENCE: 286
ttctgggcca ctgactgatt tgtgtgtagg accctgg                      37

<210> SEQ ID NO 287
<211> LENGTH: 36
<212> TYPE: DNA
<213> ORGANISM: Artificial
<220> FEATURE:
<223> OTHER INFORMATION: primer

<400> SEQUENCE: 287
tctgggccac tgactgattt gtgtgtagga ccctgg                       36

<210> SEQ ID NO 288
<211> LENGTH: 35
<212> TYPE: DNA
<213> ORGANISM: Artificial
<220> FEATURE:
<223> OTHER INFORMATION: primer

<400> SEQUENCE: 288
ctgggccact gactgatttg tgtgtaggac cctgg                        35

<210> SEQ ID NO 289
<211> LENGTH: 34
<212> TYPE: DNA
<213> ORGANISM: Artificial
<220> FEATURE:
<223> OTHER INFORMATION: primer

<400> SEQUENCE: 289
tgggccactg actgatttgt gtgtaggacc ctgg                         34

<210> SEQ ID NO 290
<211> LENGTH: 33
<212> TYPE: DNA
<213> ORGANISM: Artificial
<220> FEATURE:
<223> OTHER INFORMATION: primer

<400> SEQUENCE: 290
gggccactga ctgatttgtg tgtaggaccc tgg                          33
```

```
<210> SEQ ID NO 291
<211> LENGTH: 32
<212> TYPE: DNA
<213> ORGANISM: Artificial
<220> FEATURE:
<223> OTHER INFORMATION: primer

<400> SEQUENCE: 291
ggccactgac tgatttgtgt gtaggaccct gg                           32

<210> SEQ ID NO 292
<211> LENGTH: 31
<212> TYPE: DNA
<213> ORGANISM: Artificial
<220> FEATURE:
<223> OTHER INFORMATION: primer

<400> SEQUENCE: 292
gccactgact gatttgtgtg taggaccctg g                            31

<210> SEQ ID NO 293
<211> LENGTH: 30
<212> TYPE: DNA
<213> ORGANISM: Artificial
<220> FEATURE:
<223> OTHER INFORMATION: primer

<400> SEQUENCE: 293
ccactgactg atttgtgtgt aggaccctgg                              30

<210> SEQ ID NO 294
<211> LENGTH: 29
<212> TYPE: DNA
<213> ORGANISM: Artificial
<220> FEATURE:
<223> OTHER INFORMATION: primer

<400> SEQUENCE: 294
cactgactga tttgtgtgta ggaccctgg                               29

<210> SEQ ID NO 295
<211> LENGTH: 28
<212> TYPE: DNA
<213> ORGANISM: Artificial
<220> FEATURE:
<223> OTHER INFORMATION: primer

<400> SEQUENCE: 295
actgactgat ttgtgtgtag gaccctgg                                28

<210> SEQ ID NO 296
<211> LENGTH: 27
<212> TYPE: DNA
<213> ORGANISM: Artificial
<220> FEATURE:
<223> OTHER INFORMATION: primer

<400> SEQUENCE: 296
ctgactgatt tgtgtgtagg accctgg                                 27

<210> SEQ ID NO 297
<211> LENGTH: 26
<212> TYPE: DNA
<213> ORGANISM: Artificial
<220> FEATURE:
<223> OTHER INFORMATION: primer
```

```
<400> SEQUENCE: 297 tgactgatttt gtgtgtagga ccctgg                                        26

<210> SEQ ID NO 298
<211> LENGTH: 25
<212> TYPE: DNA
<213> ORGANISM: Artificial
<220> FEATURE:
<223> OTHER INFORMATION: primer

<400> SEQUENCE: 298
gactgatttg tgtgtaggac cctgg                                          25

<210> SEQ ID NO 299
<211> LENGTH: 24
<212> TYPE: DNA
<213> ORGANISM: Artificial
<220> FEATURE:
<223> OTHER INFORMATION: primer

<400> SEQUENCE: 299
actgatttgt gtgtaggacc ctgg                                           24

<210> SEQ ID NO 300
<211> LENGTH: 801
<212> TYPE: DNA
<213> ORGANISM: Homo sapiens

<400> SEQUENCE: 300
agggagcccc tagggagaaa cagagttgag gggggctcta gggctcaagg tttggctgag    60 ccacccagc agcccccatt ctcctgctgc ctcacctggg ccccaggcag cagaaccagc    120
agcagcccca gaaggaggag gtgtagggtg gtgccacaca cccttgggag gaagagacgt    180
tcaggtggtg tcatggggag aacctgcaga gaaagagaga gagagagaga gacagtgagc    240
ggggcggggc acgcggcgga agacagacct cccgccctgg gagacagcac cccccgaccc    300
ccgagagaga gatcgacaga gaaggggaca agatgcagtc agagaaaccc caaggtgagc    360
agagggagac agagagagac aggaagggaa cagagaggaa ycatggcaga aacagagaat    420
gtgtgacaga gacaatgaga ctgacagatg gagagtcaga gacagagaag gaaaccaaaa    480
ccaaacccac caaggcccag gcccaggcag gccggggatc caggcagcag gtgcaggagg    540
gaccgaggcc caggcagagg gcaggacact gcggggcggt agtccaaagc acgaagcacg    600
ggcagcccaa ggagatgggg caggagagcc tcacctgctg tgtggagccc ctgggcccgg    660
acgctcaggt ccctttatag aggaagcggc agtggcagcg tggcaggcag cgggcgggtt    720
ctaggtcggg gctggggccc ggggaagccc ccagggctta aagatactg ctgtttcagt    780 caaaggcagg aaaggctgag g                                             801

<210> SEQ ID NO 301
<211> LENGTH: 22
<212> TYPE: DNA
<213> ORGANISM: Artificial
<220> FEATURE:
<223> OTHER INFORMATION: probe

<400> SEQUENCE: 301
tgtttctgcc atggttcctc tc                                             22

<210> SEQ ID NO 302
<211> LENGTH: 21
```

```
<212> TYPE: DNA
<213> ORGANISM: Artificial
<220> FEATURE:
<223> OTHER INFORMATION: probe

<400> SEQUENCE: 302
gtttctgcca tggttcctct c                                              21

<210> SEQ ID NO 303
<211> LENGTH: 20
<212> TYPE: DNA
<213> ORGANISM: Artificial
<220> FEATURE:
<223> OTHER INFORMATION: probe

<400> SEQUENCE: 303
tttctgccat ggttcctctc                                                20

<210> SEQ ID NO 304
<211> LENGTH: 19
<212> TYPE: DNA
<213> ORGANISM: Artificial
<220> FEATURE:
<223> OTHER INFORMATION: probe

<400> SEQUENCE: 304
ttctgccatg gttcctctc                                                 19

<210> SEQ ID NO 305
<211> LENGTH: 18
<212> TYPE: DNA
<213> ORGANISM: Artificial
<220> FEATURE:
<223> OTHER INFORMATION: probe

<400> SEQUENCE: 305
tctgccatgg ttcctctc                                                  18

<210> SEQ ID NO 306
<211> LENGTH: 17
<212> TYPE: DNA
<213> ORGANISM: Artificial
<220> FEATURE:
<223> OTHER INFORMATION: probe

<400> SEQUENCE: 306
ctgccatggt tcctctc                                                   17

<210> SEQ ID NO 307
<211> LENGTH: 16
<212> TYPE: DNA
<213> ORGANISM: Artificial
<220> FEATURE:
<223> OTHER INFORMATION: probe

<400> SEQUENCE: 307
tgccatggtt cctctc                                                    16

<210> SEQ ID NO 308
<211> LENGTH: 15
<212> TYPE: DNA
<213> ORGANISM: Artificial
<220> FEATURE:
<223> OTHER INFORMATION: probe

<400> SEQUENCE: 308
```
gccatggttc ctctc                                                                        15

<210> SEQ ID NO 309
<211> LENGTH: 37
<212> TYPE: DNA
<213> ORGANISM: Artificial
<220> FEATURE:
<223> OTHER INFORMATION: primer

<400> SEQUENCE: 309
tttggtttcc ttctctgtct ctgactctcc atctgtc                                                37

<210> SEQ ID NO 310
<211> LENGTH: 36
<212> TYPE: DNA
<213> ORGANISM: Artificial
<220> FEATURE:
<223> OTHER INFORMATION: primer

<400> SEQUENCE: 310
ttggtttcct tctctgtctc tgactctcca tctgtc                                                 36

<210> SEQ ID NO 311
<211> LENGTH: 35
<212> TYPE: DNA
<213> ORGANISM: Artificial
<220> FEATURE:
<223> OTHER INFORMATION: primer

<400> SEQUENCE: 311
tggtttcctt ctctgtctct gactctccat ctgtc                                                  35

<210> SEQ ID NO 312
<211> LENGTH: 34
<212> TYPE: DNA
<213> ORGANISM: Artificial
<220> FEATURE:
<223> OTHER INFORMATION: primer

<400> SEQUENCE: 312
ggtttccttc tctgtctctg actctccatc tgtc                                                   34

<210> SEQ ID NO 313
<211> LENGTH: 33
<212> TYPE: DNA
<213> ORGANISM: Artificial
<220> FEATURE:
<223> OTHER INFORMATION: primer

<400> SEQUENCE: 313
gtttccttct ctgtctctga ctctccatct gtc                                                    33

<210> SEQ ID NO 314
<211> LENGTH: 32
<212> TYPE: DNA
<213> ORGANISM: Artificial
<220> FEATURE:
<223> OTHER INFORMATION: primer

<400> SEQUENCE: 314
tttccttctc tgtctctgac tctccatctg tc                                                     32

<210> SEQ ID NO 315
<211> LENGTH: 31
<212> TYPE: DNA
<213> ORGANISM: Artificial

```
<220> FEATURE:
<223> OTHER INFORMATION: primer

<400> SEQUENCE: 315
ttccttctct gtctctgact ctccatctgt c                                    31

<210> SEQ ID NO 316
<211> LENGTH: 30
<212> TYPE: DNA
<213> ORGANISM: Artificial
<220> FEATURE:
<223> OTHER INFORMATION: primer

<400> SEQUENCE: 316
tccttctctg tctctgactc tccatctgtc                                      30

<210> SEQ ID NO 317
<211> LENGTH: 29
<212> TYPE: DNA
<213> ORGANISM: Artificial
<220> FEATURE:
<223> OTHER INFORMATION: primer

<400> SEQUENCE: 317
ccttctctgt tctgactct ccatctgtc                                        29

<210> SEQ ID NO 318
<211> LENGTH: 28
<212> TYPE: DNA
<213> ORGANISM: Artificial
<220> FEATURE:
<223> OTHER INFORMATION: primer

<400> SEQUENCE: 318
cttctctgtc tctgactctc catctgtc                                        28

<210> SEQ ID NO 319
<211> LENGTH: 27
<212> TYPE: DNA
<213> ORGANISM: Artificial
<220> FEATURE:
<223> OTHER INFORMATION: primer

<400> SEQUENCE: 319
ttctctgtct ctgactctcc atctgtc                                         27

<210> SEQ ID NO 320
<211> LENGTH: 26
<212> TYPE: DNA
<213> ORGANISM: Artificial
<220> FEATURE:
<223> OTHER INFORMATION: primer

<400> SEQUENCE: 320
tctctgtctc tgactctcca tctgtc                                          26

<210> SEQ ID NO 321
<211> LENGTH: 25
<212> TYPE: DNA
<213> ORGANISM: Artificial
<220> FEATURE:
<223> OTHER INFORMATION: primer

<400> SEQUENCE: 321
ctctgtctct gactctccat ctgtc                                           25
```

<210> SEQ ID NO 322
<211> LENGTH: 24
<212> TYPE: DNA
<213> ORGANISM: Artificial
<220> FEATURE:
<223> OTHER INFORMATION: primer

<400> SEQUENCE: 322
tctgtctctg actctccatc tgtc                                          24

<210> SEQ ID NO 323
<211> LENGTH: 23
<212> TYPE: DNA
<213> ORGANISM: Artificial
<220> FEATURE:
<223> OTHER INFORMATION: primer

<400> SEQUENCE: 323
ctgtctctga ctctccatct gtc                                           23

<210> SEQ ID NO 324
<211> LENGTH: 22
<212> TYPE: DNA
<213> ORGANISM: Artificial
<220> FEATURE:
<223> OTHER INFORMATION: primer

<400> SEQUENCE: 324
tgtctctgac tctccatctg tc                                            22

<210> SEQ ID NO 325
<211> LENGTH: 21
<212> TYPE: DNA
<213> ORGANISM: Artificial
<220> FEATURE:
<223> OTHER INFORMATION: primer

<400> SEQUENCE: 325
gtctctgact ctccatctgt c                                             21

<210> SEQ ID NO 326
<211> LENGTH: 20
<212> TYPE: DNA
<213> ORGANISM: Artificial
<220> FEATURE:
<223> OTHER INFORMATION: primer

<400> SEQUENCE: 326
tctctgactc tccatctgtc                                               20

<210> SEQ ID NO 327
<211> LENGTH: 19
<212> TYPE: DNA
<213> ORGANISM: Artificial
<220> FEATURE:
<223> OTHER INFORMATION: primer

<400> SEQUENCE: 327
ctctgactct ccatctgtc                                                19

<210> SEQ ID NO 328
<211> LENGTH: 18
<212> TYPE: DNA
<213> ORGANISM: Artificial
<220> FEATURE:
<223> OTHER INFORMATION: primer -continued

<400> SEQUENCE: 328
tctgactctc catctgtc                                                         18

<210> SEQ ID NO 329
<211> LENGTH: 17
<212> TYPE: DNA
<213> ORGANISM: Artificial
<220> FEATURE:
<223> OTHER INFORMATION: primer

<400> SEQUENCE: 329
ctgactctcc atctgtc                                                          17

<210> SEQ ID NO 330
<211> LENGTH: 37
<212> TYPE: DNA
<213> ORGANISM: Artificial
<220> FEATURE:
<223> OTHER INFORMATION: primer

<400> SEQUENCE: 330
cgacagagaa ggggacaaga tgcagtcaga gaaaccc                                    37

<210> SEQ ID NO 331
<211> LENGTH: 36
<212> TYPE: DNA
<213> ORGANISM: Artificial
<220> FEATURE:
<223> OTHER INFORMATION: primer

<400> SEQUENCE: 331
gacagagaag gggacaagat gcagtcagag aaaccc                                     36

<210> SEQ ID NO 332
<211> LENGTH: 35
<212> TYPE: DNA
<213> ORGANISM: Artificial
<220> FEATURE:
<223> OTHER INFORMATION: primer

<400> SEQUENCE: 332
acagagaagg ggacaagatg cagtcagaga aaccc                                      35

<210> SEQ ID NO 333
<211> LENGTH: 34
<212> TYPE: DNA
<213> ORGANISM: Artificial
<220> FEATURE:
<223> OTHER INFORMATION: primer

<400> SEQUENCE: 333
cagagaaggg gacaagatgc agtcagagaa accc                                       34

<210> SEQ ID NO 334
<211> LENGTH: 33
<212> TYPE: DNA
<213> ORGANISM: Artificial
<220> FEATURE:
<223> OTHER INFORMATION: primer

<400> SEQUENCE: 334
agagaagggg acaagatgca gtcagagaaa ccc                                        33

<210> SEQ ID NO 335

```
<211> LENGTH: 32
<212> TYPE: DNA
<213> ORGANISM: Artificial
<220> FEATURE:
<223> OTHER INFORMATION: primer

<400> SEQUENCE: 335
gagaagggga caagatgcag tcagagaaac cc                                   32

<210> SEQ ID NO 336
<211> LENGTH: 31
<212> TYPE: DNA
<213> ORGANISM: Artificial
<220> FEATURE:
<223> OTHER INFORMATION: primer

<400> SEQUENCE: 336
agaaggggac aagatgcagt cagagaaacc c                                    31

<210> SEQ ID NO 337
<211> LENGTH: 30
<212> TYPE: DNA
<213> ORGANISM: Artificial
<220> FEATURE:
<223> OTHER INFORMATION: primer

<400> SEQUENCE: 337
gaaggggaca agatgcagtc agagaaaccc                                      30

<210> SEQ ID NO 338
<211> LENGTH: 29
<212> TYPE: DNA
<213> ORGANISM: Artificial
<220> FEATURE:
<223> OTHER INFORMATION: primer

<400> SEQUENCE: 338
aaggggacaa gatgcagtca gagaaaccc                                       29

<210> SEQ ID NO 339
<211> LENGTH: 28
<212> TYPE: DNA
<213> ORGANISM: Artificial
<220> FEATURE:
<223> OTHER INFORMATION: primer

<400> SEQUENCE: 339
aggggacaag atgcagtcag agaaaccc                                        28

<210> SEQ ID NO 340
<211> LENGTH: 27
<212> TYPE: DNA
<213> ORGANISM: Artificial
<220> FEATURE:
<223> OTHER INFORMATION: primer

<400> SEQUENCE: 340
ggggacaaga tgcagtcaga gaaaccc                                         27

<210> SEQ ID NO 341
<211> LENGTH: 26
<212> TYPE: DNA
<213> ORGANISM: Artificial
<220> FEATURE:
<223> OTHER INFORMATION: primer

<400> SEQUENCE: 341
```

```
gggacaagat gcagtcagag aaaccc                                           26

<210> SEQ ID NO 342
<211> LENGTH: 25
<212> TYPE: DNA
<213> ORGANISM: Artificial
<220> FEATURE:
<223> OTHER INFORMATION: primer

<400> SEQUENCE: 342
ggacaagatg cagtcagaga aaccc                                            25

<210> SEQ ID NO 343
<211> LENGTH: 24
<212> TYPE: DNA
<213> ORGANISM: Artificial
<220> FEATURE:
<223> OTHER INFORMATION: primer

<400> SEQUENCE: 343
gacaagatgc agtcagagaa accc                                             24

<210> SEQ ID NO 344
<211> LENGTH: 23
<212> TYPE: DNA
<213> ORGANISM: Artificial
<220> FEATURE:
<223> OTHER INFORMATION: primer

<400> SEQUENCE: 344
acaagatgca gtcagagaaa ccc                                              23

<210> SEQ ID NO 345
<211> LENGTH: 22
<212> TYPE: DNA
<213> ORGANISM: Artificial
<220> FEATURE:
<223> OTHER INFORMATION: primer

<400> SEQUENCE: 345
caagatgcag tcagagaaac cc                                               22

<210> SEQ ID NO 346
<211> LENGTH: 21
<212> TYPE: DNA
<213> ORGANISM: Artificial
<220> FEATURE:
<223> OTHER INFORMATION: primer

<400> SEQUENCE: 346
aagatgcagt cagagaaacc c                                                21

<210> SEQ ID NO 347
<211> LENGTH: 20
<212> TYPE: DNA
<213> ORGANISM: Artificial
<220> FEATURE:
<223> OTHER INFORMATION: primer

<400> SEQUENCE: 347
agatgcagtc agagaaaccc                                                  20

<210> SEQ ID NO 348
<211> LENGTH: 19
<212> TYPE: DNA
```

```
<213> ORGANISM: Artificial
<220> FEATURE:
<223> OTHER INFORMATION: primer

<400> SEQUENCE: 348
gatgcagtca gagaaaccc                                              19

<210> SEQ ID NO 349
<211> LENGTH: 18
<212> TYPE: DNA
<213> ORGANISM: Artificial
<220> FEATURE:
<223> OTHER INFORMATION: primer

<400> SEQUENCE: 349
atgcagtcag agaaaccc                                               18
```

PROBES FOR DETECTING IMMUNE-RELATED GENE POLYMORPHISMS AND APPLICATIONS OF THE SAME

TECHNICAL FIELD

The present invention relates to probes for detecting polymorphisms of immune-related genes and to applications thereof.

BACKGROUND ART

Detection of a point mutation, a so-called single nucleotide polymorphism (SNP), is employed widely as a method of analyzing, at the gene level, for example, the causes of all types of diseases and the individual differences in disease liability (susceptibility to diseases) and in drug action.

Polymorphism detection methods that generally are practiced include (1) direct sequencing in which, in connection with the target DNA of a sample, a region to be detected is amplified by PCR (polymerase chain reaction) and the entire sequence of the amplification product thereof is analyzed; (2) PCR-RFLP (restriction fragment length polymorphism) in which PCR is performed in the same manner as in item (1) above, the amplification product is treated with restriction enzymes, and the change in restriction fragment length due to the polymorphisms is subjected to typing by Southern hybridization; and like methods.

However, the method of item (1) above requires, for example, sequencing after PCR and then electrophoresis or the like by a sequencer. The detection is thus very troublesome and costly. Moreover, the resulting amplification product needs to be subjected to treatment after PCR and may be contaminated during such treatment. The method of item (2) above also requires treatment of the resulting amplification product with a variety of restriction enzymes for analysis after PCR, thereby being troublesome. Moreover, the treatment of the resulting amplification product with restriction enzymes needs to be performed after the amplification product is transferred. Therefore, it may be possible that the amplification product obtained in a first reaction is scattered and may find another way into a second reaction that is performed separately. These problems cause another problem in that it is difficult with the methods of items (1) and (2) to automate the detection of point mutation.

Addressing these problems, a Tm (melting temperature) analysis recently has been attracting attention as a method for detecting an SNP. In this method, first, using a probe that is complementary to a region containing the SNP to be detected, a hybrid (double-strand nucleic acid) between a sample nucleic acid and the probe is formed. The hybridization product then is subjected to heat treatment, and the dissociation (melting) of the hybrid into a single-strand nucleic acid in response to a temperature increase is detected by measuring a signal such as absorbance. This is a method for determining an SNP by obtaining a Tm value based on the result of detection. The higher the homology of a hybridization product, the higher the Tm value, and the lower the homology, the lower the Tm value. Therefore, when the polymorphism of a detection target site is X or Y, a Tm value (reference value for evaluation) is obtained in advance in connection with a product of hybridization between a nucleic acid containing the desired polymorphism (for example, Y) and a probe that is 100% complementary thereto. Then, the Tm value of the sample nucleic acid and the probe is measured (measured value). When this measured value is identical to the reference value for evaluation, the sample nucleic acid and the probe perfectly match. That is, the detection target site of the sample nucleic acid can be determined as being of the desired polymorphism (Y). In contrast, when the measured value is lower than the reference value for evaluation, the sample nucleic acid and the probe mismatch. That is, the detection target site of the sample nucleic acid can be determined as having the other polymorphism (X). With such a method, an SNP can be detected, for example, only by subjecting a PCR reaction solution to which such a probe is added to thermal treatment and performing a signal measurement, and it is thus possible to automate a detection device.

However, such detection methods using Tm analysis have problems as follows. Generally, a gene polymorphism is present in the form of a homozygote (for example, X/X or Y/Y) or a heterozygote (for example, X/Y). It is important in the detection of a polymorphism to distinguish between a homozygote (X/X or Y/Y) and a heterozygote (X/Y) and, in the case of a homozygote, to distinguish between an X/X homozygote and a Y/Y homozygote. In the case of a heterozygote, gene polymorphism X and gene polymorphism Y are included, and the difference between these polymorphisms is merely a point mutation, i.e., a difference of one base. Accordingly, the following phenomenon occurs: a probe that fully hybridizes with a sequence that contains one polymorphism (for example, Y) (perfect-match) also hybridizes with a sequence that contains the other polymorphism (X) (single-base mismatch). In a case like this, there is a problem in that, as shown when a melting curve that indicates a relationship between signal intensity and temperature is drawn up based on a Tm analysis, it is difficult to detect a peak on the low-temperature side that indicates a mismatch sequence due to the presence of a peak on the high-temperature side that indicates a perfect-match sequence. That is, even when there is a mismatch sequence in a sample, the presence of a perfect-match sequence makes it difficult to distinguish the mismatch sequence, and thus it may be possible that the detection sensitivity is impaired. Also with respect to homozygotes, the difference between a homozygote (X/X) of a polymorphism X and a homozygote (Y/Y) of a polymorphism Y is likewise due to one base. Therefore, as described above, when it is difficult to distinguish between the peak of a perfect-match and the peak of a mismatch, it is consequently difficult to distinguish between a peak indicating the former (X/X) and a peak indicating the latter (Y/Y). That is, it may be possible to determine whether a sample is a homozygote, but it is likely to be difficult to determine the type of polymorphism.

Recently, antibody drugs that take advantage of the human immune function have been attracting attention in the field of pharmaceuticals. Examples of such antibody drugs include trade-name rituxan (generic name: rituximab), which is a therapeutic agent for malignant lymphoma, trade-name herceptin (generic name: trastuzumab), which is a therapeutic agent for breast cancer, and like agents. However, the strength of human immunity varies from person to person, and this is considered to have an influence on the pharmaceutical effects of such antibody drugs. Gene mutation (for example, SNP) is reported as a factor that has an influence on the pharmaceutical effect of such drugs. In particular, a polymorphism of the FCGR3A gene (Non-Patent Document 1), which is a gene that is involved in immunity, has been reported. This gene codes for FcγRIIIa, a type of fragment C receptor (FcR) of IgG. Hence, when such an antibody drug is used in medical treatment, it is considered useful, for example, to detect polymorphisms (SNPs) in such a gene and then to determine the course of medical treatment, e.g., the dosage of the antibody drug and the change of a therapeutic agent, taking into consideration of the results of the detection.

Non-Patent Document 1: Buillaume Cartron et al., BLOOD, 1 Feb., 2002, Volume 99, Number 3

DISCLOSURE OF INVENTION

For the reasons described above, detection of a FCGR3A gene polymorphism is very important in, for example, medical treatment in which an antibody drug is used. The above-described problems are considered applicable not only to the FCGR3A gene but also to other immune-related genes, for example, the FCGR2A gene, the IL-10 gene, the TNF α gene and the TNF β gene. Hence, an object of the present invention is to provide, with respect to an immune-related gene, a polymorphism detection method that can distinguish in a simple manner and with excellent reliability a polymorphism that has one different base.

In order to achieve the object described above, a polymorphism detection probe of the present invention is composed of at least one oligonucleotide selected from the group consisting of oligonucleotides (A) to (H) below:
(A) at least one oligonucleotide complementary to a region extending from guanine at base 193 to be considered as the first base to any one of the $13^{rd}$ to $21^{st}$ bases in the direction toward the 3' end in the base sequence of SEQ ID NO: 1, with cytosine complementary to the guanine being the 3' end,
(B) at least one oligonucleotide complementary to a region extending from guanine at base 191 to be considered as the first base to any one of the $15^{th}$ to $24^{th}$ bases in the direction toward the 3' end in the base sequence of SEQ ID NO: 2, with cytosine complementary to the guanine being the 3' end,
(C) at least one oligonucleotide complementary to a region extending from guanine at base 311 to be considered as the first base to any one of the $16^{th}$ to $21^{st}$ bases in the direction toward the 5' end in the base sequence of SEQ ID NO: 3, with cytosine complementary to the guanine being the 5' end,
(D) at least one oligonucleotide complementary to a region extending from guanine at base 391 to be considered as the first base to any one of the $16^{th}$ to $22^{nd}$ bases in the direction toward the 3' end in the base sequence of SEQ ID NO: 4, with cytosine complementary to the guanine being the 3' end,
(E) at least one oligonucleotide complementary to a region extending from guanine at base 426 to be considered as the first base to any one of the $15^{th}$ to $24^{th}$ bases in the direction toward the 5' end in the base sequence of SEQ ID NO: 5, with cytosine complementary to the guanine being the 5' end,
(F) at least one oligonucleotide having a sequence identical to that of a region extending from cytosine at base 165 to be considered as the first base to any one of the $16^{th}$ to $27^{th}$ bases in the direction toward the 3' end in the base sequence of SEQ ID NO: 6, with the cytosine being the 3' end,
(G) at least one oligonucleotide complementary to a region extending from guanine at base 394 to be considered as the first base to any one of the $12^{nd}$ to $16^{th}$ bases in the direction toward the 3' end in the base sequence of SEQ ID NO: 7, with cytosine complementary to the guanine being the 3' end, and
(H) at least one oligonucleotide complementary to a region extending from guanine at base 393 to be considered as the first base to any one of the $15^{th}$ to $22^{nd}$ bases in the direction toward the 3' end in the base sequence of SEQ ID NO: 300, with cytosine complementary to the guanine being the 3' end.

The polymorphism detection reagent of the present invention is a reagent for detecting an immune-related gene polymorphism and contains a polymorphism detection probe of the present invention.

The polymorphism detection method of the present invention is a method for detecting an immune-related gene polymorphism and includes steps (1) to (3) as follows:
(1) a step of preparing a reaction system containing a sample nucleic acid for detecting the polymorphism and a polymorphism detection probe of the present invention;
(2) a step of measuring a signal value that indicates the melting state of the hybridization product between the sample nucleic acid and the probe while changing the temperature of the reaction system; and
(3) a step of determining the polymorphism in the sample nucleic acid based on the change in signal value associated with the temperature change.

With the probes of the present invention, specific polymorphisms as described below in connection with the immune-related genes, i.e., the FCGR3A gene, the FCGR2A gene, the IL-10 gene, the TNF α gene and the TNF β gene, can be distinguished in a simple manner and with excellent reliably by Tm analysis. In particular, even when an immune-related gene polymorphism is a heterozygote (X/Y), polymorphism X and polymorphism Y can be distinguished and detected. Moreover, when an immune-related gene polymorphism is a homozygote (X/X or Y/Y), it is also possible to distinguish between homozygote X/X and homozygote Y/Y. As described above, in the detection of a heterozygote (X/Y) by Tm analysis, conventional probes hybridize with a sequence containing one polymorphism (X) as well as a sequence containing the other polymorphism (Y) that is different only in one base, and therefore the signal peaks of both polymorphisms overlap in a melting curve, thereby making it difficult to distinguish between the polymorphisms. In contrast, with the probes of the present invention, signal peaks of both polymorphisms can be sufficiently distant from each other in a melting curve although the probes hybridize with both sequences. Therefore, according to the present invention, a polymorphism that has only one different base can be distinguished and detected in a simple manner. Moreover, according to the present invention, for example, even when two or more types of probes are introduced into a single reaction system, each probe can distinguish a corresponding immune-related gene polymorphism in the single reaction system. Therefore, a plurality of polymorphisms can be detected, for example, using a single reaction system for one sample. Accordingly, since an immune-related gene polymorphism readily can be distinguished with excellent reliability according to the present invention, the results of detection can be reflected also in, for example, a medical treatment with the administration of antibody drugs such as those described above. Therefore, it can be said that the present invention is particularly useful in the medical field and like technical fields.

DESCRIPTION OF THE PREFERRED EMBODIMENTS

Figure 1:
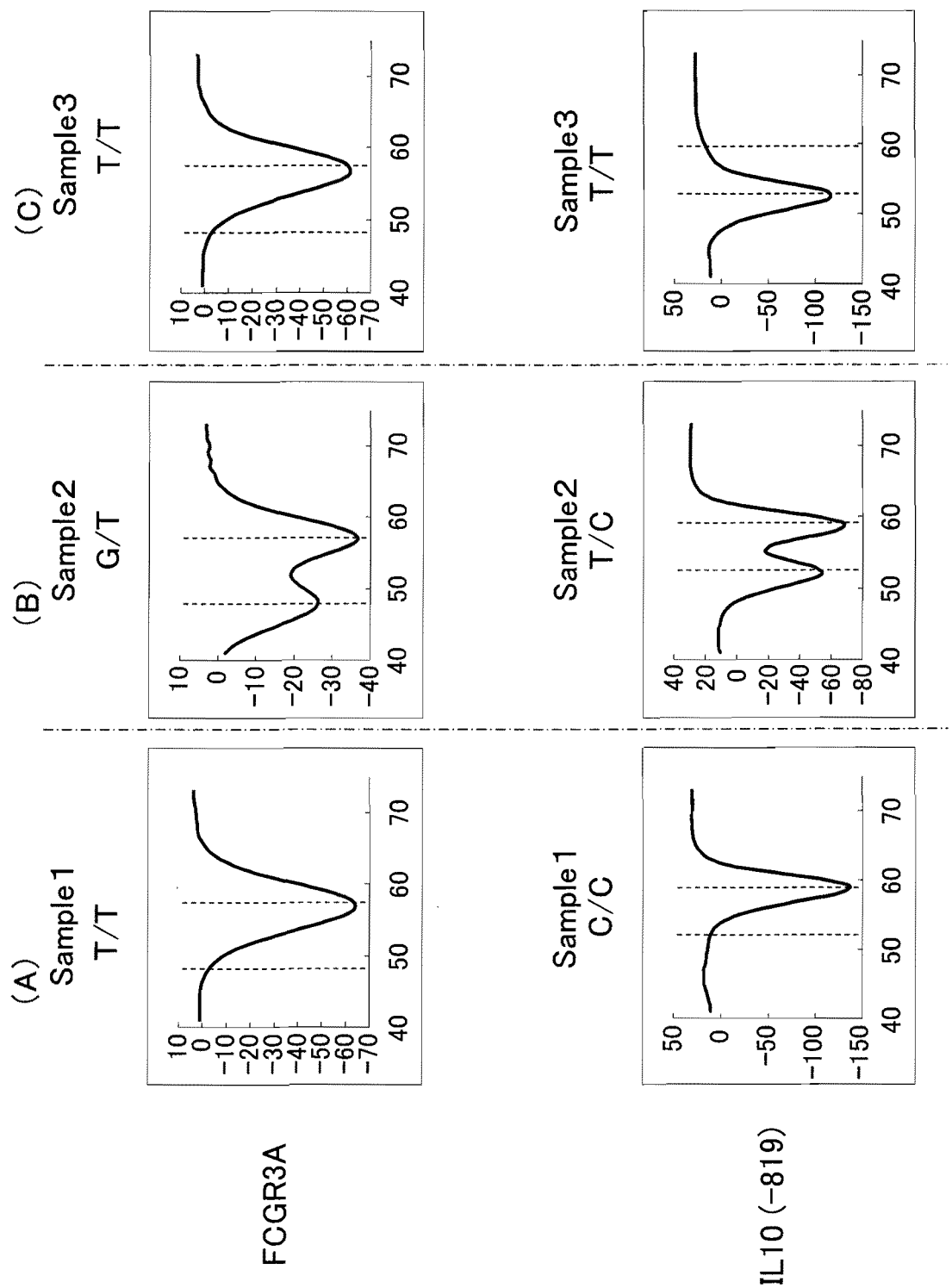
FIG. 1 depicts graphs showing the results of a Tm analysis in Example 1 of the present invention.

In the present specification, a site where a polymorphism to be detected occurs will be called hereinbelow a "detection target site", and a sequence with which a probe can hybridize and that contains such a detection target site will be called a "detection target sequence". Encompassed within such detection target sequences, a detection target sequence that perfectly matches a probe will be called a "perfect-match sequence", and a detection target sequence that mismatches a probe will be called a "mismatch sequence". In the present specification, the term "perfect-match" means that the base of a detection target site is complementary to the corresponding base in a probe, and preferably means that the detection target sequence and the probe are fully complementary to each other. In the present invention, the term "mismatch" means that the base of a detection target site is non-complementary to the corresponding base in a probe, and preferably means that the detection target site and the probe are fully complementary in the sites other than the detection target site. In addition, a nucleic acid, DNA and a gene that have a perfect-match sequence will be called "a "perfect-match nucleic acid", "perfect-match DNA" and "a perfect-match gene", respectively, and a nucleic acid, DNA and a gene that have a mismatch sequence will be called "a mismatch nucleic acid", "mismatch DNA" and "a mismatch gene", respectively. Moreover, a nucleic acid, DNA and a gene on which polymorphism detection is performed will be called "a sample nucleic acid", "sample DNA" and "a sample gene", respectively.

Probes

The polymorphism detection probes of the present invention are, as described above, probes for detecting immune-related gene polymorphisms, and are composed of at least one oligonucleotide selected from the group consisting of items (A) to (H) as follows. The polymorphism detection probes of the present invention may contain, in addition to the following various oligonucleotides, for example, labeling materials or the like as will be described below.

FCGR3A Probe

A probe composed of an oligonucleotide (A) below is a probe for detecting a polymorphism of the FCGR3A gene, which is an immune-related gene. Hereinbelow, this probe will be referred to as an "FCGR3A probe."

(A) at least one oligonucleotide complementary to a region extending from guanine (g) at base 193 to be considered as the first base to any one of the $13^{rd}$ to $21^{st}$ bases in the direction toward the 3' end in the base sequence of SEQ ID NO: 1, with cytosine (c) complementary to the guanine being the 3' end.

The FCGR3A probe of the present invention is a probe for detecting a polymorphism (g/t, ancestral allele "g") of the $201^{st}$ base (k) in the partial sequence of the FCGR3A gene shown in SEQ ID NO. 1. This polymorphism is registered under, for example, the NCBI accession NO. rs396991. In the present invention, this polymorphism will be called hereinbelow an "FCGR3A polymorphism."

The FCGR3A probe of the present invention is complementary to the sense strand (forward strand) of the FCGR3A gene, and hybridization with the sense strand allows the detection of a polymorphism in the sense strand. In the oligonucleotide (A), a complementary base that corresponds to the $201^{st}$ base (k) of SEQ ID NO. 1 is represented as m, and this m is adenine or cytosine. When m is adenine, the probe perfectly matches a polymorphism (t), and when m is cytosine, the probe perfectly matches a polymorphism (g). Therefore, an FCGR3A polymorphism can be detected based on whether the probe perfectly matches or not. Preferably, m is adenine.

Specific examples of the FCGR3A probe are presented in the following table. The probes represented by SEQ ID NOS. 8 to 16 have sequences complementary to regions that include the 201.sup.st base (k) in SEQ ID NO. 1, and the base m is a complementary base that corresponds to the 201.sup.st base (k) in SEQ ID NO. 1. In each of the sequences shown below, the base m may be either adenine (a) or cytosine (c), and it is preferably adenine (a). "Tm (° C.)" in the following table is the Tm (° C.) at which a sequence of the following table is hybridized with a fully complementary sequence, and the value is calculated with parameters such as an oligonucleotide concentration of 0.2 .mu.M and a sodium equivalent (Na eq.) of 50 mM using MELTCALC software (meltcalc.com/) (this also applies hereinbelow). A Tm value, as mentioned above, can be calculated using, for example, the aforementioned MELTCALC software (meltcalc.com/) or the like, and it also can be determined by the nearest neighbor method. Among the probes below, an oligonucleotide (A1) having the base sequence of SEQ ID NO. 14 is preferable.

TABLE 1

| Probe | Sequence | Tm(° C.) | SEQ ID NO. |
|---|---|---|---|
| FCGR3A probes m = a, c | ttttactcccaamaagccccc-(fluorescent material) | 54.6 | 8 |
| | tttactcccaamaagccccc-(fluorescent material) | 54 | 9 |
| | ttactcccaamaagccccc-(fluorescent material) | 53.4 | 10 |
| | tactcccaamaagccccc-(fluorescent material) | 52.7 | 11 |
| | actcccaamaagccccc-(fluorescent material) | 52.9 | 12 |
| | ctcccaamaagccccc-(fluorescent material) | 50.8 | 13 |
| | tcccaamaagccccc-(fluorescent material) | 49.1 | 14 |
| | cccaamaagccccc-(fluorescent material) | 46.9 | 15 |
| | ccaamaagccccc-(fluorescent material) | 42.8 | 16 |

Moreover, the FCGR3A probe of the present invention may be a probe composed of an oligonucleotide (A') that is complementary to the oligonucleotide (A). Thereby, hybridization with the antisense strand (reverse strand) allows the detection of a polymorphism in the antisense strand.

FCGR2A Probes

A probe composed of an oligonucleotide (B) below is a probe for detecting a polymorphism of the FCGR2A gene, which is an immune-related gene. Hereinbelow, this probe will be referred to as an "FCGR2A probe."

(B) at least one oligonucleotide complementary to a region extending from guanine (g) at base 191 to be considered as the first base to any one of the $15^{th}$ to $24^{th}$ bases in the direction toward the 3' end in the base sequence of SEQ ID NO: 2, with cytosine (c) complementary to the guanine being the 3' end.

The FCGR2A probe of the present invention is a probe for detecting a polymorphism (t/c, ancestral allele "t") of the $201^{st}$ base (y) in the partial sequence of the FCGR2A gene shown in SEQ ID NO. 2. This polymorphism is registered under, for example, the NCBI accession NO. rs1801274. This polymorphism will be called hereinbelow an "FCGR2A polymorphism."

The FCGR2A probe of the present invention is complementary to the sense strand (forward strand) of the FCGR2A gene, and hybridization with the sense strand allows the detection of a polymorphism in the sense strand. In the oligonucleotide (B), a complementary base that corresponds to the 201$^{st}$ base (y) of SEQ ID NO. 2 is represented as r, and this r is adenine or guanine. When r is guanine, the probe perfectly matches a polymorphism (c), and when r is adenine, the probe perfectly matches a polymorphism (t). Therefore, an FCGR2A polymorphism can be detected based on whether the probe perfectly matches or not. Preferably, r is adenine.

Specific examples of the FCGR2A probe are presented in the following table. The probes represented by SEQ ID NOS. 17 to 26 have sequences complementary to regions that include the 201$^{st}$ base (y) in SEQ ID NO. 2, and the base r is a complementary base that corresponds to the 201$^{st}$ base (y) in SEQ ID NO. 2. In each of the sequences shown below, the base r may be either adenine (a) or guanine (g), and it is preferably adenine (a). Among the probes below, an oligonucleotide (B1) having the base sequence of SEQ ID NO. 23 is preferable.

example, the NCBI accession NO. rs1800872. This polymorphism will be called hereinbelow an "IL-10 (−592) polymorphism."

The IL-10 (−592) probe of the present invention is complementary to the sense strand of the IL-10 gene, and hybridization with the sense strand allows the detection of a polymorphism in the sense strand. In the oligonucleotide (C), a complementary base that corresponds to the 301$^{st}$ base (m) of SEQ ID NO. 3 is represented as k, and this k is thymine or guanine. When k is thymine, the probe perfectly matches a polymorphism (a), and when k is guanine, the probe perfectly matches a polymorphism (c). Therefore, an IL-10 (−592) polymorphism can be detected based on whether the probe perfectly matches or not. Preferably, k is thymine.

Specific examples of the IL-10 (−592) probe of the present invention are presented in the following table. The probes represented by SEQ ID NOS. 27 to 32 have sequences complementary to regions that include the 301$^{st}$ base (m) in

TABLE 2

| Probe | Sequence | Tm(° C.) | SEQ ID NO. |
|---|---|---|---|
| FCGR2A probes r = a, g | cagaaattctcccrttttggatccc-(fluorescent material) | 55.3 | 17 |
| | agaaattctcccrttttggatccc-(fluorescent material) | 54.1 | 18 |
| | gaaattctcccrttttggatccc-(fluorescent material) | 52.9 | 19 |
| | aaattctcccrttttggatccc-(fluorescent material) | 51.8 | 20 |
| | aattctcccrttttggatccc-(fluorescent material) | 51 | 21 |
| | attctcccrttttggatccc-(fluorescent material) | 50.2 | 22 |
| | ttctcccrttttggatccc-(fluorescent material) | 49.7 | 23 |
| | tctcccrttttggatccc-(fluorescent material) | 48.7 | 24 |
| | ctcccrttttggatccc-(fluorescent material) | 46.8 | 25 |
| | tcccrttttggatccc-(fluorescent material) | 44.7 | 26 |

Moreover, the FCGR2A probe of the present invention may be a probe composed of an oligonucleotide (B') that is complementary to the oligonucleotide (B). Thereby, hybridization with the antisense strand (reverse strand) allows the detection of a polymorphism in the antisense strand.

SEQ ID NO. 3, and the base k is a complementary base that corresponds to the 301$^{st}$ base (m) in SEQ ID NO. 3. In each of the sequences shown below, the base k may be either thymine (t) or guanine (g), and it is preferably thymine (t). Among the probes below, an oligonucleotide (C1) having the base sequence of SEQ ID NO. 30 is preferable.

TABLE 3

| Probe | Sequence | Tm(° C.) | SEQ ID NO. |
|---|---|---|---|
| IL10('1592) probes k = t, g | (fluorescent material)-cttcctacagkacaggcgggg-P | 57.9 | 27 |
| | (fluorescent material)-cttcctacagkacaggcggg-P | 55.7 | 28 |
| | (fluorescent material)-cttcctacagkacaggcgg-P | 53.2 | 29 |
| | (fluorescent material)-cttcctacagkacaggcg-P | 50.6 | 30 |
| | (fluorescent material)-cttcctacagkacaggc-P | 47 | 31 |
| | (fluorescent material)-cttcctacagkacagg-P | 42.7 | 32 |

IL-10 (−592) Probes

A probe composed of an oligonucleotide (C) below is a probe for detecting the polymorphism at the 592$^{nd}$ site of the IL-10 gene, which is an immune-related gene. Hereinbelow, this probe will be referred to as an "IL-10 (−592) probe."

(C) at least one oligonucleotide complementary to a region extending from guanine (G) at base 311 to be considered as the first base to any one of the 16$^{th}$ to 21$^{st}$ bases in the direction toward the 5' end in the base sequence of SEQ ID NO: 3, with cytosine (C) complementary to the guanine being the 5' end.

The IL-10 (−592) probe of the present invention is a probe for detecting a polymorphism (a/c, ancestral allele "c") of the 301$^{st}$ base (m) in the partial sequence of the IL-10 gene shown in SEQ ID NO. 3. This polymorphism is registered under, for Moreover, the IL-10 (−592) probe of the present invention may be a probe composed of an oligonucleotide (C') that is complementary to the oligonucleotide (C). Thereby, hybridization with the antisense strand allows detection of a polymorphism in the antisense strand.

IL-10 (−819) Probes

A probe composed of an oligonucleotide (D) below is a probe for detecting the polymorphism at the 819$^{th}$ site of the IL-10 gene, which is an immune-related gene. Hereinbelow, this probe will be referred to as an "IL-10 (−819) probe." (D) at least one oligonucleotide complementary to a region extending from guanine (G) at base 391 to be considered as the first base to any one of the 16$^{th}$ to 22$^{nd}$ bases in the direction toward the 3' end in the base sequence of SEQ ID NO: 4, with cytosine (C) complementary to the guanine being the 3' end.

The IL-10 (−819) probe of the present invention is a probe for detecting a polymorphism (c/t, ancestral allele "c") of the 401$^{st}$ base (y) in the partial sequence of the IL-10 gene shown in SEQ ID NO. 4. This polymorphism is registered under, for example, the NCBI accession NO. rs1800871. This polymorphism will be called hereinbelow an "IL-10 (−819) polymorphism."

The IL-10 (−819) probe of the present invention is complementary to the sense strand of the IL-10 gene, and hybridization with the sense strand allows the detection of a polymorphism in the sense strand. In the oligonucleotide (D), a complementary base that corresponds to the 401$^{st}$ base (y) of SEQ ID NO. 4 is represented as r, and this r is guanine or adenine. When r is guanine, the probe perfectly matches a polymorphism (c), and when r is adenine, the probe perfectly matches a polymorphism (t). Therefore, a polymorphism can be detected based on whether the probe perfectly matches or not. Preferably, r is guanine.

Specific examples of the IL-10 (−819) probe of the present invention are presented in the following table. The probes represented by SEQ ID NOS. 33 to 39 are composed of sequences complementary to regions that include the 401$^{st}$ base (y) in SEQ ID NO. 4, and the base r is a complementary base that corresponds to the 401$^{st}$ base (y) in SEQ ID NO. 4. In each of the sequences shown below, the base r may be either guanine (g) or adenine (a), and it is preferably guanine (g). Among the probes below, an oligonucleotide (D1) having the base sequence of SEQ ID NO. 36 is preferable.

TABLE 4

| Probe | Sequence | Tm(° C.) | SEQ ID NO. |
|---|---|---|---|
| IL10(−819) probes r = g, a | ggcacagagatrttacatcacc-(fluorescent material) | 55 | 33 |
| | gcacagagatrttacatcacc-(fluorescent material) | 52.8 | 34 |
| | cacagagatrttacatcacc-(fluorescent material) | 49.6 | 35 |
| | acagagatrttacatcacc-(fluorescent material) | 47.9 | 36 |
| | cagagatrttacatcacc-(fluorescent material) | 45.8 | 37 |
| | agagatrttacatcacc-(fluorescent material) | 43.6 | 38 |
| | gagatrttacatcacc-(fluorescent material) | 41.5 | 39 |

Moreover, the IL-10 (−819) probe of the present invention may be a probe composed of an oligonucleotide (D') that is complementary to the oligonucleotide (D). Thereby, hybridization with the antisense strand allows the detection of a polymorphism in the antisense strand.

IL-10 (−1082) Probes

A probe composed of an oligonucleotide (E) below is a probe for detecting the polymorphism at the 1082$^{nd}$ site of the IL-10 gene, which is an immune-related gene. Hereinbelow, this probe will be referred to as an "IL-10 (−1082) probe."

(E) at least one oligonucleotide complementary to a region extending from guanine (G) at base 426 to be considered as the first base to any one of the 15$^{th}$ to 24$^{th}$ bases in the direction toward the 5' end in the base sequence of SEQ ID NO: 5, with cytosine (C) complementary to the guanine being the 5' end.

The IL-10 (−1082) probe of the present invention is a probe for detecting a polymorphism (a/g, ancestral allele "a") of the 414$^{th}$ base (r) in the partial sequence of the IL-10 gene shown in SEQ ID NO. 5. This polymorphism is registered under, for example, the NCBI accession NO. rs1800896. Hereinbelow, this polymorphism will be called an "IL-10 (−1082) polymorphism."

The IL-10 (−1082) probe of the present invention is complementary to the sense strand of the IL-10 gene, and hybridization with the sense strand allows the detection of a polymorphism in the sense strand. In the oligonucleotide (E), a base that is complementary to the 414$^{th}$ base (r) of SEQ ID NO. 5 is represented as y, and this y is thymine or cytosine. When y is thymine, the probe perfectly matches a polymorphism (a), and when y is cytosine, the probe perfectly matches a polymorphism (g). Therefore, a polymorphism can be detected based on whether the probe perfectly matches or not. Preferably, y is cytosine.

Specific examples of the IL-10 (−1082) probe of the present invention are presented in the following table. The probes represented by SEQ ID NOS. 40 to 49 have sequences complementary to regions that include the 414$^{th}$ base (r) in SEQ ID NO. 5, and the base y is a base complementary to the 414$^{th}$ base (r) in SEQ ID NO. 5. In each of the sequences shown below, the base y may be either thymine (t) or cytosine (c), and it is preferably cytosine (c). Among the probes below, an oligonucleotide (E1) having the base sequence of SEQ ID NO. 47 is preferable.

TABLE 5

| Probe | Sequence | Tm(° C.) | SEQ ID NO. |
|---|---|---|---|
| IL10(−1082) probes y = t, c | (fluorescent material)-ccctacttccccytcccaaagaag-P | 59.5 | 40 |
| | (fluorescent material)-ccctacttccccytcccaaagaa-P | 58.9 | 41 |
| | (fluorescent material)-ccctacttccccytcccaaaga-P | 58.5 | 42 |
| | (fluorescent material)-ccctacttccccytcccaaag-P | 57.4 | 43 |
| | (fluorescent material)-ccctacttccccytcccaaa-P | 56.5 | 44 |
| | (fluorescent material)-ccctacttccccytcccaa-P | 56 | 45 |
| | (fluorescent material)-ccctacttccccytccca-P | 55.4 | 46 |
| | (fluorescent material)-ccctacttccccytccc-P | 53.5 | 47 |
| | (fluorescent material)-ccctacttccccytcc-P | 50.4 | 48 |
| | (fluorescent material)-ccctacttccccytc-P | 46.9 | 49 |

Moreover, the IL-10 (−1082) probe of the present invention may be a probe composed of an oligonucleotide (E') that is complementary to the oligonucleotide (E). Thereby, hybridization with the antisense strand allows detection of a polymorphism in the antisense strand.

IL-10(−3575) Probes

A probe composed of an oligonucleotide (F) below is a probe for detecting the polymorphism at the $3575^{th}$ site of the IL-10 gene, which is an immune-related gene. Hereinbelow, this probe will be referred to as an "IL-10 (−3575) probe."

(F) at least one oligonucleotide having a sequence identical to that of a region extending from cytosine (C) at base 165 to be considered as the first base to any one of the $16^{th}$ to $27^{th}$ bases in the direction toward the 3' end in the base sequence of SEQ ID NO: 6, with the cytosine (C) being the 3' end.

The IL-10 (−3575) probe of the present invention is a probe for detecting a polymorphism (a/t, ancestral allele "t") of the $179^{th}$ base (w) in the partial sequence of the IL-10 gene shown in SEQ ID NO. 6. This polymorphism is registered under, for example, the NCBI accession NO. rs1800890. This polymorphism will be called hereinbelow an "IL-10 (−3575) polymorphism."

The IL-10 (−3575) probe of the present invention is complementary to the antisense strand of the IL-10 gene, and hybridization with the antisense strand allows the detection of a polymorphism in the antisense strand. In the oligonucleotide (F), a base that corresponds to the $179^{th}$ base (w) of SEQ ID NO. 6 is represented as w, and this w is thymine or adenine. When w is thymine, the probe perfectly matches a polymorphism (a) of the antisense strand, and when w is adenine, the probe perfectly matches a polymorphism (t) of the antisense strand. Therefore, a polymorphism can be detected based on whether the probe perfectly matches or not. Preferably, w is thymine.

Specific examples of the IL-10 (−3575) probe of the present invention are presented in the following table. The probes represented by SEQ ID NOS. 50 to 61 have sequences identical to regions that include the $179^{th}$ base (w) in SEQ ID NO. 6, and the base w is a base that corresponds to the $179^{th}$ base (w) in SEQ ID NO. 6. In the sequences shown below, the base w may be either thymine (t) or adenine (a), and it is preferably thymine (t). Among the probes below, an oligonucleotide (F1) having the base sequence of SEQ ID NO. 57 is preferable.

TNF α (−308) Probes

A probe composed of an oligonucleotide (G) below is a probe for detecting a polymorphism of the TNF α gene, which is an immune-related gene. Hereinbelow, this probe will be referred to as a "TNF α (−308) probe" or a "TNF α probe."

(G) at least one oligonucleotide complementary to a region extending from guanine (G) at base 394 to be considered as the first base to any one of the $12^{nd}$ to $16^{th}$ bases in the direction toward the 3' end in the base sequence of SEQ ID NO: 7, with cytosine (C) complementary to the guanine being the 3' end.

The TNF α probe of the present invention is a probe for detecting a polymorphism (a/g, ancestral allele "g") of the $401^{st}$ base (r) in the partial sequence of the TNF α gene shown in SEQ ID NO. 7. This polymorphism is registered under, for example, the NCBI accession NO. rs1800629. Hereinbelow, this polymorphism will be called a "TNF α (−308) polymorphism" or "TNF α polymorphism."

The TNF α probe of the present invention is complementary to the sense strand of the TNF α gene, and hybridization with the sense strand allows the detection of a polymorphism in the sense strand. In the oligonucleotide (G), a base that is complementary to the $401^{st}$ base (r) of SEQ ID NO. 7 is represented as y, and this y is thymine or cytosine. When y is thymine, the probe perfectly matches a polymorphism (a), and when y is cytosine, the probe perfectly matches a polymorphism (g). Therefore, a polymorphism can be detected based on whether the probe perfectly matches or not. Preferably, y is cytosine.

Specific examples of the TNF α probe of the present invention are presented in the following table. The probes represented by SEQ ID NOS. 62 to 66 have sequences complementary to regions that include the $401^{st}$ base (r) in SEQ ID NO. 7, and the base y is a base complementary to the $401^{st}$ base (r) in SEQ ID NO. 7. In the sequences shown below, the base y may be either thymine (t) or cytosine (c), and it is

TABLE 6

| Probe | Sequence | Tm(° C.) | SEQ ID NO. |
|---|---|---|---|
| IL10(−3575) probes w = t, a | (fluorescent material)-cccactggaaaaatwcatttaaaatca-P | 53.2 | 50 |
| | (fluorescent material)-cccactggaaaaatwcatttaaaatc-P | 51.9 | 51 |
| | (fluorescent material)-cccactggaaaaatwcatttaaaat-P | 50.9 | 52 |
| | (fluorescent material)-cccactggaaaaatwcatttaaaa-P | 50.5 | 53 |
| | (fluorescent material)-cccactggaaaaatwcatttaaa-P | 49.8 | 54 |
| | (fluorescent material)-cccactggaaaaatwcatttaa-P | 49 | 55 |
| | (fluorescent material)-cccactggaaaaatwcattta-P | 48.2 | 56 |
| | (fluorescent material)-cccactggaaaaatwcattt-P | 48.2 | 57 |
| | (fluorescent material)-cccactggaaaaatwcatt-P | 47.3 | 58 |
| | (fluorescent material)-cccactggaaaaatwcat-P | 46.3 | 59 |
| | (fluorescent material)-cccactggaaaaatwca-P | 45.4 | 60 |
| | (fluorescent material)-cccactggaaaaatwc-P | 43 | 61 |

Moreover, the IL-10 (−3575) probe of the present invention may be a probe composed of an oligonucleotide (F') that is complementary to the oligonucleotide (F). Thereby, hybridization with the sense strand allows the detection of a polymorphism in the sense strand.

preferably cytosine (c). Among the probes below, an oligonucleotide (G1) composed of the base sequence of SEQ ID NO. 64 is preferable.

TABLE 7

| Probe | Sequence | Tm(° C.) | SEQ ID NO. |
|---|---|---|---|
| TNF α (−308) probes | ccccgtccycatgccc-(fluorescent material) | 58.6 | 62 |
| | cccgtccycatgccc-(fluorescent material) | 55.7 | 63 |

TABLE 7-continued

| Probe | Sequence | Tm(° C.) | SEQ ID NO. |
|---|---|---|---|
| y = t, c | ccgtccycatgccc-(fluorescent material) | 52.5 | 64 |
| | cgtccycatgccc-(fluorescent material) | 48.8 | 65 |
| | gtccycatgccc-(fluorescent material) | 43.6 | 66 |

Moreover, the TNF α probe of the present invention may be a probe composed of an oligonucleotide (G') that is complementary to the oligonucleotide (G). Thereby, hybridization with the antisense strand allows the detection of a polymorphism in the antisense strand.

TNF β Probes

A probe composed of an oligonucleotide (H) below is a probe for detecting a polymorphism of the TNF β gene, which is an immune-related gene. Hereinbelow, this probe will be referred to as a "TNF β (+252) probe" or a "TNF β probe."

(H) at least one oligonucleotide complementary to a region extending from guanine (G) at base 393 to be considered as the first base to any one of the $15^{th}$ to $22^{nd}$ bases in the direction toward the 3' end in the base sequence of SEQ ID NO: 300, with cytosine (C) complementary to the guanine being the 3' end.

The TNF β primer of the present invention is a probe for detecting a polymorphism (t/c) of the $401^{st}$ base (y) in the partial sequence of the TNF β gene shown in SEQ ID NO. 300. This polymorphism is registered under, for example, the NCBI accession NO. rs909253. Hereinbelow, this polymorphism will be called a "TNF β (+252) polymorphism" or a "TNF β polymorphism."

The TNF β probe of the present invention is complementary to the sense strand of the TNF β gene, and hybridization with the sense strand allows the detection of a polymorphism in the sense strand. In the oligonucleotide (H), a base that is complementary to the $401^{st}$ base (y) of SEQ ID NO. 300 is represented as r, and this r is adenine or guanine. When r is guanine, the probe perfectly matches a polymorphism (c), and when r is adenine, the probe perfectly matches a polymorphism (t). Therefore, a polymorphism can be detected based on whether the probe perfectly matches or not. Preferably, r is guanine.

Specific examples of the TNF β probe of the present invention are presented in the following table. The probes represented by SEQ ID NOS. 301 to 308 have sequences complementary to regions that include the $401^{th}$ base (y) in SEQ ID NO. 300, and the base r is a base complementary to the $401^{st}$ base (y) in SEQ ID NO. 300. In each of the sequences shown below, the base r may be either adenine (a) or guanine (g), and it is preferably guanine (g). Among the probes below, an oligonucleotide (H1) having the base sequence of SEQ ID NO. 306 or SEQ ID NO. 307 is preferable.

Moreover, the TNF β probe of the present invention may be a probe composed of an oligonucleotide (H') that is complementary to the oligonucleotide (H). Thereby, hybridization with the antisense strand allows the detection of a polymorphism in the antisense strand.

The probes of the present invention include probes that are composed of base sequences in which one or more bases are deleted, substituted or added at base sites other than the sites corresponding to the detection target sites in the oligonucleotides described above, and include probes that are composed of oligonucleotides that can hybridize with the detection target sequences.

The probes of the present invention preferably are labeled probes in which a labeling material is bonded to an aforementioned oligonucleotide. Examples of the labeled probes include a labeled probe that gives a signal when alone and that does not give any signal when forming a hybrid and a labeled probe that does not give any signal when alone and that gives a signal when forming a hybrid. The former probe does not give any signal when forming a hybrid (double-strand nucleic acid) with a detection target sequence, and gives a signal when the probe is liberated by heating. Moreover, the latter probe gives a signal when forming a hybrid (double-strand nucleic acid) with a detection target sequence, and the signal is diminished (quenched) when the probe is liberated by heating.

The labeling material is not limited and examples include fluorescent dyes (fluorophores). A probe that is labeled with a fluorescent dye, that emits fluorescence when alone and whose fluorescence is reduced (for example, quenched) when forming a hybrid is preferable as a specific example of the labeled probe. Probes that take advantage of such a fluorescence quenching phenomenon are called fluorescence quenching probes. It is preferable that in such a labeled probe the 3' end or the 5' end of an oligonucleotide is labeled with a fluorescent dye, and it is more preferable that, of the 3' end and the 5' end, the nucleotide end whose base is cytosine is labeled. In this case, it is preferable that, in connection with a detection target sequence with which the labeled probe hybridizes, the base sequence of the labeled probe is designed such that the base that forms a pair with the end-base cytosine of the labeled probe or the base that is located 1 to 3 bases distant from the base that forms a pair is guanine. Such probes generally are referred to as guanine-quenching probes and known as so-called QProbes (registered trademark). When such a guanine-quenching probe hybridizes with a detection target sequence, the guanine-quenching probe exhibits a phenomenon in which the end cytosine that is labeled with a

TABLE 8

| Probe | Sequence | Tm(° C.) | SEQ ID NO. |
|---|---|---|---|
| TNF β (+252) | tgtttctgccatgrttcctctc-(fluorescent material) | 56.4 | 301 |
| probes | gtttctgccatgrttcctctc-(fluorescent material) | 54.9 | 302 |
| r = a, g | tttctgccatgrttcctctc-(fluorescent material) | 53.6 | 303 |
| | ttctgccatgrttcctctc-(fluorescent material) | 52.9 | 304 |
| | tctgccatgrttcctctc-(fluorescent material) | 52.2 | 305 |
| | ctgccatgrttcctctc-(fluorescent material) | 50.6 | 306 |
| | tgccatgrttcctctc-(fluorescent material) | 48.9 | 307 |
| | gccatgrttcctctc-(fluorescent material) | 46.5 | 308 | fluorescent dye nears the guanine present in the detection targeting sequence, and the fluorescence of the fluorescent dye thereby becomes weak (the intensity of fluorescence is reduced).

The fluorescent dyes are not limited and examples include fluoresceins, phosphors, rhodamine, polymethine dye derivatives, etc., and examples of commercially available fluorescent dyes include BODIPY FL (trade name, manufactured by Molecular Probes), FluorePrime (trade name, manufactured by Amersham Pharmacia), Fluoredite (trade name, manufactured by Millipore Corporation), FAM (manufactured by ABI), Cy3 and Cy5 (manufactured by Amersham Pharmacia), TAMRA (manufactured by Molecular Probes), Pacific Blue (manufactured by Becton, Dickinson and Company), etc. The conditions for detecting a probe are not particularly limited and can be determined suitably according to the fluorescent dye to be used. For example, Pacific Blue can be detected with a detection wavelength of 450 to 480 nm, TAMRA can be detected with a detection wavelength of 585 to 700 nm, and BODIPY FL can be detected with a detection wavelength of 515 to 555 nm. With the use of such a probe, hybridization and the dissociation thereof can be readily checked according to a change in signal.

Moreover, in the probes of the present invention, a phosphate group may be added to, for example, the 3' end. As described below, a sample nucleic acid can be prepared according to a nucleic acid amplification method such as PCR. In this instance, a probe of the present invention can be concomitantly present in the reaction system of the nucleic acid amplification reaction. In such a case, addition of a phosphate group to the 3' end of the probe sufficiently can prevent the elongation of the probe itself that could occur due to the nucleic acid amplification reaction. The same effect can be attained also by adding a labeling material as described above to the 3' end.

The probes of the present invention are each applicable to the detection of polymorphisms in various immune-related genes. In the detection of a polymorphism, one type of the probe of the present invention may be used to detect only one type of polymorphism, and two or more types of the probe may be used to detect two or more types of polymorphism. When two or more types of the probe of the present invention are used, for example, two or more types of polymorphism can be detected using a single reaction system in which the two or more types of the probe are concomitantly present. In this case, it is preferable to label each probe with a fluorescent dye that has a different detection condition.

In connection with the detection of polymorphisms using the probes of the present invention, detection methods are not at all limited insofar as they take advantage of the hybridization between the detection target sequences and the probes. A polymorphism detection method that uses a Tm analysis will be described below as an example of a method in which a probe of the present invention is applied.

Polymorphism Detection Method

The polymorphism detection method of the present invention is, as described above, a method for detecting an immune-related gene polymorphism and includes steps (1) to (3) as follows. The polymorphism detection method of the present invention uses a probe of the present invention, and any other configurations and conditions are not limited by the following description.

(1) A step of providing a reaction system containing a sample nucleic acid for detecting a polymorphism and a polymorphism detection probe of the present invention;

(2) A step of measuring a signal value that indicates the melting state of the hybridization product between the sample nucleic acid and the probe while changing the temperature of the reaction system; and (3) A step of determining the polymorphism in the sample nucleic acid based on the change in signal value associated with the temperature change.

One or more types of the probe of the present invention may be used in the polymorphism detection method of the present invention as described above. In the former case, a polymorphism of one desired type can be detected in one reaction system and, in the latter case, the addition of two or more types of the probe of the present invention to a reaction system allows the detection of polymorphisms of two or more desired types that correspond to the respective probes in one reaction system. When two or more types of polymorphisms are to be detected in one reaction system, a combination of probes of the present invention is not particularly limited, and the following combinations can be mentioned as examples:

(1) A combination of the FCGR3A probe and the IL-10 (−819) probe, and preferably a combination of a probe containing the sequence of SEQ ID NO. 14 and a probe containing the sequence of SEQ ID NO. 36;

(2) A combination of the FCGR2A probe, the IL-10 (−592) probe and the TNF α (−308) probe, and preferably a combination of a probe containing the sequence of SEQ ID NO. 23, a probe containing the sequence of SEQ ID NO. 30 and a probe containing the sequence of SEQ ID NO. 64;

(3) A combination of the IL-10 (−1082) probe and the IL-10 (−3575) probe, and preferably a combination of a probe containing the sequence of SEQ ID NO. 47 and a primer containing the sequence of SEQ ID NO. 57; and (4) A combination of the IL-10 (−592) probe and the IL-10 (−1082) probe, and preferably a combination of a probe containing the sequence of SEQ ID NO. 30 and a probe containing the sequence of SEQ ID NO. 47.

When two or more types of the probe are introduced into one reaction system, it is preferable that each probe is labeled with a labeling material that has a different detection condition. It is thus possible to detect two or more types of polymorphisms in a simple manner using a single reaction system merely by changing detection conditions.

In the present invention, the aforementioned sample nucleic acid may be a single-strand nucleic acid or double-strand nucleic acid. When the sample nucleic acid is a double-strand nucleic acid, it is preferable that the step (2) includes a step of dissociating the double-strand sample nucleic acid by heating the reaction system. The dissociation of the double-strand nucleic acid into a single strand nucleic acid allows hybridization with a probe of the present invention.

In the present invention, the nucleic acid may be, for example, a nucleic acid originally present in a biological sample, or may be an amplification product amplified according to a nucleic acid amplification method using the nucleic acid as a template nucleic acid because the accuracy of detection can be enhanced. The amplification product may be, for example, an amplification product produced using DNA present in a biological sample as a template, or an amplification product produced using cDNA as a template that is synthesized by RT-PCR from RNA such as total RNA or mRNA present in a biological sample.

When the sample nucleic acid is such an amplification product, a reaction system that contains a probe of the present invention and an amplification product may be provided in the step (1), for example, using an amplification product that is provided in advance, or a reaction system that contains a probe and an amplification product may be provided by amplifying the desired amplification product from a template nucleic acid according to a nucleic acid amplification method in the presence of a probe of the present invention. In the latter case, it is preferable that the step (1) includes the step (1a) below:

(1a) a step of generating, in a reaction system containing a probe, an amplification product that serves as a sample nucleic acid from a template nucleic acid according to a nucleic acid amplification method.

The nucleic acid amplification method is not limited and examples include PCR (polymerase chain reaction), NASBA (nucleic acid sequence-based amplification), TMA (transcription-mediated amplification), SDA (strand displacement amplification), etc., with PCR being particularly preferable.

In the step (1a), it is preferable to use a primer for amplifying a sequence containing a polymorphism to be detected in an aforementioned immune-related gene. The sequence of the primer is not particularly limited and is sufficient insofar as it can amplify the detection target sequence containing the detection target site and it can be suitably arranged according to, for example, the detection target sequence and sequences in its vicinity using a known method. The length of the primer is not particularly limited, and can be set to a commonly used length such as, for example, 10 to 30 mer. When two or more types of polymorphisms are to be detected as described above, primers to amplify detection target sequences that are associated with respective polymorphisms may be used together. Moreover, the presence of such primers concomitantly in a single reaction system allows two or more types of detection target sequences to be amplified simultaneously.

For example, either a forward primer (hereinafter also referred to as an "F primer") that amplifies the sense strand of a gene or a reverse primer (hereinafter also referred to as an "R primer") that amplifies the antisense strand is usable as an aforementioned primer, and it is preferable to use a primer set containing both primers as a pair. Examples of such primer sets are given below. These are illustrative and do not limit the present invention.

FCGR3A Primer Set (a)

In connection with the detection of an FCGR3A polymorphism, an example of a primer set is a primer set (a) that contains a forward primer composed of an oligonucleotide (F1) below and a reverse primer composed of an oligonucleotide (R1) below.

(F1) at least one oligonucleotide having a sequence identical to that of a region extending from cytosine (c) at base 173 to be considered as the first base to any one of the $27^{th}$ to $46^{th}$ bases in the direction toward the 5' end in the base sequence of SEQ ID NO: 1, with the cytosine (c) being the 3' end, and (R1) at least one oligonucleotide complementary to a region extending from adenine (a) at base 307 to be considered as the first base to any one of the $23^{rd}$ to $29^{th}$ bases in the direction toward the 3' end in the base sequence of SEQ ID NO: 1, with thymine (t) complementary to the adenine (a) at base 307 being the 3' end.

Specific examples of forward primers and reverse primers are given below, but the present invention is not limited by the examples. Moreover, combinations of the forward primers and the reverse primers are not at all limited and, among others, a primer set containing a forward primer composed of the base sequence of SEQ ID NO. 77 and a reverse primer composed of the base sequence of SEQ ID NO. 97 is particularly preferable.

TABLE 9

| Primer | Sequence | Tm(° C.) | SEQ ID NO. |
| --- | --- | --- | --- |
| FCGR3A F primers | tcatcataattctgacttctacattccaaaagccacactcaaagac | 64.3 | 67 |
| | catcataattctgacttctacattccaaaagccacactcaaagac | 63.9 | 68 |
| | atcataattctgacttctacattccaaaagccacactcaaagac | 63.5 | 69 |
| | tcataattctgacttctacattccaaaagccacactcaaagac | 63.6 | 70 |
| | cataattctgacttctacattccaaaagccacactcaaagac | 63.1 | 71 |
| | ataattctgacttctacattccaaaagccacactcaaagac | 62.7 | 72 |
| | taattctgacttctacattccaaaagccacactcaaagac | 62.7 | 73 |
| | aattctgacttctacattccaaaagccacactcaaagac | 63 | 74 |
| | attctgacttctacattccaaaagccacactcaaagac | 63 | 75 |
| | ttctgacttctacattccaaaagccacactcaaagac | 63 | 76 |
| | tctgacttctacattccaaaagccacactcaaagac | 62.9 | 77 |
| | ctgacttctacattccaaaagccacactcaaagac | 62.3 | 78 |
| | tgacttctacattccaaaagccacactcaaagac | 62 | 79 |
| | gacttctacattccaaaagccacactcaaagac | 61.2 | 80 |
| | acttctacattccaaaagccacactcaaagac | 60.8 | 81 |
| | cttctacattccaaaagccacactcaaagac | 59.9 | 82 |
| | ttctacattccaaaagccacactcaaagac | 59.4 | 83 |
| | tctacattccaaaagccacactcaaagac | 59.2 | 84 |
| | ctacattccaaaagccacactcaaagac | 58.3 | 85 |
| | tacattccaaaagccacactcaaagac | 57.7 | 86 |
| FCGR3A R primers | aatcaggaatctcctcccaactcaacttcccagtgtgat | 66.3 | 87 |
| | atcaggaatctcctcccaactcaacttcccagtgtgat | 66.4 | 88 |
| | tcaggaatctcctcccaactcaacttcccagtgtgat | 66.5 | 89 |
| | caggaatctcctcccaactcaacttcccagtgtgat | 66 | 90 |
| | aggaatctcctcccaactcaacttcccagtgtgat | 65.6 | 91 |
| | ggaatctcctcccaactcaacttcccagtgtgat | 65 | 92 |
| | gaatctcctcccaactcaacttcccagtgtgat | 63.8 | 93 |
| | aatctcctcccaactcaacttcccagtgtgat | 63.5 | 94 |
| | atctcctcccaactcaacttcccagtgtgat | 63.4 | 95 |
| | tctcctcccaactcaacttcccagtgtgat | 63.5 | 96 |
| | ctcctcccaactcaacttcccagtgtgat | 62.8 | 97 |
| | tcctcccaactcaacttcccagtgtgat | 62.4 | 98 |
| | cctcccaactcaacttcccagtgtgat | 61.6 | 99 |
| | ctcccaactcaacttcccagtgtgat | 60 | 100 |
| | tcccaactcaacttcccagtgtgat | 59.4 | 101 |
| | cccaactcaacttcccagtgtgat | 58.4 | 102 |
| | ccaactcaacttcccagtgtgat | 56.5 | 103 |

FCGR2A Primer Set (b)

In connection with the detection of an FCGR2A polymorphism, an example of a primer set is a primer set (b) that contains a forward primer composed of an oligonucleotide (F2) below and a reverse primer composed of an oligonucleotide (R2) below.

A primer set containing a forward primer composed of an oligonucleotide (F2) below and a reverse primer composed of an oligonucleotide (R2) below: (F2) at least one oligonucleotide having a sequence identical to that of a region extending from guanine (g) at base 189 to be considered as the first base to any one of the $23^{rd}$ to $38^{th}$ bases in the direction toward the 5' end in the base sequence of SEQ ID NO: 2, with the guanine (g) being the 3' end, and (R2) at least one oligonucleotide complementary to a region extending from guanine (g) at base 206 to be considered as the first base to any one of the $31^{st}$ to $48^{th}$ bases in the direction toward the 3' end in the base sequence of SEQ ID NO: 2, with cytosine (c) complementary to the guanine (g) at base 206 being the 3' end.

Specific examples of forward primers and reverse primers are given below, but the present invention is not limited by the examples. Moreover, combinations of the forward primers and the reverse primers are not at all limited and, among others, a primer set containing an F2 primer composed of the base sequence of SEQ ID NO. 132 and an R2 primer composed of the base sequence of SEQ ID NO. 114 is particularly preferable.

IL-10 (−592) Primer Set (c)

In connection with the detection of an IL-10 (−592) polymorphism, an example of a primer set is a primer set (c) that contains a forward primer composed of an oligonucleotide (F3) below and a reverse primer composed of an oligonucleotide (R3) below.

(F3) at least one oligonucleotide having a sequence identical to that of a region extending from cytosine (c) at base 291 to be considered as the first base to any one of the $23^{rd}$ to $41^{st}$ bases in the direction toward the 5' end in the base sequence of SEQ ID NO: 3, with the cytosine (c) being the 3' end, and (R3) at least one oligonucleotide complementary to a region extending from guanine (g) at base 311 to be considered as the first base to any one of the $27^{th}$ to $41^{st}$ bases in the direction toward the 3' end in the base sequence of SEQ ID NO: 3, with cytosine (c) complementary to the guanine (g) at base 311 being the 3' end.

Specific examples of forward primers and reverse primers are given below, but the present invention is not limited by the examples. Moreover, combinations of the forward primers and the reverse primers are not at all limited and, among others, a primer set containing a forward primer composed of the base sequence of SEQ ID NO. 148 and a reverse primer composed of the base sequence of SEQ ID NO. 167 is particularly preferable.

TABLE 10

| Primer | Sequence | Tm(° C.) | SEQ ID NO. |
|---|---|---|---|
| FCGR2A F primers | accactgtgactgtggtttgcttgtgggatggagaagg | 68.9 | 122 |
| | ccactgtgactgtggtttgcttgtgggatggagaagg | 68.3 | 123 |
| | cactgtgactgtggtttgcttgtgggatggagaagg | 67.3 | 124 |
| | actgtgactgtggtttgcttgtgggatggagaagg | 67 | 125 |
| | ctgtgactgtggtttgcttgtgggatggagaagg | 66.3 | 126 |
| | tgtgactgtggtttgcttgtgggatggagaagg | 66.1 | 127 |
| | gtgactgtggtttgcttgtgggatggagaagg | 65.4 | 128 |
| | tgactgtggtttgcttgtgggatggagaagg | 65 | 129 |
| | gactgtggtttgcttgtgggatggagaagg | 64.1 | 130 |
| | actgtggtttgcttgtgggatggagaagg | 63.8 | 131 |
| | ctgtggtttgcttgtgggatggagaagg | 62.9 | 132 |
| | tgtggtttgcttgtgggatggagaagg | 62.5 | 133 |
| | gtggtttgcttgtgggatggagaagg | 61.5 | 134 |
| | tggtttgcttgtgggatggagaagg | 60.7 | 135 |
| | ggtttgcttgtgggatggagaagg | 59.6 | 136 |
| | gtttgcttgtgggatggagaagg | 57.7 | 137 |
| FCGR2A R primers | cctctggtcaaggtcacattcttccagaatggaaaatcccagaaattc | 67.2 | 104 |
| | ctctggtcaaggtcacattcttccagaatggaaaatcccagaaattc | 66.5 | 105 |
| | tctggtcaaggtcacattcttccagaatggaaaatcccagaaattc | 66.3 | 106 |
| | ctggtcaaggtcacattcttccagaatggaaaatcccagaaattc | 65.9 | 107 |
| | tggtcaaggtcacattcttccagaatggaaaatcccagaaattc | 65.7 | 108 |
| | ggtcaaggtcacattcttccagaatggaaaatcccagaaattc | 65.2 | 109 |
| | gtcaaggtcacattcttccagaatggaaaatcccagaaattc | 64.3 | 110 |
| | tcaaggtcacattcttccagaatggaaaatcccagaaattc | 63.9 | 111 |
| | caaggtcacattcttccagaatggaaaatcccagaaattc | 63.4 | 112 |
| | aaggtcacattcttccagaatggaaaatcccagaaattc | 63 | 113 |
| | aggtcacattcttccagaatggaaaatcccagaaattc | 62.9 | 114 |
| | ggtcacattcttccagaatggaaaatcccagaaattc | 62.3 | 115 |
| | gtcacattcttccagaatggaaaatcccagaaattc | 61.2 | 116 |
| | tcacattcttccagaatggaaaatcccagaaattc | 60.6 | 117 |
| | cacattcttccagaatggaaaatcccagaaattc | 60 | 118 |
| | acattcttccagaatggaaaatcccagaaattc | 59.4 | 119 |
| | cattcttccagaatggaaaatcccagaaattc | 58.4 | 120 |
| | attcttccagaatggaaaatcccagaaattc | 57.7 | 121 |

TABLE 11

| Primer | Sequence | Tm(° C.) | SEQ ID NO. |
|---|---|---|---|
| IL10(-592) F primers | atgaaatcggggtaaaggagcctggaacacatcctgtgac | 68.2 | 138 |
| | tgaaatcggggtaaaggagcctggaacacatcctgtgac | 68.3 | 139 |
| | gaaatcggggtaaaggagcctggaacacatcctgtgac | 67.7 | 140 |
| | aaatcggggtaaaggagcctggaacacatcctgtgac | 67.6 | 141 |
| | aatcggggtaaaggagcctggaacacatcctgtgac | 67.7 | 142 |
| | atcggggtaaaggagcctggaacacatcctgtgac | 67.7 | 143 |
| | tcggggtaaaggagcctggaacacatcctgtgac | 67.9 | 144 |
| | cggggtaaaggagcctggaacacatcctgtgac | 67.4 | 145 |
| | ggggtaaaggagcctggaacacatcctgtgac | 66.1 | 146 |
| | gggtaaaggagcctggaacacatcctgtgac | 64.9 | 147 |
| | ggtaaaggagcctggaacacatcctgtgac | 63.6 | 148 |
| | gtaaaggagcctggaacacatcctgtgac | 62.2 | 149 |
| | taaaggagcctggaacacatcctgtgac | 61.6 | 150 |
| | aaaggagcctggaacacatcctgtgac | 62.1 | 151 |
| | aaggagcctggaacacatcctgtgac | 61.9 | 152 |
| | aggagcctggaacacatcctgtgac | 61.8 | 153 |
| | aggagcctggaacacatcctgtgac | 60.9 | 154 |
| | ggagcctggaacacatcctgtgac | 59 | 155 |
| | gagcctggaacacatcctgtgac | 58.3 | 156 |
| IL10(-592) R primers | gttcccaagcagcccttccattttactttccagagactggc | 68.8 | 157 |
| | ttcccaagcagcccttccattttactttccagagactggc | 68.6 | 158 |
| | tcccaagcagcccttccattttactttccagagactggc | 68.7 | 159 |
| | cccaagcagcccttccattttactttccagagactggc | 68.2 | 160 |
| | ccaagcagcccttccattttactttccagagactggc | 67.2 | 161 |
| | caagcagcccttccattttactttccagagactggc | 66.2 | 162 |
| | aagcagcccttccattttactttccagagactggc | 65.9 | 163 |
| | agcagcccttccattttactttccagagactggc | 65.9 | 164 |
| | gcagcccttccattttactttccagagactggc | 65.3 | 165 |
| | cagcccttccattttactttccagagactggc | 63.8 | 166 |
| | agcccttccattttactttccagagactggc | 63.3 | 167 |
| | gcccttccattttactttccagagactggc | 62.6 | 168 |
| | cccttccattttactttccagagactggc | 60.7 | 169 |
| | ccttccattttactttccagagactggc | 59.2 | 170 |
| | cttccattttactttccagagactggc | 57.6 | 171 |

IL-10 (−819) Primer Set (d)

In connection with the detection of an IL-10 (−819) polymorphism, an example of a primer set is a primer set (d) that contains a forward primer composed of an oligonucleotide (F4) below and a reverse primer composed of an oligonucleotide (R4) below.

(F4) at least one oligonucleotide having a sequence identical to that of a region extending from guanine (g) at base 351 to be considered as the first base to any one of the $24^{th}$ to $39^{th}$ bases in the direction toward the 5' end in the base sequence of SEQ ID NO: 4, with the guanine (g) being the 3' end, and (R4) at least one oligonucleotide complementary to a region extending from guanine (g) at base 420 to be considered as the first base to any one of the $29^{th}$ to $46^{th}$ bases in the direction toward the 3' end in the base sequence of SEQ ID NO: 4, with cytosine (c) complementary to the guanine (g) at base 420 being the 3' end.

Specific examples of forward primers and reverse primers are given below, but the present invention is not limited by the examples. Moreover, combinations of the forward primers and the reverse primers are not at all limited and, among others, a primer set containing a forward primer composed of the base sequence of SEQ ID NO. 182 and a reverse primer composed of the base sequence of SEQ ID NO. 198 is particularly preferable.

TABLE 12

| Primer | Sequence | Tm(° C.) | SEQ ID NO. |
|---|---|---|---|
| IL10(-819) F primers | tcattctatgtgctggagatggtgtacagtagggtgagg | 66.1 | 172 |
| | cattctatgtgctggagatggtgtacagtagggtgagg | 65.6 | 173 |
| | attctatgtgctggagatggtgtacagtagggtgagg | 65.2 | 174 |
| | ttctatgtgctggagatggtgtacagtagggtgagg | 65.3 | 175 |
| | tctatgtgctggagatggtgtacagtagggtgagg | 65.3 | 176 |
| | ctatgtgctggagatggtgtacagtagggtgagg | 64.7 | 177 |
| | tatgtgctggagatggtgtacagtagggtgagg | 64.5 | 178 |
| | atgtgctggagatggtgtacagtagggtgagg | 65 | 179 |
| | tgtgctggagatggtgtacagtagggtgagg | 65.1 | 180 |
| | gtgctggagatggtgtacagtagggtgagg | 64.2 | 181 |
| | tgctggagatggtgtacagtagggtgagg | 63.7 | 182 |
| | gctggagatggtgtacagtagggtgagg | 62.8 | 183 |
| | ctggagatggtgtacagtagggtgagg | 60.8 | 184 |
| | tggagatggtgtacagtagggtgagg | 60.3 | 185 |
| | ggagatggtgtacagtagggtgagg | 59.5 | 186 |
| | gagatggtgtacagtagggtgagg | 57.4 | 187 |

TABLE 12-continued

| Primer | Sequence | Tm(° C.) | SEQ ID NO. |
|---|---|---|---|
| IL10(-819) R primers | aggtagtgctcaccatgacccctaccgtctctattttatagtgagc | 67.9 | 188 |
| | ggtagtgctcaccatgacccctaccgtctctattttatagtgagc | 67.5 | 189 |
| | gtagtgctcaccatgacccctaccgtctctattttatagtgagc | 66.7 | 190 |
| | tagtgctcaccatgacccctaccgtctctattttatagtgagc | 66.5 | 191 |
| | agtgctcaccatgacccctaccgtctctattttatagtgagc | 66.9 | 192 |
| | gtgctcaccatgacccctaccgtctctattttatagtgagc | 66.4 | 193 |
| | tgctcaccatgacccctaccgtctctattttatagtgagc | 66.1 | 194 |
| | gctcaccatgacccctaccgtctctattttatagtgagc | 65.5 | 195 |
| | ctcaccatgacccctaccgtctctattttatagtgagc | 64.2 | 196 |
| | tcaccatgacccctaccgtctctattttatagtgagc | 63.9 | 197 |
| | caccatgacccctaccgtctctattttatagtgagc | 63.4 | 198 |
| | accatgacccctaccgtctctattttatagtgagc | 62.9 | 199 |
| | ccatgacccctaccgtctctattttatagtgagc | 62.1 | 200 |
| | catgacccctaccgtctctattttatagtgagc | 60.9 | 201 |
| | atgacccctaccgtctctattttatagtgagc | 60.3 | 202 |
| | tgacccctaccgtctctattttatagtgagc | 60.2 | 203 |
| | gacccctaccgtctctattttatagtgagc | 59.3 | 204 |
| | acccctaccgtctctattttatagtgagc | 58.8 | 205 |

IL-10 (−1082) Primer Set (e)

In connection with the detection of an IL-10 (−1082) polymorphism, an example of a primer set is a primer set (e) that contains a forward primer composed of an oligonucleotide (F5) below and a reverse primer composed of an oligonucleotide (R5) below.

(F5) at least one oligonucleotide having a sequence identical to that of a region extending from cytosine (c) at base 329 to be considered as the first base to any one of the $22^{nd}$ to $32^{nd}$ bases in the direction toward the 5' end in the base sequence of SEQ ID NO: 5, with the cytosine (c) being the 3' end, and
(R5) at least one oligonucleotide complementary to a region extending from guanine (g) at base 447 to be considered as the first base to any one of the $23^{rd}$ to $39^{th}$ bases in the direction toward the 3' end in the base sequence of SEQ ID NO: 5, with cytosine (c) complementary to the guanine (g) at base 447 being the 3' end.

Specific examples of forward primers and reverse primers are given below, but the present invention is not limited by the examples. Moreover, combinations of the forward primers and the reverse primers are not at all limited and, among others, a primer set containing a forward primer composed of the base sequence of SEQ ID NO. 213 and a reverse primer composed of the base sequence of SEQ ID NO. 227 is particularly preferable.

TABLE 13

| Probe | Sequence | Tm(° C.) | SEQ ID NO. |
|---|---|---|---|
| IL10(-1082) F primers | ctcctcgccgcaacccaactggctctccttac | 69.2 | 206 |
| | tcctcgccgcaacccaactggctctccttac | 69.2 | 207 |
| | cctcgccgcaacccaactggctctccttac | 68.6 | 208 |
| | ctcgccgcaacccaactggctctccttac | 67.4 | 209 |
| | tcgccgcaacccaactggctctccttac | 67.2 | 210 |
| | cgccgcaacccaactggctctccttac | 66.6 | 211 |
| | gccgcaacccaactggctctccttac | 65 | 212 |
| | ccgcaacccaactggctctccttac | 63 | 213 |
| | cgcaacccaactggctctccttac | 61.4 | 214 |
| | gcaacccaactggctctccttac | 59.3 | 215 |
| | caacccaactggctctccttac | 56.7 | 216 |
| IL10(-1082) R primers | aaagaagtcaggattccatggaggctggataggaggtcc | 67.4 | 217 |
| | aagaagtcaggattccatggaggctggataggaggtcc | 67.5 | 218 |
| | agaagtcaggattccatggaggctggataggaggtcc | 67.5 | 219 |
| | gaagtcaggattccatggaggctggataggaggtcc | 67 | 220 |
| | aagtcaggattccatggaggctggataggaggtcc | 66.8 | 221 |
| | agtcaggattccatggaggctggataggaggtcc | 66.9 | 222 |
| | gtcaggattccatggaggctggataggaggtcc | 66.3 | 223 |
| | tcaggattccatggaggctggataggaggtcc | 65.9 | 224 |
| | caggattccatggaggctggataggaggtcc | 65.3 | 225 |
| | aggattccatggaggctggataggaggtcc | 64.8 | 226 |
| | ggattccatggaggctggataggaggtcc | 64.2 | 227 |
| | gattccatggaggctggataggaggtcc | 62.7 | 228 |
| | attccatggaggctggataggaggtcc | 62.3 | 229 |
| | ttccatggaggctggataggaggtcc | 62.3 | 230 |
| | tccatggaggctggataggaggtcc | 62.2 | 231 |
| | ccatggaggctggataggaggtcc | 61.3 | 232 |
| | catggaggctggataggaggtcc | 59.5 | 233 |

IL-10 (−3575) Primer Set (f)

In connection with the detection of an IL-10 (−3575) polymorphism, an example of a primer set is a primer set containing a forward primer composed of an oligonucleotide (F6) below and a reverse primer composed of an oligonucleotide (R6) below.

(F6) at least one oligonucleotide having a sequence identical to that of a region extending from cytosine (c) at base 139 to be considered as the first base to any one of the 25th to 42nd bases in the direction toward the 5' end in the base sequence of SEQ ID NO: 6, with the cytosine (c) being the 3' end, and (R6) at least one oligonucleotide complementary to a region extending from guanine (g) at base 223 to be considered as the first base to any one of the 19th to 33rd bases in the direction toward the 3' end in the base sequence of SEQ ID NO: 6, with cytosine (c) complementary to the guanine (g) at base 223 being the 3' end.

Specific examples of forward primers and reverse primers are given below, but the present invention is not limited by the examples. Moreover, combinations of the forward primers and the reverse primers are not at all limited and, among others, a primer set containing a forward primer composed of the base sequence of SEQ ID NO. 244 and a reverse primer composed of the base sequence of SEQ ID NO. 260 is particularly preferable.

TNF α Primer Set (g)

In connection with the detection of a TNF α polymorphism, an example of a primer set is a primer set containing a forward primer composed of an oligonucleotide (F7) below and a reverse primer composed of an oligonucleotide (R7) below.

(F7) at least one oligonucleotide having a sequence identical to that of a region extending from guanine (g) at base 386 to be considered as the first base to any one of the 26th to 41st bases in the direction toward the 5' end in the base sequence of SEQ ID NO: 7, with the guanine (g) being the 3' end, and (R7) at least one oligonucleotide complementary to a region extending from cytosine (c) at base 418 to be considered as the first base to any one of the 24th to 40th bases in the direction toward the 3' end in the base sequence of SEQ ID NO: 7, with guanine (g) complementary to the cytosine (c) at base 418 being the 3' end.

Specific examples of forward primers and reverse primers are given below, but the present invention is not limited by the examples. Moreover, combinations of the forward primers and the reverse primers are not at all limited and, among others, a primer set containing a forward primer composed of the base sequence of SEQ ID NO. 277 and a reverse primer composed of the base sequence of SEQ ID NO. 293 is particularly preferable.

TABLE 14

| Primer | Sequence | Tm(° C.) | SEQ ID NO. |
|---|---|---|---|
| IL10(−3575) F primers | agaggagcagggatggaagaagagaggtattcccttcccac | 69.8 | 234 |
| | gaggagcagggatggaagaagagaggtattcccttcccac | 69.4 | 235 |
| | aggagcagggatggaagaagagaggtattcccttcccac | 69.3 | 236 |
| | ggagcagggatggaagaagagaggtattcccttcccac | 68.8 | 237 |
| | gagcagggatggaagaagagaggtattcccttcccac | 67.9 | 238 |
| | agcagggatggaagaagagaggtattcccttcccac | 67.8 | 239 |
| | gcagggatggaagaagagaggtattcccttcccac | 67.3 | 240 |
| | cagggatggaagaagagaggtattcccttcccac | 65.9 | 241 |
| | agggatggaagaagagaggtattcccttcccac | 65.5 | 242 |
| | gggatggaagaagagaggtattcccttcccac | 64.9 | 243 |
| | ggatggaagaagagaggtattcccttcccac | 63.7 | 244 |
| | gatggaagaagagaggtattcccttcccac | 62.4 | 245 |
| | atggaagaagagaggtattcccttcccac | 62 | 246 |
| | tggaagaagagaggtattcccttcccac | 62 | 247 |
| | ggaagaagagaggtattcccttcccac | 61 | 248 |
| | gaagaagagaggtattcccttcccac | 59.5 | 249 |
| | aagaagagaggtattcccttcccac | 58.9 | 250 |
| | agaagagaggtattcccttcccac | 58.6 | 251 |
| IL10(−3573) R primers | gcctgagtccagtttgccctcaagcccagatgc | 69.6 | 252 |
| | cctgagtccagtttgccctcaagcccagatgc | 68.2 | 253 |
| | ctgagtccagtttgccctcaagcccagatgc | 67 | 254 |
| | tgagtccagtttgccctcaagcccagatgc | 66.8 | 255 |
| | gagtccagtttgccctcaagcccagatgc | 66 | 256 |
| | agtccagtttgccctcaagcccagatgc | 65.8 | 257 |
| | gtccagtttgccctcaagcccagatgc | 65.1 | 258 |
| | tccagtttgccctcaagcccagatgc | 64.5 | 259 |
| | ccagtttgccctcaagcccagatgc | 63.8 | 260 |
| | cagtttgccctcaagcccagatgc | 62.1 | 261 |
| | agtttgccctcaagcccagatgc | 61.4 | 262 |
| | gtttgccctcaagcccagatgc | 60.4 | 263 |
| | tttgccctcaagcccagatgc | 59.5 | 264 |
| | ttgccctcaagcccagatgc | 59.2 | 265 |
| | tgccctcaagcccagatgc | 58.8 | 266 |

TABLE 15

| Primer | Sequence | Tm(° C.) | SEQ ID NO. |
|---|---|---|---|
| TNFα(-308) F primers | agaccacagacctggtccccaaaagaaatggaggcaatagg | 68.9 | 267 |
| | gaccacagacctggtccccaaaagaaatggaggcaatagg | 68.5 | 268 |
| | accacagacctggtccccaaaagaaatggaggcaatagg | 68.4 | 269 |
| | ccacagacctggtccccaaaagaaatggaggcaatagg | 67.8 | 270 |
| | cacagacctggtccccaaaagaaatggaggcaatagg | 66.8 | 271 |
| | acagacctggtccccaaaagaaatggaggcaatagg | 66.5 | 272 |
| | cagacctggtccccaaaagaaatggaggcaatagg | 65.8 | 273 |
| | agacctggtccccaaaagaaatggaggcaatagg | 65.4 | 274 |
| | gacctggtccccaaaagaaatggaggcaatagg | 64.8 | 275 |
| | acctggtccccaaaagaaatggaggcaatagg | 64.6 | 276 |
| | cctggtccccaaaagaaatggaggcaatagg | 63.7 | 277 |
| | ctggtccccaaaagaaatggaggcaatagg | 62.4 | 278 |
| | tggtccccaaaagaaatggaggcaatagg | 62 | 279 |
| | ggtccccaaaagaaatggaggcaatagg | 61 | 280 |
| | gtccccaaaagaaatggaggcaatagg | 59.5 | 281 |
| | tccccaaaagaaatggaggcaatagg | 58.6 | 282 |
| TNFα(-308) R primers | gtcttctgggccactgactgatttgtgtgtaggaccctgg | 69.3 | 283 |
| | tcttctgggccactgactgatttgtgtgtaggaccctgg | 69.1 | 284 |
| | cttctgggccactgactgatttgtgtgtaggaccctgg | 68.7 | 285 |
| | ttctgggccactgactgatttgtgtgtaggaccctgg | 68.6 | 286 |
| | tctgggccactgactgatttgtgtgtaggaccctgg | 68.7 | 287 |
| | ctgggccactgactgatttgtgtgtaggaccctgg | 68.2 | 288 |
| | tgggccactgactgatttgtgtgtaggaccctgg | 68 | 289 |
| | gggccactgactgatttgtgtgtaggaccctgg | 67.4 | 290 |
| | ggccactgactgatttgtgtgtaggaccctgg | 66.2 | 291 |
| | gccactgactgatttgtgtgtaggaccctgg | 65 | 292 |
| | ccactgactgatttgtgtgtaggaccctgg | 63.3 | 293 |
| | cactgactgatttgtgtgtaggaccctgg | 62 | 294 |
| | actgactgatttgtgtgtaggaccctgg | 61.3 | 295 |
| | ctgactgatttgtgtgtaggaccctgg | 60.3 | 296 |
| | tgactgatttgtgtgtaggaccctgg | 59.8 | 297 |
| | gactgatttgtgtgtaggaccctgg | 58.6 | 298 |
| | actgatttgtgtgtaggaccctgg | 57.9 | 299 |

TNF β Primer Set (h)

In connection with the detection of a TNF β polymorphism, an example of a primer set is a primer set containing a forward primer composed of an oligonucleotide (F8) below and a reverse primer composed of an oligonucleotide (R8) below.
(F8) at least one oligonucleotide having a sequence identical to that of a region extending from cytosine (c) at base 350 to be considered as the first base to any one of the $18^{th}$ to $37^{th}$ bases in the direction toward the 5' end in the base sequence of SEQ ID NO: 300, with the cytosine (c) being the 3' end, and
(R8) at least one oligonucleotide complementary to a region extending from guanine (g) at base 443 to be considered as the first base to any one of the $17^{th}$ to $37^{th}$ bases in the direction toward the 3' end in the base sequence of SEQ ID NO: 300, with cytosine (c) complementary to the guanine (g) at base 443 being the 3' end.

Specific examples of forward primers and reverse primers are shown below, but the present invention is not limited by the examples. Moreover, combinations of the forward primers and the reverse primers are not at all limited and, among others, a primer set containing a forward primer composed of the base sequence of SEQ ID NO. 337 and a reverse primer composed of the base sequence of SEQ ID NO. 312 is particularly preferable.

TABLE 16

| Primer | Sequence | Tm(° C.) | SEQ ID NO. |
|---|---|---|---|
| TNFB(+252) F primers | cgacagagaaggggacaagatgcagtcagagaaaccc | 67.6 | 330 |
| | gacagagaaggggacaagatgcagtcagagaaaccc | 66.4 | 331 |
| | acagagaaggggacaagatgcagtcagagaaaccc | 66.3 | 332 |
| | cagagaaggggacaagatgcagtcagagaaaccc | 65.5 | 333 |
| | agagaaggggacaagatgcagtcagagaaaccc | 65.1 | 334 |
| | gagaaggggacaagatgcagtcagagaaaccc | 64.5 | 335 |
| | agaaggggacaagatgcagtcagagaaaccc | 64.2 | 336 |
| | gaaggggacaagatgcagtcagagaaaccc | 63.6 | 337 |
| | aaggggacaagatgcagtcagagaaaccc | 63.2 | 338 |
| | aggggacaagatgcagtcagagaaaccc | 63.1 | 339 |
| | ggggacaagatgcagtcagagaaaccc | 62.4 | 340 |
| | gggacaagatgcagtcagagaaaccc | 60.8 | 341 |
| | ggacaagatgcagtcagagaaaccc | 59.1 | 342 |
| | gacaagatgcagtcagagaaaccc | 57.3 | 343 |
| | acaagatgcagtcagagaaaccc | 56.6 | 344 |
| | caagatgcagtcagagaaaccc | 55.2 | 345 |
| | aagatgcagtcagagaaaccc | 53.9 | 346 |
| | agatgcagtcagagaaaccc | 53.3 | 347 |
| | gatgcagtcagagaaaccc | 51.9 | 348 |
| | atgcagtcagagaaaccc | 50.5 | 349 |

TABLE 16-continued

| Primer | Sequence | Tm (° C.) | SEQ ID NO. |
|---|---|---|---|
| RNFB(+252) | tttggtttccttctctgtctctgactctccatctgtc | 64.2 | 309 |
| R primers | ttggtttccttctctgtctctgactctccatctgtc | 64.2 | 310 |
| | tggtttccttctctgtctctgactctccatctgtc | 64.1 | 311 |
| | ggtttccttctctgtctctgactctccatctgtc | 63.4 | 312 |
| | gtttccttctctgtctctgactctccatctgtc | 62.2 | 313 |
| | tttccttctctgtctctgactctccatctgtc | 61.6 | 314 |
| | ttccttctctgtctctgactctccatctgtc | 61.5 | 315 |
| | tccttctctgtctctgactctccatctgtc | 61.3 | 316 |
| | ccttctctgtctctgactctccatctgtc | 60.6 | 317 |
| | cttctctgtctctgactctccatctgtc | 59.1 | 318 |
| | ttctctgtctctgactctccatctgtc | 58.5 | 319 |
| | tctctgtctctgactctccatctgtc | 58.2 | 320 |
| | ctctgtctctgactctccatctgtc | 57.3 | 321 |
| | tctgtctctgactctccatctgtc | 56.5 | 322 |
| | ctgtctctgactctccatctgtc | 55.4 | 323 |
| | tgtctctgactctccatctgtc | 54.5 | 324 |
| | gtctctgactctccatctgtc | 53 | 325 |
| | tctctgactctccatctgtc | 51.5 | 326 |
| | ctctgactctccatctgtc | 50 | 327 |
| | tctgactctccatctgtc | 48.5 | 328 |
| | ctgactctccatctgtc | 46.7 | 329 |

In the step (1), the proportion (molar ratio) of the probe of the present invention relative to the sample nucleic acid is not particularly limited, but since a detection signal can be obtained sufficiently, it is preferably equimolar or less, and more preferably 0.1 or less. Here, the sample nucleic acid may refer to, for example, the total of a perfect-match nucleic acid that has a perfect-match sequence and a mismatch nucleic acid that has a mismatch sequence or may refer to the total of an amplification product that contains a perfect-match sequence and an amplification product that contains a mismatch sequence. The proportion of perfect-match DNA in a sample nucleic acid is usually unknown, and it is preferable at the end that the proportion (molar ratio) of probe is 10 or less relative to a perfect-match nucleic acid (amplification product containing a perfect-match sequence), more preferably 5 or less, and even more preferably 3 or less. Moreover, the lower limit thereof is not particularly limited and, for example, it is 0.001 or greater, preferably 0.01 or greater, and more preferably 0.1 or greater. The proportion of the probe of the present invention relative to the sample nucleic acid may refer to, for example, a molar ratio relative to a double-strand nucleic acid or may refer to a molar ratio relative to a single strand nucleic acid.

Samples to which the polymorphism detection method of the present invention is applied are not particularly limited, and examples include biological samples. Specific examples of such biological samples include blood cells such as leukocyte cells, whole blood, buccal cells such as oral mucosa, somatic cells such as nail and hair, reproductive cells, sputa, amniotic fluids, paraffin-embedded tissues, urine, gastric fluids, gastric lavage fluids, etc. In the present invention, the method for collecting the sample, the method for preparing a sample nucleic acid from the sample and like methods are not limited, and a known method can be used.

A description is given of a Tm value here. As a solution containing a double-strand nucleic acid (for example, double-strand DNA) is heated, the absorbance at 260 nm is increased. This is because the hydrogen bonding between the strands in the double-strand nucleic acid is broken by heating, resulting in dissociation into a single-strand nucleic acid (for example, a single-strand DNA) (melting of DNA). When the entire double-strand nucleic acid is dissociated into a single-strand nucleic acid, the absorbance thereof is about 1.5 times greater than the absorbance at the beginning of heating (the absorbance of a double-strand nucleic acid only), and the completion of melting can be determined accordingly. Based on this phenomenon, a melting temperature Tm generally is defined as a temperature at which absorbance shows a 50% increase relative to the initial absorbance.

In the present invention, the measurement of a change in signal that is associated with a temperature change for determining a Tm value can be performed by measuring the absorbance at 260 nm according to the principle described above, and it is preferable to measure the signal of a labeling material added to a probe. Therefore, it is preferable to use the above-described labeled probes as the probes of the present invention. Examples of the labeled probes include a labeled probe that gives a signal when alone and that does not give any signal when forming a hybrid and a labeled probe that does not give any signal when alone and that gives a signal when forming a hybrid. The former probe does not give any signal when forming a hybrid (double-strand nucleic acid) with a detection target sequence and gives a signal when the probe is liberated by heating. Moreover, the latter probe gives a signal when forming a hybrid (double-strand nucleic acid) with a detection target sequence and the signal is reduced (quenched) when the probe is liberated by heating. Therefore, by detecting the signal of such a labeling material under conditions that are specific to the signal (absorbance and the like), the advancement of melting and a Tm value can be determined in the same manner as in the measurement of the absorption at 260 nm. Examples of labeling materials for use in labeled probes are as described above.

Next, the polymorphism detection method of the present invention will be described in reference to an example in which a nucleic acid amplification product is used as a sample nucleic acid and a labeled probe that is labeled with a fluorescent dye is used as a probe of the present invention. A feature of the polymorphism detection method of the present invention is the use of a probe of the present invention per se, and the method is not at all limited by other aspects such as processes or conditions.

First, genomic DNA is isolated from whole blood. Isolation of genomic DNA from whole blood can be performed according to a known method. For a specific example, a commercially available genomic DNA isolation kit (trade name: GFX genomic blood DNA purification kit, manufactured by GE Healthcare Bioscience) or the like can be used.

Next, a labeled probe is added to a sample containing the isolated genomic DNA to prepare a reaction mixture. As described above, one type of labeled probe may be added, or two or more types of labeled probe may be added. For example, a QProbe is preferable as the labeled probe. A QProbe is generally a probe in which the cytosine at a probe end is labeled with a fluorescent dye, and due to the hybridization between this probe and a detection target sequence, the fluorescent dye and the guanine of the detection target sequence interact, resulting in a reduction in (or quenching of) fluorescence. The base sequence of the labeled probe is as described above, and it can be suitably selected according to the polymorphism to be detected.

The time to add the labeled probe is not particularly limited and, for example, addition to a PCR amplification product may be performed after a nucleic acid amplification reaction that will be described below, or addition may be performed before a nucleic acid amplification reaction. When the labeled probe is added before a nucleic acid amplification reaction such as PCR as described above, it is preferable, for example, to add a fluorescent dye or a phosphate group to the 3' end of the probe as described above.

The labeled probe may be added to a sample containing isolated genomic DNA or may be mixed with genomic DNA in a solvent. The solvent is not particularly limited and examples include buffers such as Tris-HCl; solvents containing KCl, $MgCl_2$, $MgSO_4$, glycerol and the like; reaction fluids for nucleic acid amplification such as reaction fluids for PCR; and those that are conventionally known.

Then, using the isolated genomic DNA as a template, a sequence that contains a detection target site where a polymorphism to be detected is generated is amplified according to a nucleic acid amplification method such as PCR in the presence of the labeled probe. Below, the present invention will be described using an example in which PCR is used as a nucleic acid amplification method, but the present invention is not limited thereto. Moreover, PCR conditions are not particularly limited and PCR can be carried out in a conventional manner.

In particular, PCR is carried out on a reaction mixture as described above that contains the genomic DNA and the labeled probe. The composition of the reaction mixture is not particularly limited and can be suitably arranged by a person skilled in the art and, for example, polymerases such as DNA polymerases, dNTPs such as dATP, dTTP, dCTP, dGTP and dUTP, buffers, various catalysts, primers, etc., may be contained therein in addition to the genomic DNA and the labeled probe.

Next, the dissociation of the amplification product (double-strand DNA) thus obtained as well as the hybridization between the single-strand DNA obtained by the dissociation and the labeled probe are performed. These can be carried out by, for example, changing the temperature of the reaction fluid.

The dissociation of the double-strand DNA can be carried out, for example, by heating. The heating temperature in this dissociation step is not particularly limited insofar as the amplification product can be dissociated and is, for example, 85 to 95° C. The heating time also is not particularly limited, and it is usually 1 second to 10 minutes and preferably 1 second to 5 minutes.

The hybridization between the dissociated single-strand DNA and the labeled probe can be carried out by, for example, lowering the heating temperature applied in the dissociation step after the dissociation step. Temperature conditions in this hybridization step are not particularly limited, and it is preferable that the temperature is lower than the Tm value of the labeled probe, for example, 40 to 50° C. Moreover, the duration of the treatment at such a temperature is not particularly limited and it is, for example, 1 to 600 seconds.

In the hybridization step, the volume and the concentration of each component of the reaction fluid are not particularly limited. For specific examples, the concentration of DNA in the reaction fluid is, for example, 0.01 to 1 μmol/L and preferably 0.1 to 0.5 μmol/L, and the concentration of the labeled probe is, for example, preferably within a range that satisfies the aforementioned proportion relative to the DNA, e.g., 0.001 to 10 μmol/L and preferably 0.001 to 1 μmol/L.

Then, the temperature of the reaction fluid is changed and a signal value that indicates the melting state of the hybridization product between the amplification product (the single-strand DNA) and the labeled probe is measured. In particular, the product of hybridization between the single-strand DNA and the labeled probe is heated by, for example, heating the reaction fluid, and a change in signal value associated with a temperature increase is measured. For example, when a probe in which the end cytosine is labeled (guanine-quenching probe) is used as described above, fluorescence is reduced (or quenched) if the probe is in a hybridized state with the single-strand DNA, and fluorescence is emitted if the probe is in a dissociated state. Therefore, for example, a hybridization product with reduced (or quenched) fluorescence is heated gradually, and an increase in the intensity of fluorescence associated with the temperature increase is measured.

The temperature range when measuring a change in the intensity of fluorescence is not particularly limited and, for example, the starting temperature is room temperature to 85° C. and preferably 25 to 70° C., and the end temperature is, for example, 40 to 105° C. The rate of temperature increase is not particularly limited and, for example, it is 0.1 to 20° C./second and preferably 0.3 to 5° C./second.

When two or more types of polymorphism are to be detected using two or more types of labeled probe, a change in signal resulting from each labeled probe is measured under conditions selected according to the labeling material of each labeled probe.

Next, the change in signal is analyzed to determine a Tm value. In particular, the extent of change in fluorescence intensity per unit time at respective temperatures, for example, is calculated based on the intensity of fluorescence thus obtained. For example, when the extent of change is (−d extent of increase in fluorescence intensity/dt), the temperature at which the lowest value is indicated can be determined as a Tm value. In addition, when the extent of change is (d extent of increase in fluorescence intensity/dt) for example, the highest point can be determined as a Tm value. When a probe that does not give any signal when alone and that gives a signal when forming a hybrid is used as a labeled probe instead of a quenching probe, the extent of decrease in fluorescence intensity is measured instead.

Then, the polymorphism (genotype) in the desired detection target site is determined based on the Tm values. The results obtained from the Tm analysis show that, for example, a hybrid (match) that is fully complementary exhibits a Tm value, which indicates dissociation, higher than that of a hybrid (mismatch) that has one different nucleotide. Therefore, by determining in advance the Tm value of a hybrid that is fully complementary and the Tm value of a hybrid that has one different nucleotide in connection with a probe, the polymorphism in the desired detection target site can be determined. For example, when the polymorphism in the desired detection target site is X or Y and when a probe that is fully complementary to a detection target sequence whose detection target site is X is used, the base of the detection target site can be judged as X if the Tm value of a hybrid thus formed is the same as the Tm value of a fully complementary hybrid. On the other hand, if the Tm value of the hybrid thus formed is the same as the Tm value of a hybrid having one different nucleotide or is lower than the Tm value of a fully complementary hybrid, the base of the detection target site can be judged as Y.

Moreover, in the present invention, instead of the method described above in which the temperature of a reaction fluid is increased to heat a hybridization product and a change in signal associated with the temperature increase is measured, for example, a change in signal upon hybrid formation may be measured. That is, when a hybridization product is formed by lowering the temperature of a reaction fluid containing a probe, a change in signal associated with the temperature decrease may be measured.

The case where a labeled probe that gives a signal when alone and that does not give any signal when forming a hybrid (for example, a QProbe) is used will be described as a specific example. Fluorescence is emitted when single-strand DNA and the probe are in a dissociated state, and this fluorescence is reduced (or quenched) when a hybrid is formed due to a temperature decrease. Therefore, for example, the temperature of the reaction fluid may be gradually lowered, and the reduction in fluorescence intensity associated with the temperature decrease may be measured. On the other hand, when a labeled probe that does not give any signal when alone and that gives a signal when forming a hybrid is used, no fluorescence is emitted when single-strand DNA and the probe are in a dissociated state, and when a hybrid is formed due to a temperature decrease, fluorescence is emitted. Therefore, the temperature of the reaction fluid gradually may be lowered for example, and an increase in fluorescence intensity associated with the temperature decrease may be measured.

Polymorphism Detection Reagent

The polymorphism detection reagent of the present invention is a polymorphism detection reagent for detecting an immune-related gene polymorphism and contains a polymorphism detection probe of the present invention. A feature of the present invention is to contain an aforementioned polymorphism detection probe of the present invention, and any other configurations and conditions are not limited at all. The polymorphism detection reagent of the present invention also can be called as a probe kit for use, for example, in the detection of an immune-related gene polymorphism.

In the polymorphism detection reagent of the present invention, one type or two or more types of the polymorphism detection probe of the present invention may be present. When there are two or more types of the probe, a combination thereof is not particularly limited and examples of such a combination are as described above. Two or more types of the probe may be accommodated in, for example, separate containers, or may be accommodated in the same container in a mixed state since the detection of polymorphisms is possible in a single reaction system as described above. Moreover, when two or more types of probes are contained, it is preferable that each probe is labeled with a different labeling material. Accordingly, the use of different types of labeling materials enables respective probes to be detected even in a single reaction system. It is preferable that the labeling materials are, for example, materials of different detection wavelengths.

As described above, immune-related genes such as the FCGR3A gene, the FCGR2A gene, the IL-10 gene, the TNF α gene and the TNF β gene are each reported to have polymorphisms that are involved in the pharmaceutical effects of antibody drugs such as malignant lymphoma drugs (for example, trade name: rituxan) and breast cancer drugs (for example, trade name: herceptin), and such polymorphisms can all be detected with the use of the probes of the present invention. In connection with such polymorphisms, there may be a case where variants are detected in, for example, only one type and there may be a case where variants are detected in two or more types. Although the detection target polymorphisms in the present invention each show an association with the pharmaceutical effects of the aforementioned antibody drugs, they are believed to show their own respective specific characteristics. Thus, for example, the detection of a plurality of polymorphisms and a comprehensive evaluation of the results thereof will enable better diagnosis and medical treatment. Therefore, if two or more types of the probe of the present invention are contained in the polymorphism detection reagent or probe kit of the present invention, polymorphism detection that is intended for diagnosis, medical treatment and the like can be carried out in a simpler manner.

The detection reagent of the present invention further may contain a primer or a primer set for amplifying a region that includes a site to be detected in an immune-related gene. Examples of primer sets include those described above depending on the type of the probe of the present invention to be used. In particular, it is preferable to contain in any combination an FCGR3A probe and an FCGR3A primer set; an FCGR2A probe and an FCGR2A primer set; an IL-10 (−592) probe and an IL-10 (−592) primer set; an IL-10 (−819) probe and an IL-10 (−819) primer set; an IL-10 (−1082) probe and an IL-10 (−1082) primer set; an IL-10 (−3575) probe and an IL-10 (−3575) primer set; a TNF α probe and a TNF α primer set; and a TNF β probe and a TNF β primer set.

Combinations of the probes of the present invention are not particularly limited, and examples include those described above. Also, a combination of primers or primer sets can be determined according to the combination of the probes of the present invention.

The detection reagent of the present invention may contain, for example, components necessary for a nucleic acid amplification reaction in addition to those described above. Specific examples include polymerases such as DNA polymerases, dNTPs such as dATP, dTTP, dCTP, dGTP and dUTP, buffers, various catalysts, etc. Furthermore, the detection reagent of the present invention may be a detection reagent kit and may include instructions for use.

Next, the examples of the present invention shall be described. The present invention, however, is not limited by the following examples. The unit "%" refers to "w/v %".

EXAMPLES

Example 1

Detection of FCGR3A Polymorphism and IL-10 (−819) Polymorphism

Using probes of the present invention, FCGR3A polymorphisms and IL-10 (−819) polymorphisms were detected by a Tm analysis.

Blood was collected using EDTA blood collection tubes from 3 healthy subjects whose FCGR3A polymorphism and IL-10 (−819) polymorphism were known (Sample 1 to Sample 3). The FCGR3A polymorphism and the IL-10 (−819) polymorphism of each sample were as follows.

|  | FCGR3A Polymorphisms | IL-10 (−819) Polymorphisms |
|---|---|---|
| Sample 1 | T/T | C/C |
| Sample 2 | G/T | T/C |
| Sample 3 | T/T | T/T |

Each sample (10 µL) was mixed with 70 µL of the following test sample dilution 1, and the mixtures (10 µL each) were further mixed with 70 µL of the following test sample dilution 2. Each mixture (17 µL) was heated at 95° C. for 10 minutes and introduced into 46 µL of the following PCR reaction solution to carry out PCR. The PCR included a treatment at 95° C. for 60 seconds and then repeating 50 times a cycle of heating at 95° C. for 1 second and 62° C. for 15 seconds, followed by a treatment at 95° C. for 1 second and 40° C. for 60 seconds all performed by a thermal cycler. Then, the PCR reaction solution was heated from 40° C. to 75° C. at a rate of temperature increase of 1° C./3 seconds, and change in fluorescence intensity over time was measured (wavelengths: 515 to 555 nm, 585 to 700 nm).

Test Sample Dilution 1

| 10 mmol/L | Tris-HCl |
|---|---|
| 0.1 mmol/L | EDTA |
| 0.05% | NaN₃ |
| 0.3% | SDS |

Test Sample Dilution 2

| 10 mmol/L | Tris-HCl |
|---|---|
| 0.1 mmol/L | EDTA |
| 0.05% | NaN₃ |

TABLE 17

| (PCR reaction solution) | (Unit: µL) |
|---|---|
| Distilled water | 28.02 |
| 10% NaN₃ | 0.23 |
| 20% BSA | 0.5 |
| 50% Glycerol | 2.5 |
| 10 × Gene Taq buffer* | 5 |
| 2.5 mmol/L dNTPs | 4 |
| 5 µmol/L FCGR3A probe | 2 |
| 100 µmol/L FCGR3A F primer | 0.5 |
| 100 µmol/L FCGR3A R primer | 0.25 |
| 5 µmol/L IL-10 (−819) probe | 2 |
| 100 µmol/L IL-10 (−819) F primer | 0.5 |
| 100 µmol/L IL-10 (−819) R primer | 0.25 |
| 5 U/µL Gene Taq FP* | 0.25 |
| Total | 46    µL |

*Trade name: Gene Taq FP, manufactured by Nippon Gene Co., Ltd.
FCGR3A probe (SEQ ID NO. 14)
5'-tcccaaAaagccccc-(BODIPY FL)-3'
FCGR3A F primer (SEQ ID NO. 77)
5'-tctgacttctacattccaaaagccacactcaaagac-3'
FCGR3A R primer (SEQ ID NO. 97)
5'-ctcctcccaactcaacttcccagtgtgat-3'
IL-10 (−819) probe (SEQ ID NO. 36)
5'-acagagatGttacatcacc-(TAMRA)-3'
IL-10 (−819) F primer (SEQ ID NO. 182)
5'-tgctggagatggtgtacagtagggtgagg-3'
IL-10 (−819) R primer (SEQ ID NO. 198)
5'-caccatgacccctaccgtctctattttatagtgagc-3'

FIG. 1 shows the results. FIG. 1 depicts graphs of a Tm analysis that shows the change in fluorescence intensity associated with temperature increase. In FIG. 1, "(A)" shows the results of Sample 1, "(B)" shows the results of Sample 2 and "(C)" shows the results of Sample 3, and the upper row shows the results for the FCGR3A polymorphisms and the bottom row shows the results for the IL-10 (−819) polymorphisms.

In this example, a probe that perfectly matched the FCGR3A polymorphism (t) of the sense strand was used as an FCGR3A probe, and a probe that perfectly matched the IL-10 (−819) polymorphism (c) of the sense strand was used as an IL-10 (−819) probe. As a result, in the detection of an FCGR3A polymorphism, Sample 1 and Sample 3, which contain homozygotes (T/T), showed a peak only at 57.0° C., indicating a perfect match as shown in the upper row of FIG. 1. On the other hand, Sample 2, which contains a heterozygote (G/T), showed a peak at 57.0° C., indicating a perfect match, as well as a peak at 48.0° C., indicating a single-base mismatch. Moreover, in the detection of an IL-10 (−819) polymorphism, Sample 1, which contains a homozygote (C/C), showed a peak only at 59.0° C., indicating a perfect match, and Sample 3, which contains a homozygote (T/T), showed a peak only at 52.5° C., indicating a mismatch, as shown in the bottom row of FIG. 1. On the other hand, Sample 2, which contains a heterozygote (T/C), showed a peak at 59.0° C., indicating a perfect match, and a peak at 52.5° C., indicating a single-base mismatch. As can be understood from these results, using probes of the present invention, whether hybridization with a detection target sequence is of a perfect match or a mismatch can be determined sufficiently, and two types of polymorphisms can be determined using a single reaction system.

Example 2

Detection of FCGR2A Polymorphism, IL-10 (−592) Polymorphism and TNF α Polymorphism Using probes of the present invention, an FCGR2A polymorphism, an IL-10 (−592) polymorphism and TNF α (−308) polymorphisms were detected by a Tm analysis.

Blood was collected using an EDTA blood collection tube from a healthy subject whose FCGR2A polymorphism, IL-10 (−592) polymorphism and TNF α (−308) polymorphism were known (Sample 1). A plasmid having a TNF α gene whose TNF α (−308) polymorphism was a homozygote (A/A) was prepared (Sample 2). The FCGR2A polymorphism, the IL-10 (−592) polymorphism and the TNF α (−308) polymorphism of each sample were as follows.

|  | FCGR2A Polymorphism | IL-10 (−592) Polymorphism | TNFa Polymorphism |
|---|---|---|---|
| Sample 1 | C/T | C/A | G/G |
| Sample 2 | — | — | A/A |

Sample 1 (10 μL) was mixed with 70 μL of the test sample dilution 1 described above, and the mixture (10 μL) was further mixed with 70 μL of the test sample dilution 2 described above. This mixture (17 μL) was heated at 95° C. for 10 minutes and introduced into 46 μL of the following PCR reaction solution to carry out PCR. On the other hand, 1 μL of Sample 2 (3.5 pg) was introduced into 46 μL of the following PCR reaction solution to carry out PCR. The PCR included a treatment at 95° C. for 60 seconds and then repeating 50 times a cycle of heating at 95° C. for 1 second and 62° C. for 15 seconds, followed by a treatment at 95° C. for 1 second and 40° C. for 60 seconds all performed by a thermal cycler. Then, the PCR reaction solution was heated from 40° C. to 75° C. at a rate of temperature increase of 1° C./3 seconds, and change in fluorescence intensity over time was measured (wavelengths: 450 to 480 nm, 515 to 555 nm, 585 to 700 nm).

TABLE 18

| (PCR reaction solution) | (Unit: μL) |
|---|---|
| Distilled water | 17.77 |
| 10% NaN$_3$ | 0.23 |
| 20% BSA | 0.5 |
| 50% Glycerol | 10 |
| 10 × Gene Taq buffer* | 5 |
| 2.5 mmol/L dNTPs | 4 |
| 5 μmol/L IL-b (−592) probe | 2 |
| 100 μmol/L IL-10 (−592) F primer | 0.5 |
| 100 μmol/L IL-10 (−592) R primer | 0.25 |
| 5 μmol/L FCGR2A probe | 2 |
| 100 μmol/L FCGR2A F primer | 0.25 |

TABLE 18-continued

| (PCR reaction solution) | (Unit: μL) |
|---|---|
| 100 μmol/L FCGR2A R primer | 0.5 |
| 5 μmol/L TNF α (−308) probe | 2 |
| 100 μmol/L TNF α (−308) F primer | 0.5 |
| 100 μmol/L TNF α (−308) R primer | 0.25 |
| 5 U/μL Gene Taq FP* | 0.25 |
| Total | 46 μL |

Trade name: Gene Taq FP, manufactured by Nippon Gene Co., Ltd.
IL-10 (−592) probe (SEQ iD NO. 30)
5'-(Pacific Blue) -cttcctacagTacaggcg-P-3'
IL-10(−592) F primer (SEQ ID NO. 148)
5'-ggtaaaggagcctggaacacatcctgtgac-3'
IL-10(−592) Rprimer (SEQ ID NO. 167)
5'- agcccttccattttactttccagagactggc-3'
FCGR2A probe (SEQ ID NO. 23)
5'-ttctcccAtttggatccc-(BODIPY FL)-3'
FCGR2A F primer (SEQ ID NO. 132)
5'-ctgtggtttgcttgtgggatggagaagg-3'
FCGR2A R primer (SEQ ID NO. 38)
5'-aggtcacattcttccagaatggaaaatcccagaaattc-3'
TNF α (−308) probe (SEQ ID NO. 64)
5'-ccgtccCcatgccc-(TAMRA)-3'
TNF α (−308) F primer (SEQ ID NO. 277)
5'-cctggtccccaaaagaaatggaggcaatagg-3'
TNF α (−308) R primer (SEQ ID NO. 293)
5'-ccactgactgatttgtgtgtaggaccctgg-3'

Figure 2:
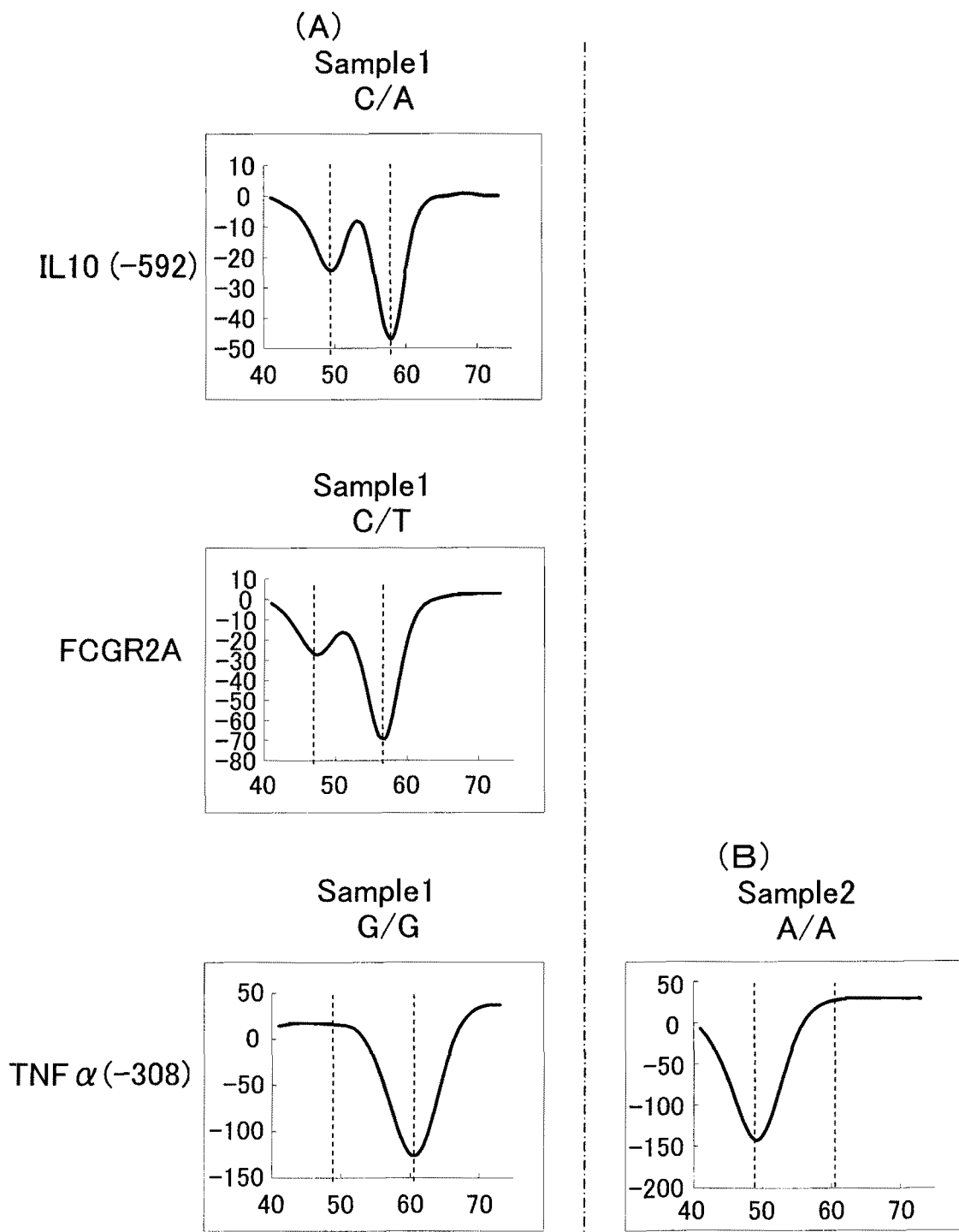
FIG. 2 depicts graphs showing the results of a Tm analysis in Example 2 of the present invention.

FIG. 2 shows the results. FIG. 2 depicts graphs of a Tm analysis that shows the change in fluorescence intensity associated with the temperature increase. In FIG. 2, "(A)" shows the results of Sample 1, "(B)" shows the results of Sample 2, the upper row shows the results for the IL-10 (−592) polymorphism, the mid row shows the results for the FCGR2A polymorphism, and the bottom row shows the results for the TNF α (−308) polymorphisms.

In this example, a probe that perfectly matched the IL-10 (−592) polymorphism (a) of the sense strand was used as an IL-10 (−592) probe, a probe that perfectly matched the FCGR2A polymorphism (t) of the sense strand was used as an FCGR2A probe, and a probe that perfectly matched the TNF α (−308) polymorphism (g) of the sense strand was used as a TNF α (−308) probe. As a result, in the detection of an IL-10 (−592) polymorphism, Sample 1, which contains a heterozygote (C/A), showed a peak at 58.0° C., indicating a perfect match, as well as a peak at 50.0° C., indicating a single-base mismatch, as shown in the upper row of FIG. 2. Moreover, in the detection of an FCGR2A polymorphism, Sample 1, which contains a heterozygote (C/T), showed a peak at 57.0° C., indicating a perfect match, as well as a peak at 48.0° C., indicating a single-base mismatch, as shown in the mid row of FIG. 2. Furthermore, in the detection of an TNF α (−308) polymorphism, Sample 1, which contains a homozygote (G/G), showed a peak only at 61.0° C., indicating a perfect match, and Sample 2, which contains a homozygote (A/A), showed a peak only at 49.0° C., indicating a single-base mismatch, as shown in the bottom row of FIG. 2. As can be understood from the results, using probes of the present invention, whether hybridization with a detection target sequence is of a perfect match or mismatch can be determined sufficiently, and three types of polymorphisms can be determined using a single reaction system.

Example 3

Detection of IL-10 (−1082) Polymorphism and IL-10 (−3575) Polymorphism

Using probes of the present invention, IL-10 (−1082) polymorphisms and IL-10 (−3575) polymorphisms were detected by a Tm analysis.

Blood was collected using an EDTA blood collection tube from a healthy subject whose IL-10 (−1082) polymorphism and IL-10 (−3575) polymorphism were known (Sample 1). Moreover, using a GFX Genomic Blood DNA Purification Kit (trade name, manufactured by GE Healthcare Bioscience), a genome whose IL-10 (−1082) polymorphism and IL-10 (−3575) polymorphism were known was purified, and diluted 10 fold to give Sample 2. In addition, a synthetic DNA whose IL-10 (−3575) polymorphism was a homozygote (A/A) was prepared (Sample 3). The IL-10 (−1082) polymorphism and the IL-10 (−3575) polymorphism of each sample were as follows.

|  | IL-10 (−1082) Polymorphism | IL-10 (−3575) Polymorphism |
| --- | --- | --- |
| Sample 1 | A/A | T/T |
| Sample 2 | A/G | T/T |
| Sample 3 | — | A/A |

Sample 1 (10 µL) was mixed with 70 µL of the test sample dilution 1 described above, and the mixture (10 µL) was further mixed with 70 µL of the test sample dilution 2 described above. This mixture (17 µL) was heated at 95° C. for 10 minutes and introduced into 46 µL of the following PCR reaction solution to carry out PCR. On the other hand, 1 µL of Sample 2 and 1 µL of Sample 3 (3.5 pg) each were introduced into 46 µL of the following PCR reaction solution to carry out PCR. The PCR included a treatment at 95° C. for 60 seconds and then repeating 50 times a cycle of heating at 95° C. for 1 second and 64° C. for 15 seconds, followed by a treatment at 95° C. for 1 second and 40° C. for 60 seconds all performed by a thermal cycler. Then, the PCR reaction solution was heated from 40° C. to 75° C. at a rate of temperature increase of 1° C./3 seconds, and change in fluorescence intensity over time was measured (wavelengths: 515 to 555 nm, 585 to 700 nm).

TABLE 19

| (PCR reaction solution) | (Unit: µL) |
| --- | --- |
| Distilled water | 20.27 |
| 10% NaN$_3$ | 0.23 |
| 20% BSA | 0.5 |
| 50% Glycerol | 10 |
| 10 × Gene Taq buffer* | 5 |
| 2.5 mmol/L dNTPs | 4 |
| 100 mmol/L MgCl$_2$ | 0.25 |
| 5 µmol/L IL-10 (−1082) probe | 2 |
| 100 µmol/L IL-10 (−1082) F primer | 0.5 |
| 100 µmol/L IL-10 (−1082) R primer | 0.25 |
| 5 µmol/L IL-10 (−3575) probe | 2 |

TABLE 19-continued

| (PCR reaction solution) | (Unit: µL) |
| --- | --- |
| 100 µmol/L IL-10 (−3575) F primer | 0.25 |
| 100 µmol/L IL-10 (−3575) R primer | 0.5 |
| 5 U/µL Gene Taq FP* | 0.25 |
| Total | 46 µL |

*Trade name: Gene Taq FP, manufactured by Nippon Gene Co., Ltd.
IL-10 (−1082) probe (SEQ ID NO. 47)
5'-(BODIPY FL)-ccctacttccccCtccc-P- 3'
IL-10(−1082) F primer (SEQ ID NO. 213)
5'-ccgcaacccaactggctctccttac-3'
IL-10(−1082) R primer (SEQ ID NO. 227)
5'-ggattccatggaggctggataggaggtcc-3'
IL-10(−3575) probe (SEQ ID NO. 57)
5'-(TAMRA)-cccactggaaaaatTcattt-P-3'
IL-10(−3575) F primer (SEQ ID NO. 244)
5'-ggatggaagaagagaggtattccccttcccac-3'
IL-10(−3575) R primer (SEQ ID NO. 260)
5'-ccagtttgccctcaagcccagatgc-3'

Figure 3:
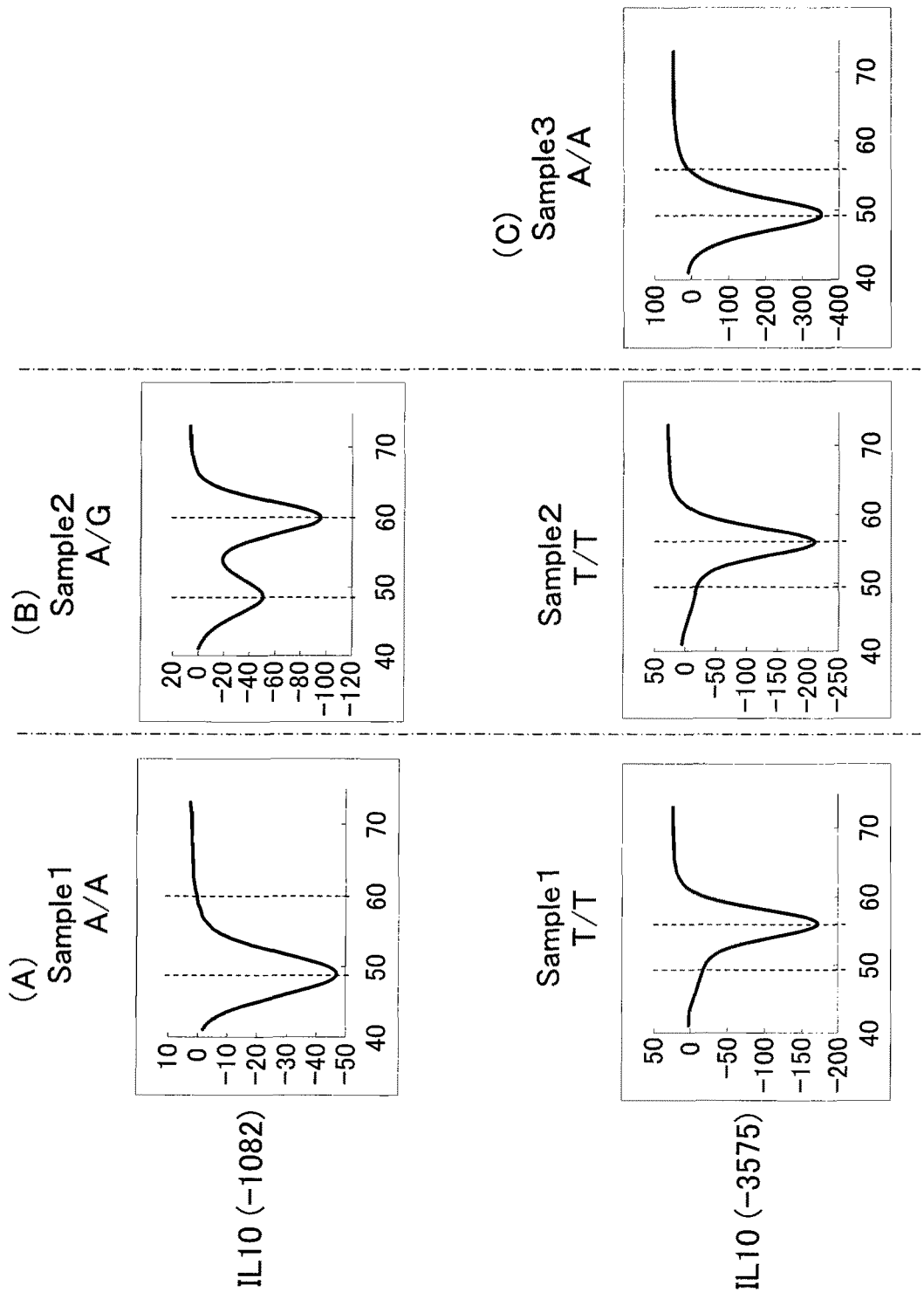
FIG. 3 depicts graphs showing the results of a Tm analysis in Example 3 of the present invention.

FIG. 3 shows the results. FIG. 3 depicts graphs of a Tm analysis that shows the change in fluorescence intensity associated with the temperature increase. In FIG. 3, "(A)" shows the results of Sample 1, "(B)" shows the results of Sample 2, "(C)" shows the results of Sample 3, the upper row shows the results for the IL-10 (−1082) polymorphisms, and the bottom row shows the results for the IL-10 (−3575) polymorphisms.

In this example, a probe that perfectly matched the IL-10 (−1082) polymorphism (g) of the sense strand was used as an IL-10 (−1082) probe, and a probe that perfectly matched the IL-10 (−3575) polymorphism (a) of the antisense strand was used as an IL-10 (−3575) probe. This is synonymous with perfectly matching the IL-10 (−3575) polymorphism (t) of the sense strand. As a result, in the detection of an IL-10 (−1082) polymorphism, Sample 1, which contains a homozygote (A/A), showed a peak only at 49.0° C., indicating a mismatch, and on the other hand, Sample 2, which contains a heterozygote (A/G), showed a peak at 60.0° C., indicating a perfect match, as well as a peak at 49.0° C., indicating a single-base mismatch, as shown in the upper row of FIG. 3. Moreover, in the detection of an IL-10 (−3575) polymorphism, Sample 1 and Sample 2, which contain homozygotes (T/T), showed a peak only at 56.0° C., indicating a perfect match, and Sample 3, which contains a homozygote (A/A), showed a peak only at 49.0° C., indicating a mismatch, as shown in the bottom row of FIG. 3. As can be understood from the results, using probes of the present invention, whether hybridization with a detection target sequence is of a perfect match or a mismatch can be sufficiently determined, and two types of polymorphisms can be determined using a single reaction system.

As can be understood from the results presented above, using the probes of the present invention, whether hybridization with a detection target sequence is of a perfect match or of a mismatch can be fully determined. Therefore, according to the present invention, whether a polymorphism in a detection target site is a polymorphism (X) or a polymorphism (Y) can be distinguished with good accuracy. Moreover, since it is possible to determine between a perfect match and a mismatch, it is possible to determine, for example, whether a polymorphism to be detected is a homozygote (X/X or Y/Y) or a heterozygote (X/Y) and, in addition, whether the polymorphism is a homozygote (X/X) or a homozygote (Y/Y). Furthermore, it is possible to determine two or more types of polymorphisms in one reaction system.

INDUSTRIAL APPLICABILITY

As described above, in connection with the immune-related genes FCGR3A, FCGR2A, IL-10, TNF α and TNF β, it is possible according to the present invention to distinguish polymorphisms in which only one base is different. Therefore, by applying the probes of the present invention to, for example, a Tm analysis or the like, polymorphism detection can be carried out in a simple manner. Moreover, according to the present invention, even when two or more types of probes are concomitantly present in one reaction system, corresponding gene polymorphisms can be distinguished by the respective probes. Therefore, a plurality of polymorphisms can be detected using one reaction system. Thus, according to the present invention, since polymorphisms of immune-related genes can be readily distinguished, the results of detection can be reflected also in, for example, the therapeutic administration of antibody drugs as described above. Therefore, the present invention is particularly useful in the medical field and like technical fields.

The invention claimed is:

1. A polymorphism detection probe consisting of oligonucleotide (A) and at least one fluorescent dye bonded to said oligonucleotide (A),
wherein the oligonucleotide (A) consists of the nucleotide sequence of SEQ ID NO: 14 or the complementary sequence thereof.

2. The polymorphism detection probe according to claim 1, wherein the probe does not emit fluorescence when alone and emits fluorescence when forming a hybrid.

3. The polymorphism detection probe according to claim 1, wherein the probe emits fluorescence when alone and emits reduced fluorescence when forming a hybrid.

4. The polymorphism detection probe according to claim 1, wherein the at least one fluorescent dye is bonded to the cytosine at the 3' end of the oligonucleotide (A).

5. A polymorphism detection reagent for detecting a polymorphism of an immune-related gene, comprising the polymorphism detection probe of claim 1.

6. A method of detecting a polymorphism in a FCGR3A gene, comprising:
hybridizing a sample nucleic acid and the polymorphism detection probe of claim 1,
measuring a fluorescence signal value that indicates the melting state of one or more products of the hybridization in a reaction system while changing the temperature of the reaction system; and
determining the polymorphism in the sample nucleic acid based on a change in the fluorescence signal value associated with the temperature change.

7. The method of detecting a polymorphism according to claim 6, wherein
the method comprises:
generating in the reaction system an amplification product that serves as the sample nucleic acid.

8. The polymorphism detection probe according to claim 1, wherein the oligonucleotide (A) consists of the nucleotide sequence of SEQ ID NO: 14.

9. The polymorphism detection probe according to claim 1, wherein the fluorescent dye is selected from the group consisting of fluoresceins, phosphors, rhodamine, and polymethine dye.

* * * * *